United States Patent
Paul et al.

(10) Patent No.: US 9,006,388 B2
(45) Date of Patent: *Apr. 14, 2015

(54) COVALENT ATTACHMENT OF LIGANDS TO NUCLEOPHILIC PROTEINS GUIDED BY NON-COVALENT

(75) Inventors: Sudhir Paul, Missouri City, TX (US); Yasuhiro Nishiyama, Houston, TX (US)

(73) Assignee: Sudhir Paul, Missouri City, TX (US)

( * ) Notice: Subject to any disclaimer, the term of this patent is extended or adjusted under 35 U.S.C. 154(b) by 2029 days.

This patent is subject to a terminal disclaimer.

(21) Appl. No.: 10/581,296

(22) PCT Filed: Mar. 26, 2004

(86) PCT No.: PCT/US2004/009399
§ 371 (c)(1),
(2), (4) Date: Jun. 1, 2006

(87) PCT Pub. No.: WO2004/087059
PCT Pub. Date: Oct. 14, 2004

(65) Prior Publication Data
US 2007/0179083 A1    Aug. 2, 2007

Related U.S. Application Data

(60) Provisional application No. 60/457,293, filed on Mar. 26, 2003.

(51) Int. Cl.
| | |
|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 47/48 | (2006.01) |
| C07K 14/005 | (2006.01) |
| C07K 16/10 | (2006.01) |
| A61K 39/00 | (2006.01) |

(52) U.S. Cl.
CPC ..... *A61K 47/48238* (2013.01); *A61K 2039/505* (2013.01); *A61K 2039/60* (2013.01); *A61K 2039/6093* (2013.01); *C07K 14/005* (2013.01); *C07K 16/1063* (2013.01); *C07K 2316/96* (2013.01); *C07K 2317/34* (2013.01); *C12N 2740/16122* (2013.01)

(58) Field of Classification Search
CPC ............ A61K 39/505; A61K 2039/60; A61K 2039/6093; A61K 47/48238; C07K 14/005; C07K 16/1063; C07K 2316/96; C07K 2317/34; C07K 2740/16122
See application file for complete search history.

(56) References Cited

U.S. PATENT DOCUMENTS

| | | | |
|---|---|---|---|
| 5,434,133 A * | 7/1995 | Tanaka et al. | 514/12 |
| 5,445,960 A | 8/1995 | Masuho et al. | |
| 5,695,927 A | 12/1997 | Masuho et al. | |
| 5,783,670 A | 7/1998 | Masuho et al. | |
| 5,801,149 A * | 9/1998 | Shoelson | 514/8.2 |
| 5,807,715 A | 9/1998 | Morrison et al. | |
| 5,811,238 A | 9/1998 | Stemmer et al. | |
| 5,952,462 A | 9/1999 | Powell et al. | |
| 6,156,541 A | 12/2000 | Paul et al. | |
| 6,235,714 B1 * | 5/2001 | Paul et al. | 424/195.11 |
| 6,406,863 B1 | 6/2002 | Zhu et al. | |
| 6,407,213 B1 | 6/2002 | Carter et al. | |
| 6,855,804 B2 * | 2/2005 | Paul et al. | 530/324 |
| 7,524,663 B2 * | 4/2009 | Paul et al. | 435/188.5 |
| 2003/0078203 A1 | 4/2003 | Paul et al. | |
| 2009/0117115 A1 * | 5/2009 | Paul et al. | 424/139.1 |
| 2010/0183614 A1 * | 7/2010 | Paul et al. | 424/135.1 |
| 2012/0121633 A1 * | 5/2012 | Paul et al. | 424/188.1 |

FOREIGN PATENT DOCUMENTS

| | | |
|---|---|---|
| WO | WO 2004/087059 | 10/2004 |
| WO | WO 2004/087735 | 10/2004 |
| WO | WO 2004/087738 | 10/2004 |

OTHER PUBLICATIONS

Zhou et al. Prospects for immunotherapeutic proteolytic antibodies. Journal of Immunological Methods, 2002. vol. 269, pp. 257-268.*
Horwitz et al. The substrate specificity of brain microsomal phospholipase D. Biochem J (1993), vol. 295, pp. 793-798.*
International Search report, PCT/US04/09399, mailed Jun. 1, 2005.
Written Opinion of the International Searching Authority, PCT/US04/09399, mailed Jun. 1, 2005.
International Search report, PCT/US04/09662, mailed Jun. 28, 2006.
Written Opinion of the International Searching Authority PCT/US04/09662, mailed Jun. 28, 2006.
Mar. 28, 2003, Paul et al., Specific HIV gp 120-cleaving antibodies induced by covalently reactive analog of gp 120. J. Biol. Chem. May 30, 2003, vol. 278, No. 22, pp. 20429-20435.
Nishiyama et al., "Antibodies to the Superantigenic Site of HIV-1 gp 120: Hydrolytic and Binding Aactivities of the Light Chain Subunit" submitted with U.S. Appl. No. 60/857,764, filed Nov. 9, 2006.

(Continued)

*Primary Examiner* — Marcela M Cordero Garcia
(74) *Attorney, Agent, or Firm* — Robert C. Netter, Jr.; Kathleen D. Rigaut; Dann, Dorfman, Herrell & Skillman

(57) ABSTRACT

A covalently reactive ligand analogue (CAL) of formula (1): wherein, $L_1 \ldots L_x \ldots L_m$ are components defining a ligand determinant, $L_x$ is a component unit of the ligand determinant selected from the group consisting of an amino acid residue, sugar residue, a fatty acid residue and a nucleotide, L' is a functional group of $L_x$, Y" is atom, covalent bond or linker, Y' is an optional charged or neutral group Y is a covalently reactive electrophilic group that reacts specifically with a receptor that binds to said ligand determinant, and n is an integer from 1 to 1000 m is an integer from 1 to 30.

28 Claims, 36 Drawing Sheets

(56) References Cited

OTHER PUBLICATIONS

"Induction of antibodies to the gp120 superantigenic site by administration of protein A" submitted with U.S. Appl. No. 60/857,764, filed Nov. 9, 2006.

Planque et al., "Naturally Occurring Catalytic IgAs: Protective Anti-HIV Mediators?" submitted with U.S. Appl. No. 60/857,764, filed Nov. 9, 2006.

Planque et al., "Ontogeny of Proteolytic Immunity: IgM Serine Proteases" submitted with U.S. Appl. No. 60/534,689, filed Jan. 8, 2004.

Karle et al., "Selective IgM-Catalyzed Hydrolysis of HIV gp120: An innate defense against gp120?" submitted with U.S. Appl. No. 60/534,689, filed Jan. 8, 2004.

Dec. 15, 2003, Nishiyama et al., "Toward selective covalent inactivation of pathogenic antibodies" J. Biol. Chem. Feb. 27, 2004, vol. 279, No. 9, pp. 7877-7883.

Planque et al., "Broadly Distributed Chemical Reactivity of Natural Antibodies Expressed in Coordination with Specific Antigen Binding Activity" submitted with U.S. Appl. No. 60/457,293, filed Mar. 26, 2003.

Karle et al., "HIV-1 Neutralizing Antibody Fragments to a Conserved Envelope Determinant from Lupus Libraries" submitted with U.S. Appl. No. 60/457,570, filed Mar. 27, 2003.

Paul et al., "Natural catalytic immunity is not restricted to autoantigenetic substrates: Identification of a human immunodeficiency virus gp120-cleaving antibody light chain" Appl. Biochem Biotechnol. Jan.-Mar. 2000, vol. 83, No. 1-3, pp. 71-82.

Pinto et al. "Panel of anti-gp 120 monoclonal antibodies reacts with same nuclear proteins in uninfected cells as those recognized by autoantibodies from patients with systemic lulus erythematosus" Aids Res. and Hum Retroviruses, Nov. 7, 1994, vol. 10, pp. 823-828.

Fraziano et al., "Epitope specificity of anti-HIV antibodies in human and murine autoimmune diseases" Aids Research and Human Retroviruses, Nov. 6, 1996, vol. 12, No. 6, pp. 491-496.

Root-Bernstein, "Preliminary evidence for idiotype-antidiotype immune complexes cross-reactive with Lymphocyte antigenss in AIDS and lupus" Medical Hypotheses (1995) 44, 20-27.

Taguchi et al. "A mechanism-based probe for gp 120-hydrolyzing antibodies" Bioorg. Med. Chem. Lett. 2002, vol. 12, pp. 3167-3170.

* cited by examiner

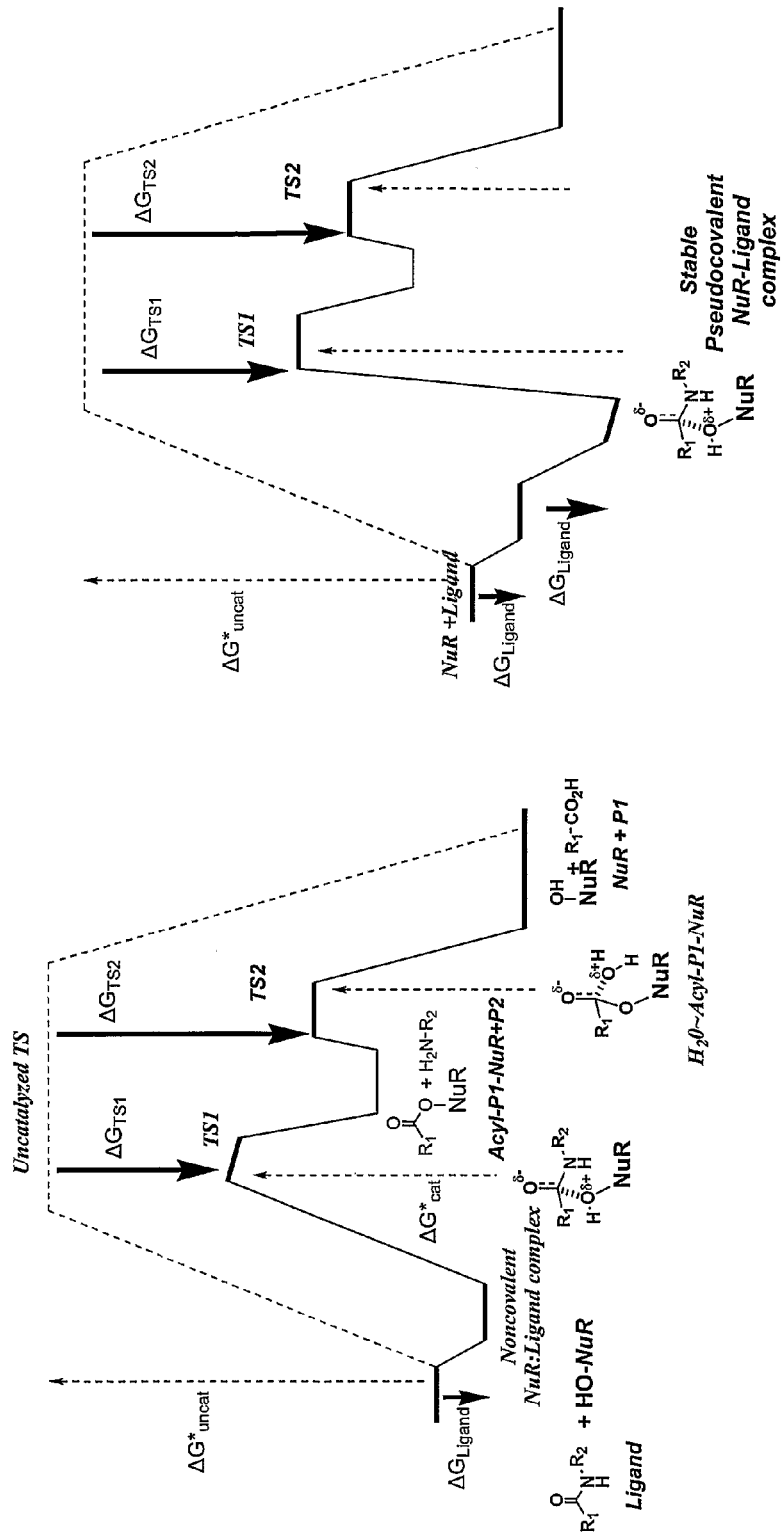
Fig 3 Catalysis and covalent binding energies of proteins

Fig 4

General structure of LaCAL

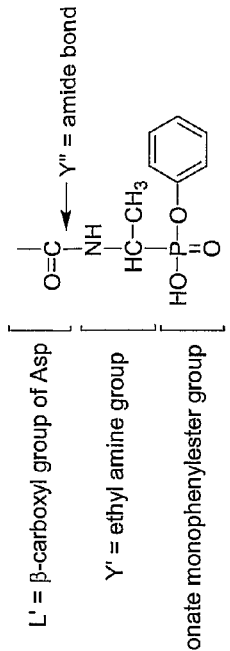

L'-Y''-Y'-Y, Example 1

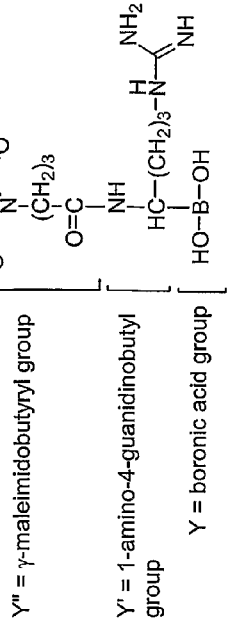

- L' = β-carboxyl group of Asp
- Y'' = ethyl amine group
- Y' = phosphonate monophenylester group

L'-Y''-Y'-Y, Example 2

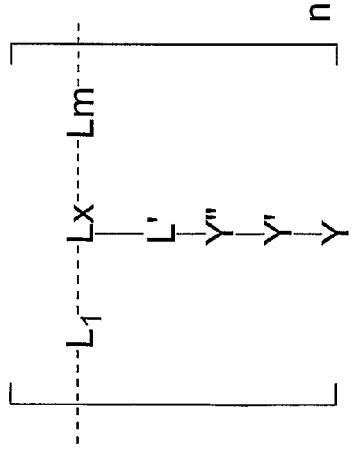

- L' = ε-amino group of Lys
- Y'' = suberic acid residue
- Y' = (4-amidinophenyl)methylamine group
- Y = phosphonate diphenyl ester group

L'-Y''-Y'-Y, Example 3

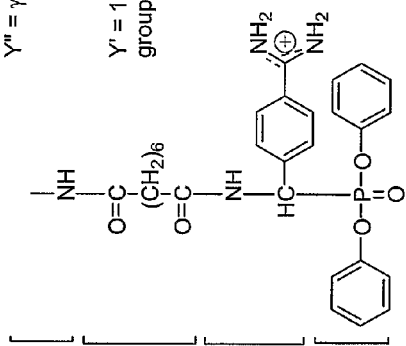

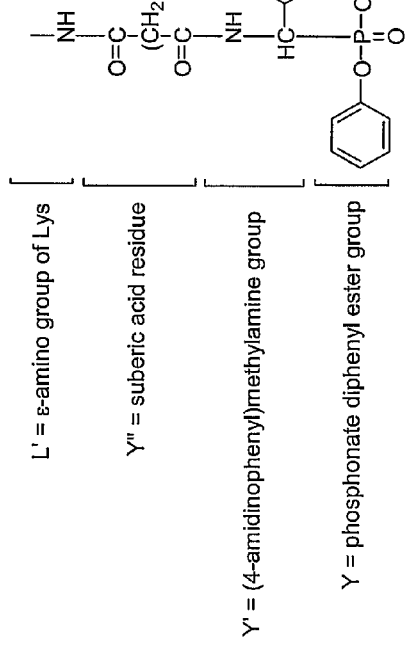

- Y'' = γ-maleimidobutyryl group
- Y' = 1-amino-4-guanidinobutyl group
- Y = boronic acid group

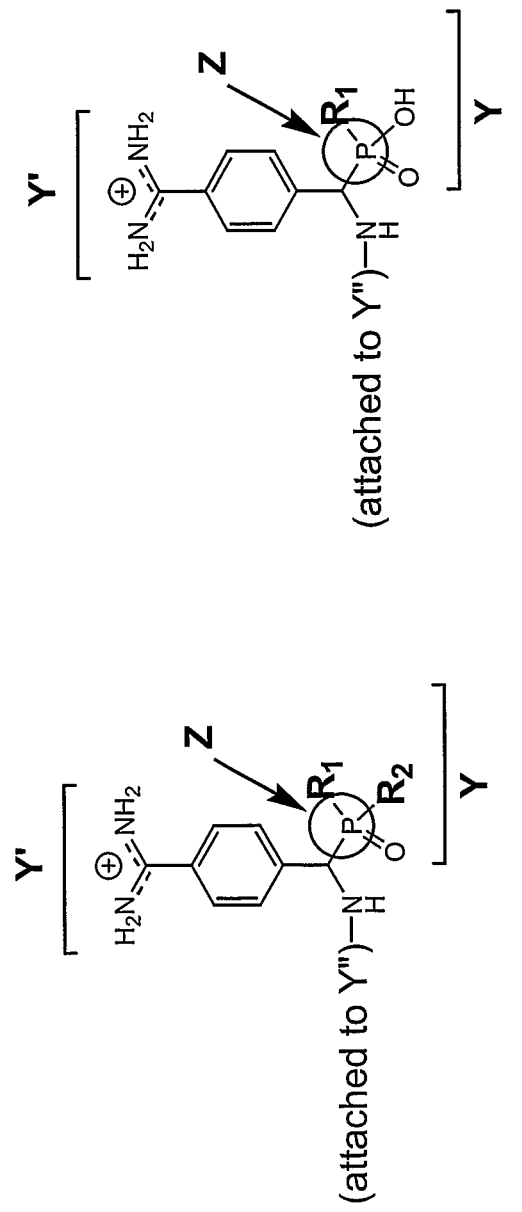

Fig 5D
A. Electron withdrawing substituents with peptide extension
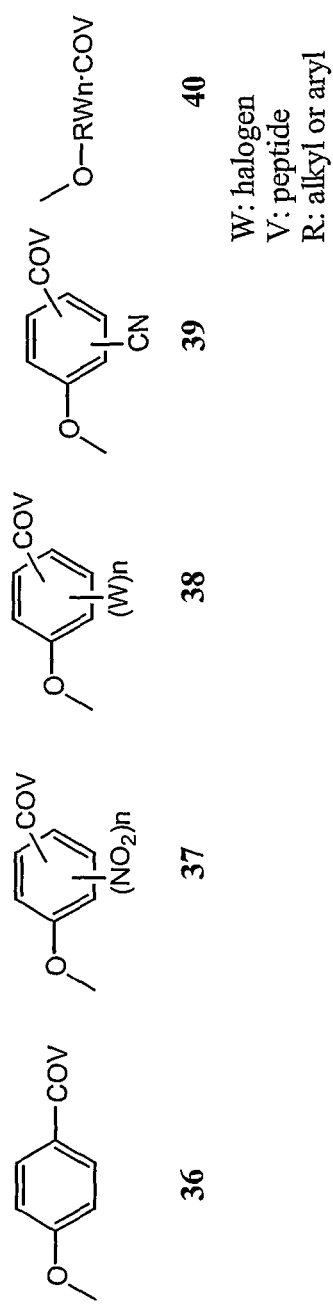
B. Electron donating substituents with peptide extension
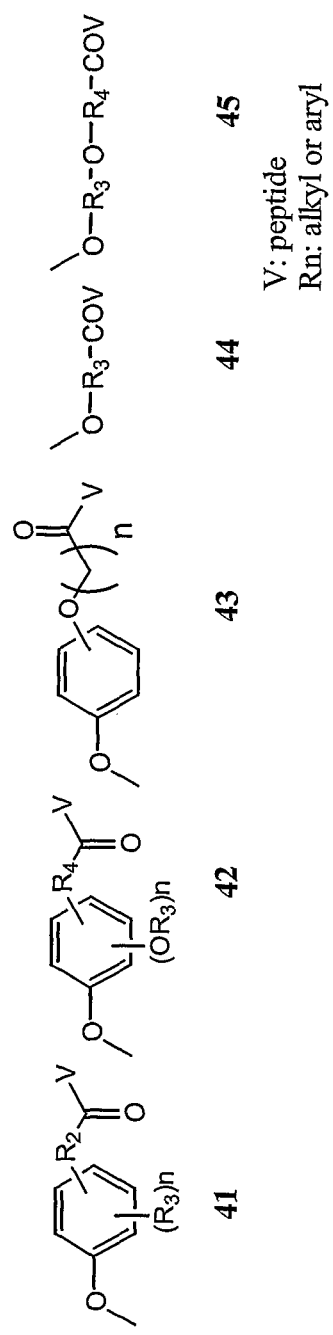

Fig 10

Fig 14
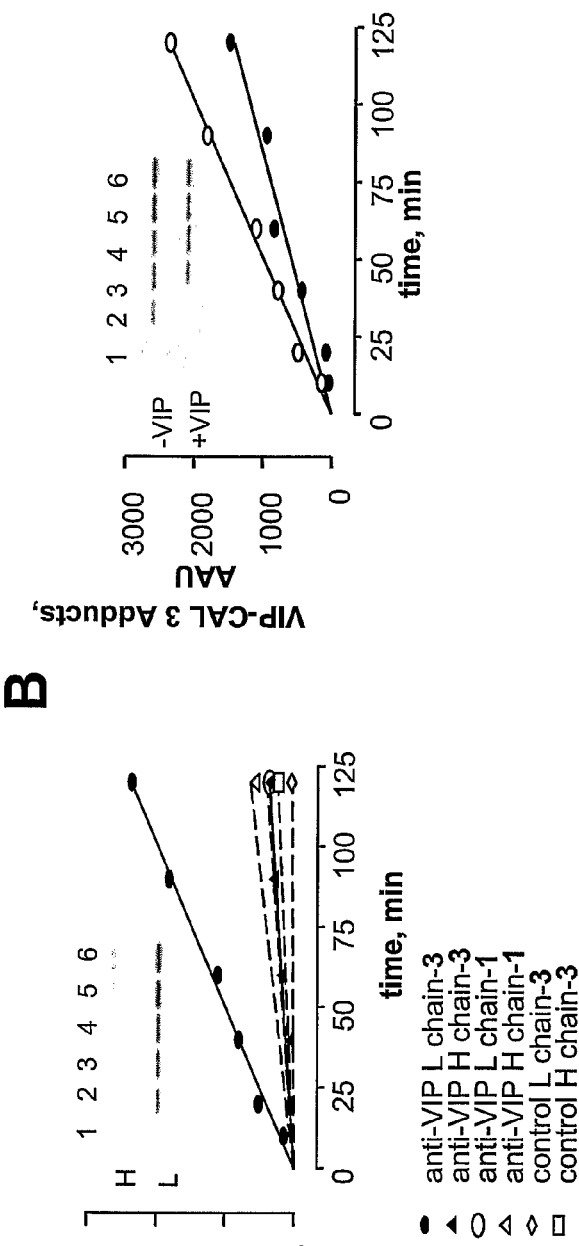
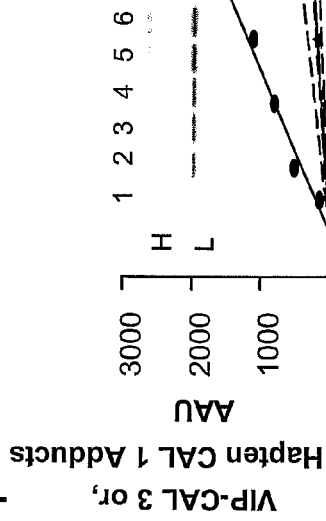
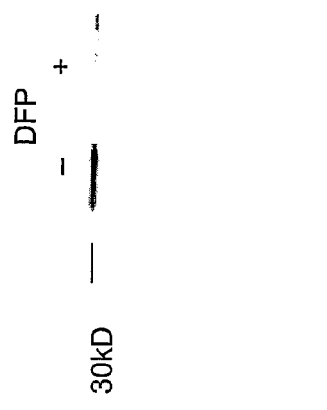

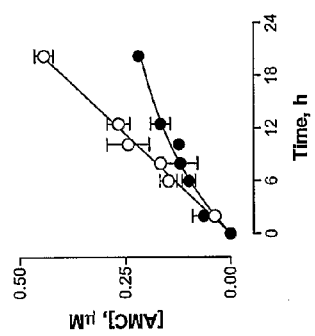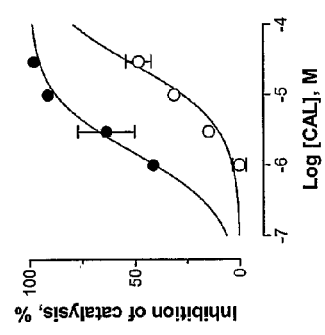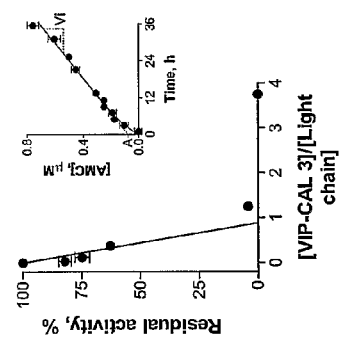
Fig 15

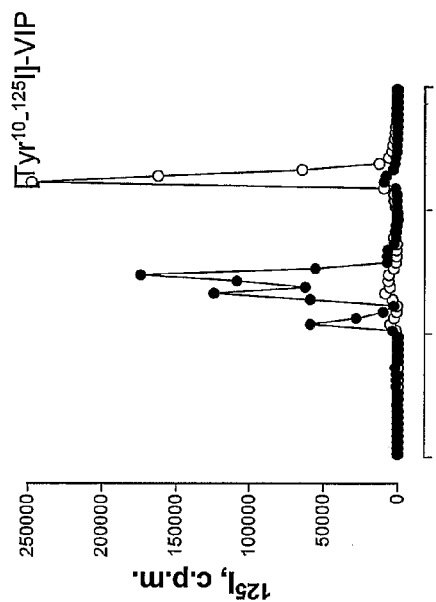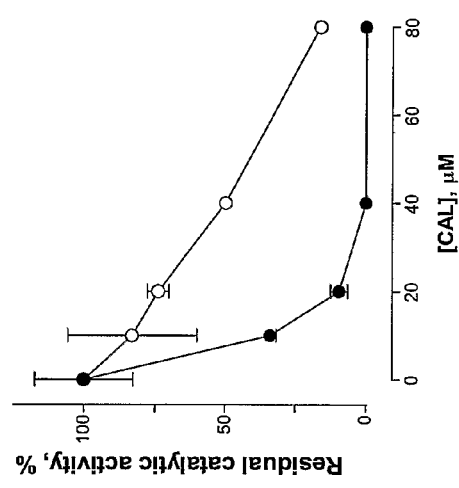
Fig 16

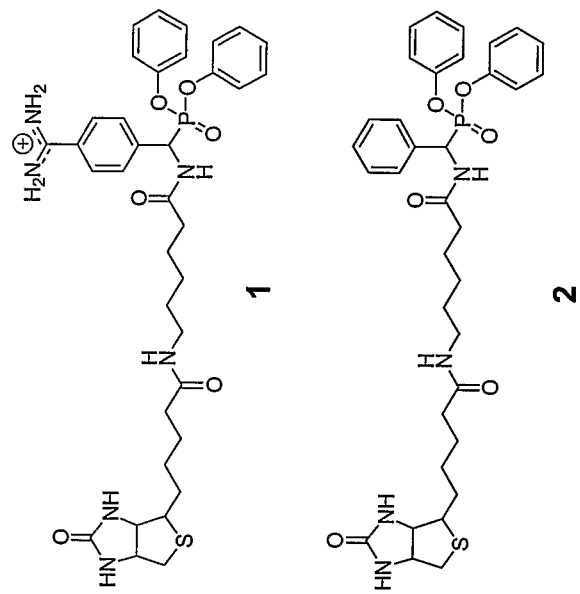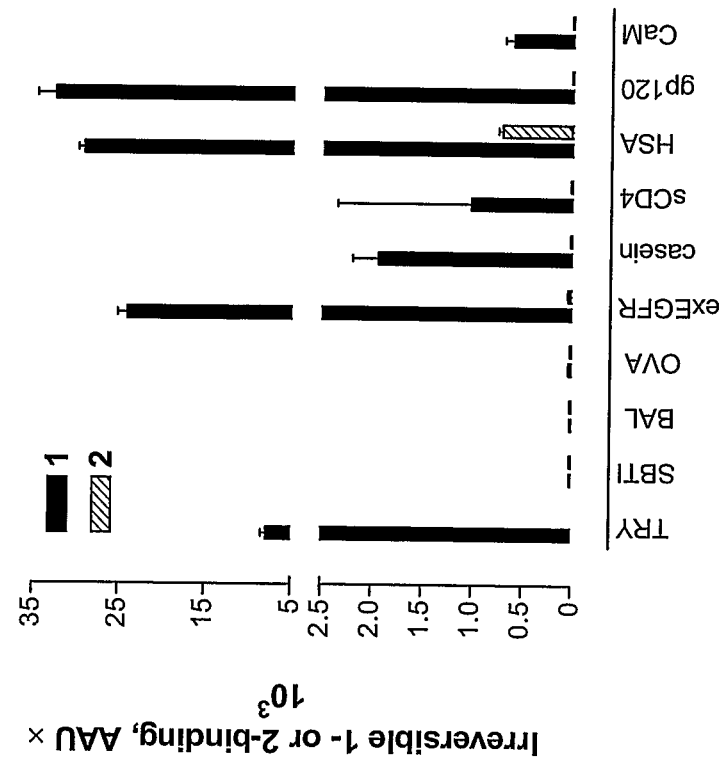
Fig 23

Fig 26
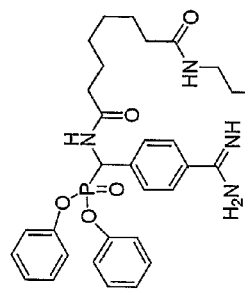
R-His-Ser-Asp-Ala-Val-Phe-Thr-Asp-Asn-Tyr-Thr-Arg-Leu-Arg-Lys-Gln-Met-Ala-Val-Lys-Tyr-Leu-Asn-Ser-Ile-Leu-Asn-NH$_2$
3: R = D-biotinyl
A
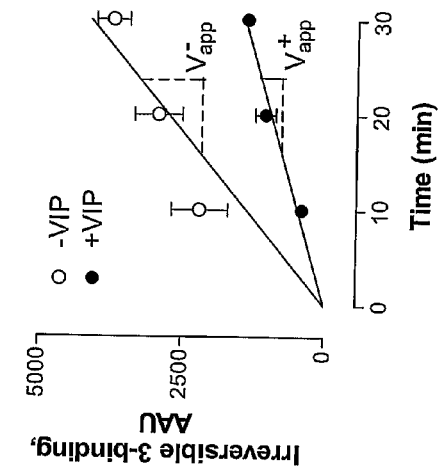
B
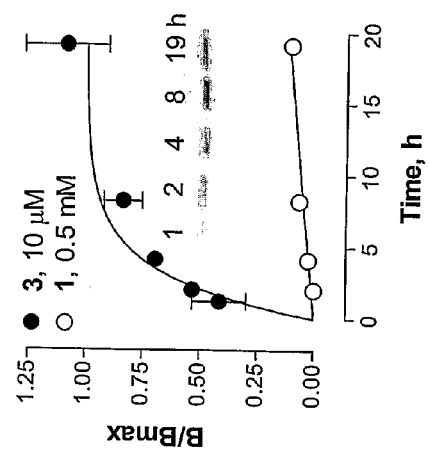
C

COVALENT ATTACHMENT OF LIGANDS TO NUCLEOPHILIC PROTEINS GUIDED BY NON-COVALENT

This application is a §371 application of PCT/US2004/009399, filed Mar. 26, 2004, which in turn claims priority to U.S. Provisional Application No. 60/457,293, filed Mar. 26, 2003. The entire disclosure of each of the foregoing applications is incorporated by reference herein.

U.S. Government grants AI046029, CA080312, HL094126, and HL059746 contributed to the development of this technology.

SUMMARY OF THE INVENTION

Non-catalytic proteins were discovered to display nucleophilic reactivity upon specific binding to weakly electrophilic, active site-directed compounds. These activated nucleophiles function in register with conventional noncovalent binding sites in the protein. Until now, such activated nucleophiles were thought to exist only in the catalytic sites of enzymes, such as those found in serine proteases. In the present invention, nucleophilic sites have been identified in several non-enzymatic proteins, including albumin, calmodulin, gp120 and antibodies directed to gp120, EGFR and Factor VIII. The presence of activated nucleophiles in these proteins indicates the formation of specific non-covalent bonding interactions with the inventive compounds that arise from protein folding and protein interactions with other macromolecules and small molecules.

Biotin-containing and fluorescent electrophilic esters are employed to identify the nucleophilic sites. Non-covalent binding to moieties in the spatial neighborhood of the electrophilic atom allowed targeting of the active-site nucleophiles in proteins with defined binding specificity. For the purpose of this invention, a ligand and receptor are defined as any pair of molecules that can become associated via noncovalent bonding forces, including molecules of the same protein. Such nucleophilic proteins are designated nucleophilic receptors (NuRs). Electrophilic analogs of ligands capable of covalent binding to NuRs guided by noncovalent interactions are designated CALs (Covalent Analogues of Ligands). In the extreme case, CALs of NuRs are prepared (designated CAL-NuRs), allowing a given molecule of the CALNuR expressing to a nucleophile to bind covalently to a second CALNuR molecule at the covalently reactive electrophile incorporated within the CALNuR.

The invention can be used for:
Irreversible inhibition of pathogenic NuR activities using CALs;
Formation of covalently bonded, stable mimics of non-covalent, supramolecular CALNuRs complexes with correspondingly stabilized biological activity;
Facile isolation of individual NuR polypeptides and their genes from libraries displayed on the surface of viruses, prokaryotic cells and eukaryotic cells, including NuRs capable of covalent binding to natural, unmodified macromolecules and small molecules;
Directed evolution of NuRs expressing the desired binding activity by random or directed sequence diversification followed by selection for active site nucleophiles in register with the non-covalent binding site.

An object of the invention is to provide a covalently reactive ligand analogue (CAL) of formula (1):

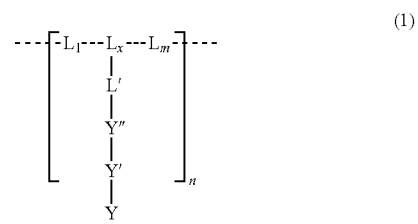

wherein, L1 ... Lx ... Lm are components of a ligand determinant,
Lx is a component unit of the ligand determinant selected from the group consisting of an amino acid residue, sugar residue, a fatty acid residue and a DNA residue,
L' is a functional group of Lx,
Y" is linker or a covalent bond,
Y' is a charged or neutral group
Y is a covalently reactive electrophilic group that reacts specifically with a receptor that binds to said ligand determinant,
n is an integer from 1 to 1000, and
m is an integer from 1 to 30.

Another object of the invention is to provide a method for inactivating or activating soluble nucleophilic receptors (NURs), comprising: contacting a compound of formula (1) with a solution containing a NUR that reacts specifically with the ligand determinant of said compound.

An object is to provide a method for inactivating or activating nucleophilic receptors produced by a microorganism, comprising: contacting a compound of formula (1) with a microorganism containing a NUR that reacts specifically with the ligand determinant of said compound, including, in particular pathogenic viruses such as HIV-1 and HCV.

Another object of the invention is to provide a method for antagonism or agonism of nucleophilic receptors (NURs) expressed on cellular surfaces, comprising: contacting a compound of formula (1) with a cell containing a NUR that reacts specifically with the ligand determinant of said compound, including, in particular, the receptor for epidermal growth factor, the receptor for vasoactive intestinal peptide and CD4.

Another object is to provide a method for inducing the death of lymphocyetes, comprising: contacting a compound of formula (1) with lymphocytes that express a NUR which reacts specifically with the ligand determinant of said compound.

Still another object is to provide methods for preparing a stable self-assembled biomolecules comprising multiple units of a compound of formula (1).

Another object is to provide a stable self-assembled oligomeric gp120-CAL for vaccination against HIV.

Another object is to use self-assembled biomolecules oligomeric gp120-CAL as an immunogen to generate monoclonal antibodies suitable for immunotherapy of HIV infection. HIV.

Another object of the invention is to provide a method for imaging cells that express a NUR on their surface, comprising: exposing a suitably labeled derivative of a CAL of formula (1) to the cells which are to be imaged, and detecting the label.

Another object is to provide compounds suitable for the isolation, induction and inhibition of antibodies Another object is to provide compounds suitable for isolation of proteins with improved ligand binding and enzymatic activity by in vitro directed evolution procedures, including, in particular, hormones such as growth hormone, neuropeptides such as vasoactive intestinal peptide, enzymes such as subtilisin and antibodies such as antibodies to HIV-1.

Another object is to provide improved immunoassays for detection of antibodies and antigens by use of compounds with the formula (1), including, in particular detection of antibodies to viruses such as HIV and HCV.

DESCRIPTION OF DRAWINGS

FIG. 3: Reaction mechanism for serine protease Abs. Left, Nucleophilic group Nu of the receptor (NuR) stabilize the ligand ground state noncovalently ($\Delta G_{Ligand}$). Nucleophiles such as an activated Ser residue attacks the peptide bond, forming an unstable resonant transition state (TS1). Completion of this reaction forms the covalent acyl-Ab intermediate, with release of the C terminal peptide fragment. In the second reaction, a water molecule hydrolyzes the covalent intermediate via a second tetrahedral transition state (TS2). Right, The reaction proceeds as above, except that the resonant ligand-NuR complex containing partial covalent bonds (TS1 above) is more stable than the ground state of the ligand-NuR complex. $\Delta G^{\dagger}_{uncat}$ and $\Delta G^{\dagger}_{cat}$ correspond to activation energies for the uncatalyzed and catalyzed reactions, respectively. $K_m$ is a function of the extent of ground state stabilization ($\Delta G_S$). $k_{cat}/K_m$ is a function of extent of transition state stabilization relative to the catalyst-substrate ground state complex.

FIG. 4. General representation of LaCALs. These compounds are composed of one or more determinants that bind the receptor in conjuncation with the electrophilic group. The receptor binding determinant is composed of continuous or discontinuous ligand components [L1 . . . Lx . . . Lm]. L' is a functional group of a ligand component Lx, to which the Y-Y'-Y" unit containing an electrophile is attached. Y is the electrophilic atom or group capable of forming a full or partial covalent bond the with nucleophilic group (Nu) of the antibody. Y' and Y", are, respectively, an optional P1 subsite and an optional adaptor functionality. Y' is an atom, bond or chemical group that connects Y and L' or Y", and can provide additional effects that regulate the reactivity of LaCALs independent of the electrophilicity of Y. Y" is an atom, bond or chemical group that connect Y' and Lx' and enables control of the distance between Y and the receptor binding determinant, and the spatial positioning of these groups. Example 1: Y is the phosphonate monophenyl ester group, which forms the covalent bond with the Ab Nu. Y' is the ethylamine group that connects Y and the β-carboxyl group (L') of Asp (Lx) via an amide bond (Y") and presents a methyl flank, which can facilitate the covalent binding to an antibody with a small hydrophobic pocket near Nu. Example 2: Y is the phosphonate diphenyl ester group, which forms the covalent bond with the Ab Nu. Y' is the (4-amidinophenyl)methylamine group that connects Y and suberic acid group (Y"). The 4-amidinophenyl flank of Y' can facilitate the covalent binding to a receptor with a negatively charged pocket near Nu. Another functionality of Y" is connected to the ε-amino group (L') of Lys (Lx). Example 3: Y is the boronic acid group, which forms the covalent bond with Nu. Y' is the 1-amino-4-guanidinobutylamine group that connects Y and γ-maleimidobutyric acid group (Y"). The guanidinopropyl flank of Y' can facilitate the covalent binding to a receptor with a negatively charged pocket near Nu. The maleimide group of Y" is connected to the sulfhydryl group (L') of Cys (Lx).

Example 1

Figure 7:
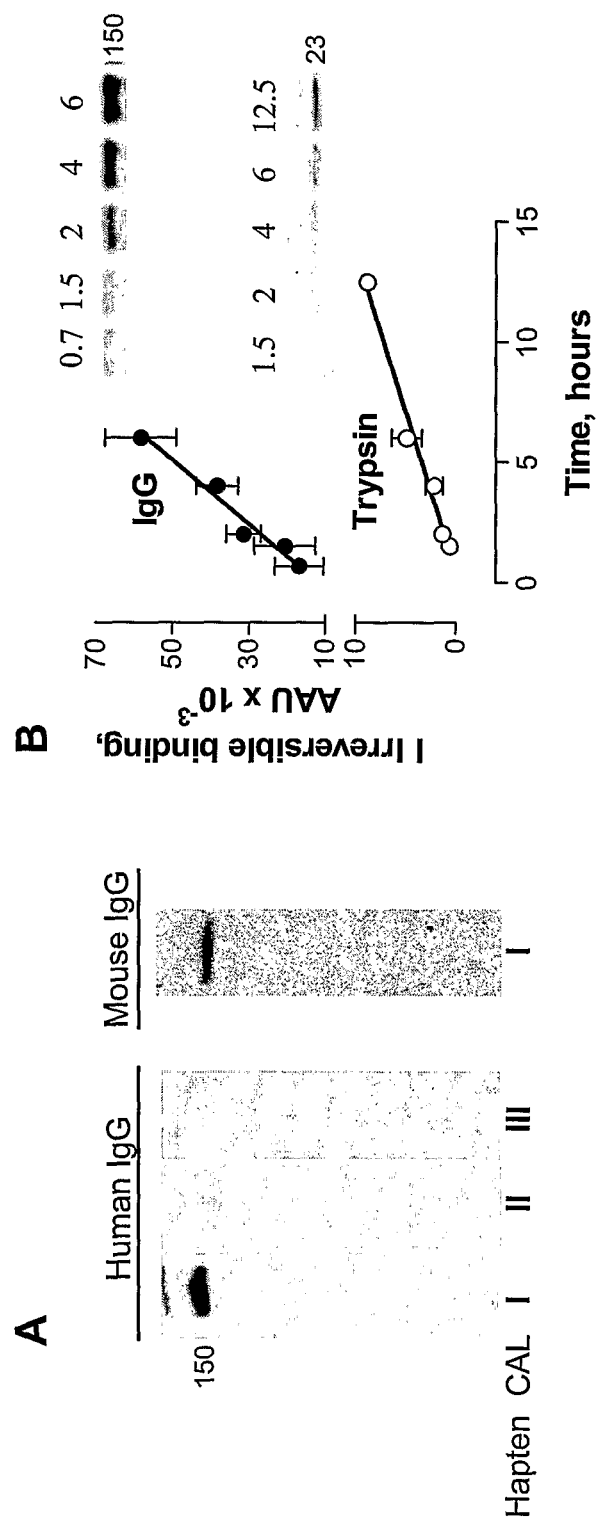

FIG. 7. Hapten CAL binding by IgG and trypsin. A, Representative streptavidin-peroxidase stained blots of SDS-polyacrylamide gels showing adducts of I with human (#1518) and murine (BALB/c) serum IgG (1 µM). A weak reaction of IgG with II was observed by exposing the gel for a prolonged period (4 h) and no reaction with III was evident. Hapten CAL, 10 µM, 60 min. B, Time course of IgG-I and trypsin-I binding determined in triplicate. Y-axis values are intensities of the 150 kD (IgG) or 23 kD (trypsin) adduct bands expressed in arbitrary area units (AAU). Hapten CAL 1, 100 µM. Inset, streptavidin-peroxidase stained blots of SDS-polyacrylamide gels showing biotin-containing adducts (top, IgG; bottom, trypsin).

Figure 8:
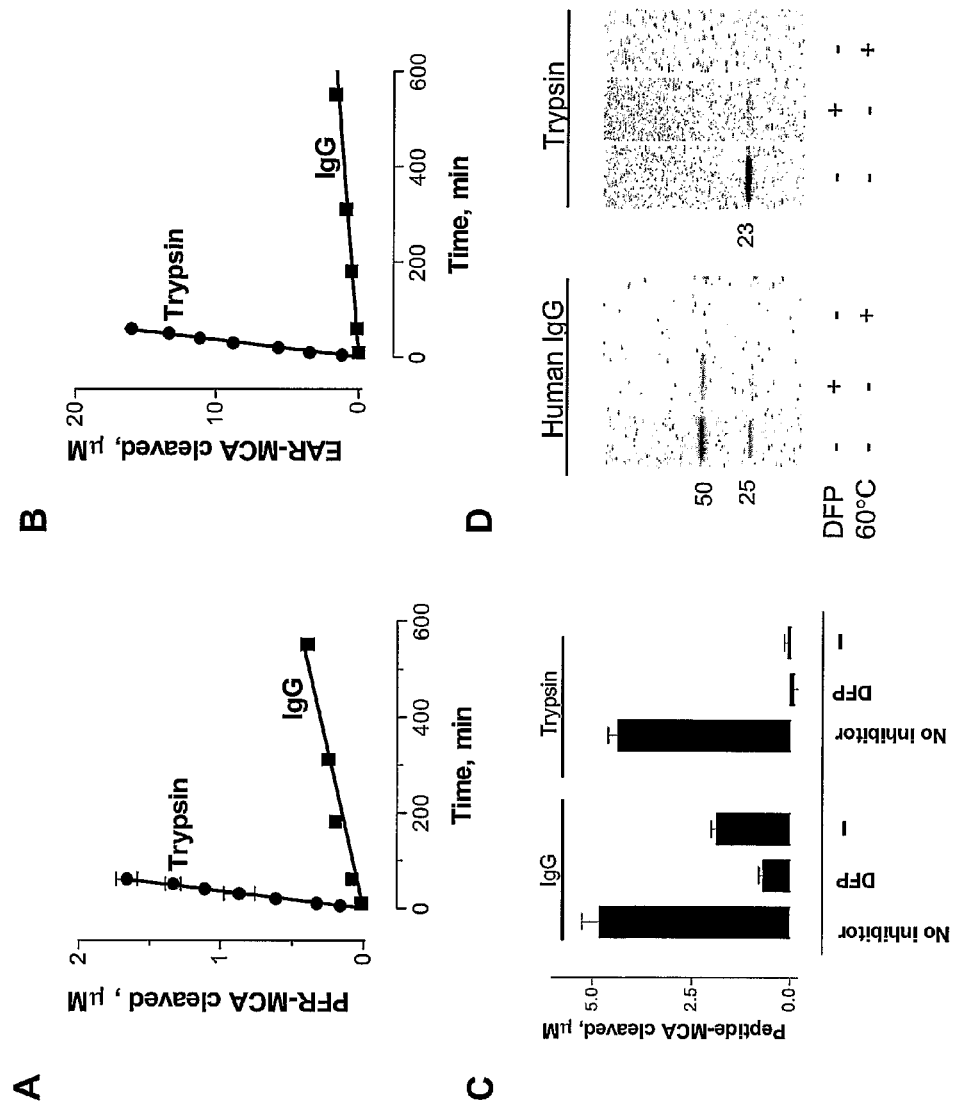

FIG. 8. Catalytic and hapten CAL I binding characteristics of human IgG (#1518) and trypsin. A, Time course of cleavage of Pro-Phe-Arg-MCA (200 µM, IgG 500 nM, trypsin 0.1 nM). B, Time course of cleavage of Glu-Ala-Arg-MCA (200 µM, IgG 500 nM, trypsin 0.1 nM). C, DFP (5 mM) and CAL I (0.1 µM) inhibition of peptide-MCA (mixture of Glu-Ala-Arg-MCA, Pro-Phe-Arg-MCA and Ile-Glu-Gly-Arg-MCA; 67 µM each) cleavage by IgG (375 nM) and trypsin (1 nM); respectively, 21 h and 1.5 h reaction. D, Representative streptavidin-peroxidase stained blots of reducing SDS-polyacrylamide gels showing inhibition of I (10 µM) adduct formation by DFP (5 mM) and preheating of the proteins for 10 min. IgG, 1 µM; trypsin, 1 µM. 1 h reaction. Treatment with DFP for 30 min prior to incubation with I. Values in A-C are means of 3 replicates±s.d.

Figure 9:
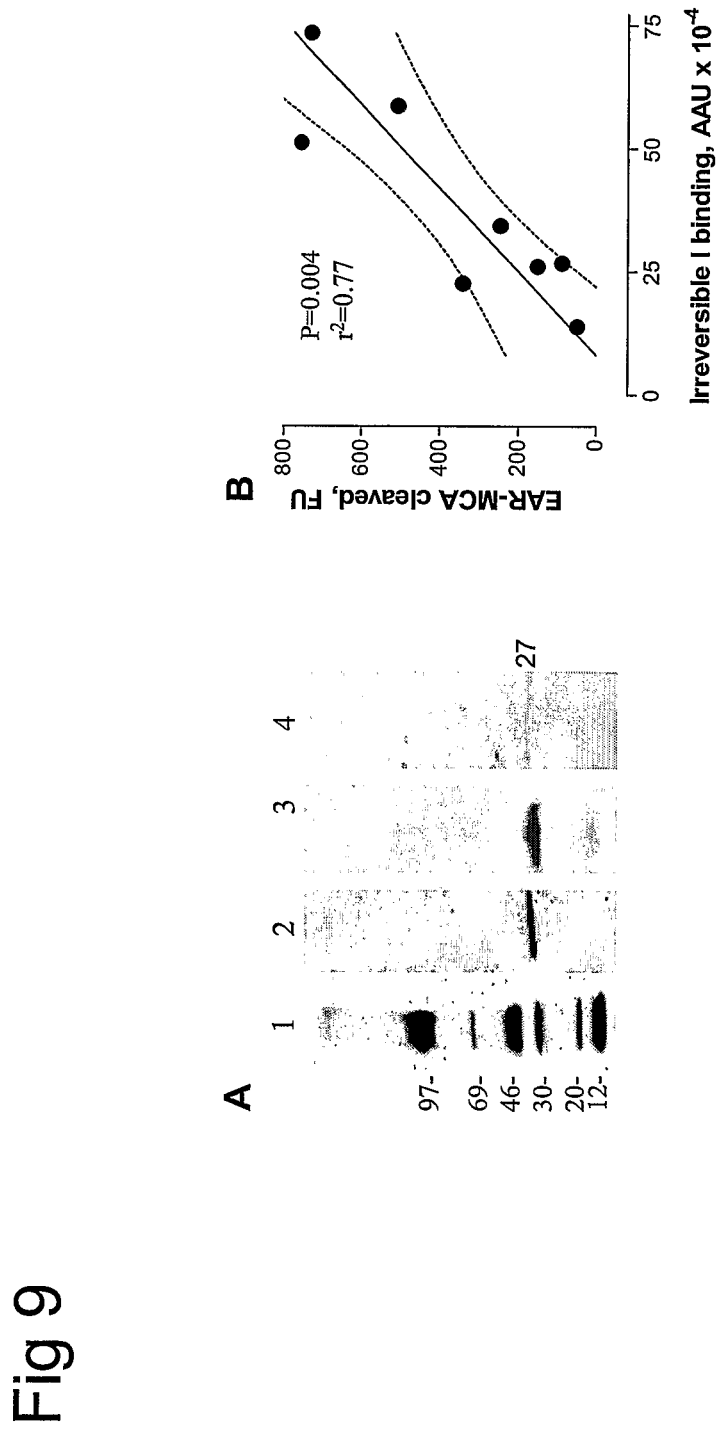

FIG. 9. Single chain Fv reactivity with hapten CAL I (A, B) and correlation with proteolysis (B). A, Reducing SDS-electrophoresis gels showing Fv (clone MMF-4) adducts with hapten CAL I stained with streptavidin-peroxidase (lane 2), anti-c-myc antibody (lane 3) and silver (lane 4). Lane 1, standard proteins used for gel calibration. For the reaction in lane 2, Fv (0.45 µM) treated with hapten CAL I (200 µM; 60 min reaction). The minor c-myc containing band in lane 2 is a degradation product that copurifies with full-length Fv on the nickel column as it contains the his6 tag. B, Shown are values for cleavage of Glu-Ala-Arg-MCA (y-axis; 200 µM; 17 h reaction time) and binding of CAL I (200 µM; 60 min) by purified Fv from eight clones (MM 18, 20, 24, F4, F5, F6, F11, F14). Correlation assessed by linear regression. Dotted lines, 95% confidence limits. FU, fluorescence units. 183 FU, 1 µM aminomethylcoumarin.

Figure 10:
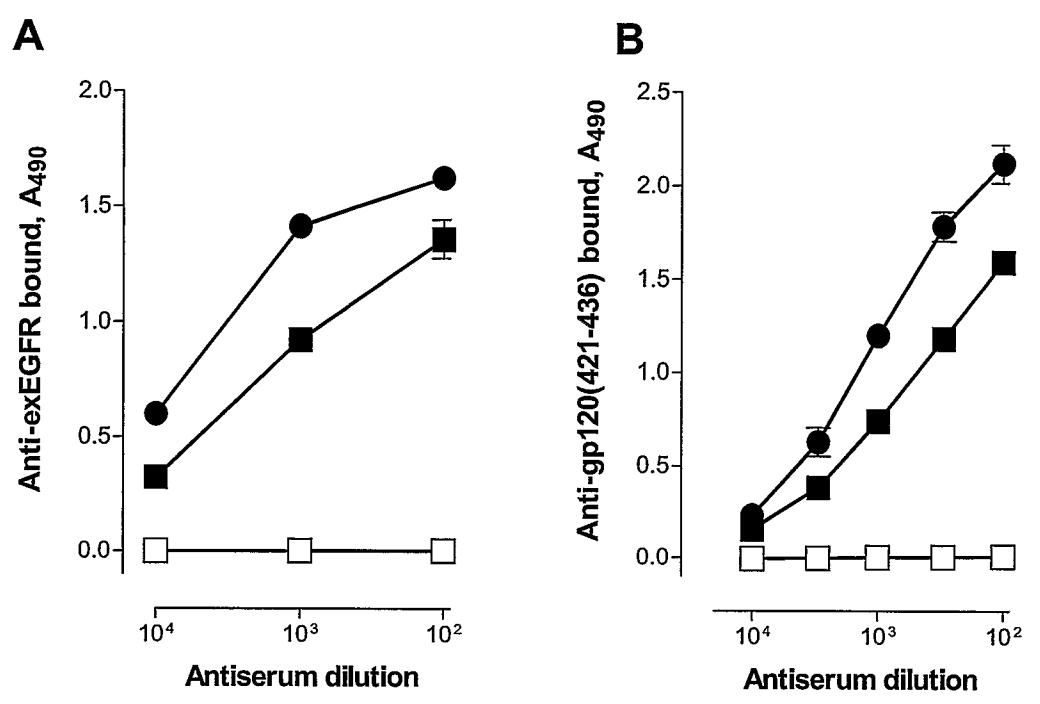

FIG. 10. Antibody binding by phosphonate diester containing protein CAL IV and peptide CAL V determined by conventional ELISA procedures. A, Comparison of binding of immobilized IV by antiserum to exEGFR (■) and control nonimmune serum (□). (●) shows binding of immobilized exEGFR by anti-exEGFR antiserum. B, Comparison of binding of immobilized Va by antiserum to a gp120(421-436)-KLH conjugate (■) and control nonimmune serum (□). (●) shows binding of immobilized gp120(421-436)-BSA conjugate by anti-gp120(421-436) antiserum. No binding of immobilized exEGFR or the gp120(421-436)-BSA conjugate by control nonimmune sera was evident (not shown). Shown are absorbance values (490 nm)±s.d.

Figure 11:
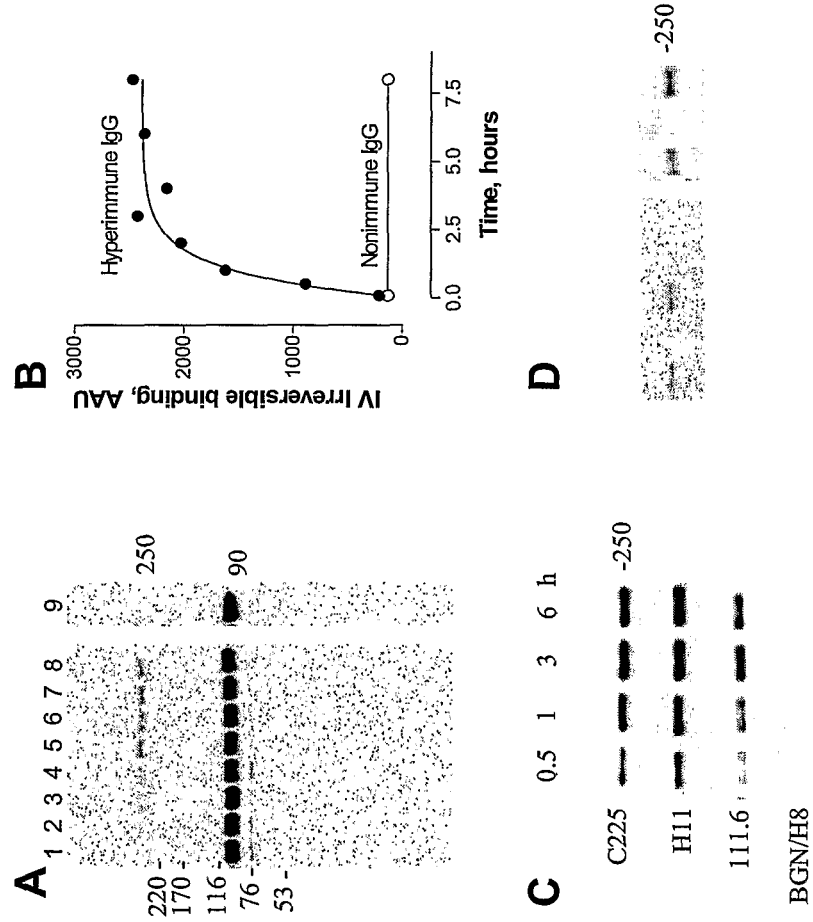

FIG. 11. Specific irreversible binding of exEGFR protein CAL IV by polyclonals and monoclonal Abs to EGFR. A, Streptavidin-peroxidase stained blot showing 250 kD adducts formed by treating IV (0.2 µM) with polyclonal anti-EGFR IgG (0.7 µM) for increasing lengths of time (0.05, 1, 2, 3, 4, 6, and 8 h; lanes 1-8, respectively). Lane 9 is the reaction mixture of IV (0.2 µM) incubated with control nonimmune IgG (0.7 µM) for 8 h. B, Intensities of the 250 kD band from panel A (in arbitrary area units). C, Accumulation of 250 kD biotin-containing adducts of IV (0.2 µM) with monoclonal Abs to EGFR (0.5 µM; clones C225, H11, 111.6) as a function of time. No adducts were formed by an equivalently treated control monoclonal Ab (BGN/H8). D, Biotin-containing 250 kD adducts formed by treatment of IV (0.2 µM) for 2 h with polyclonal IgG to exEGFR (0.5 µM) in the absence (lane 1) and presence of exEGFR (1 µM; lane 2) or calmodulin (1 µM; lane 3). In control reactions, IV (0.2 µM) was treated for 2 h with nonimmune IgG (0.5 µM; lane 4) and boiled polyclonal IgG to exEGFR (10 min at 100° C.; 0.5 µM; lane 5). IVa (0.2 µM) treated with monoclonal IgG c225 (0.5 µM) for 2 h in the absence of exEGFR is shown in lane 6, and in presence of exEGFR (1 µM) or calmodulin (1 µM) in lanes 7 and 8, respectively. Abs treated with competitor proteins for 30 min prior to addition of IV or IVa.

Figure 12:
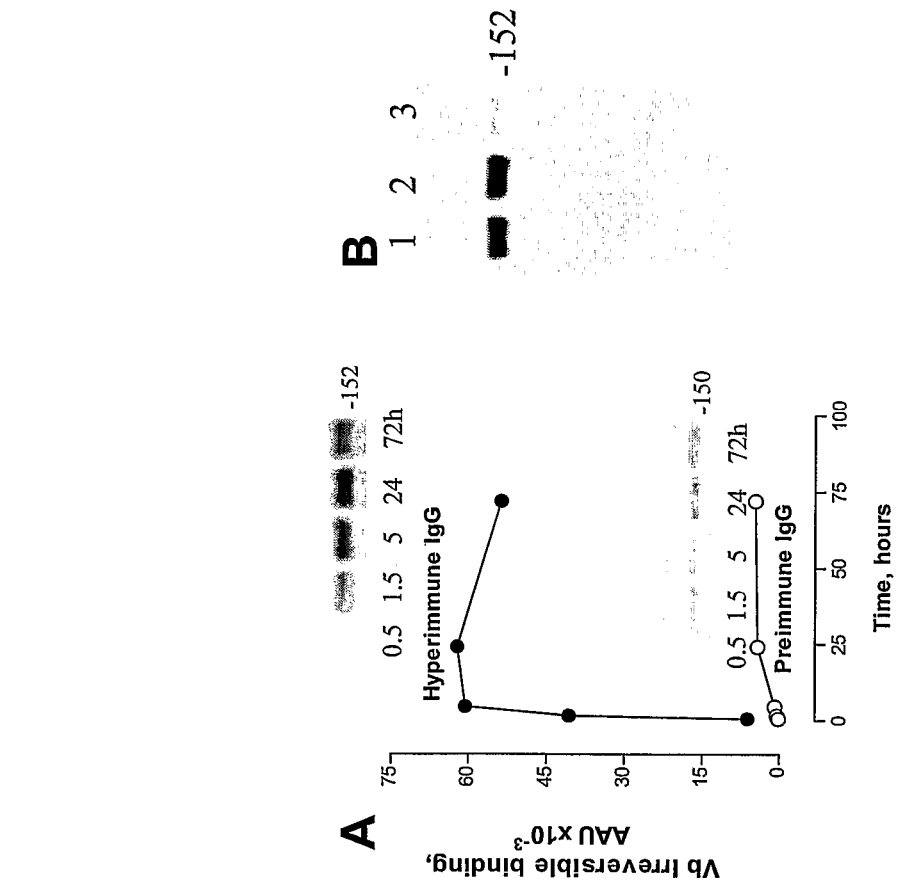

FIG. 12. Specific irreversible binding of peptidyl CAL Va by Abs to gp120(421-436). A, Time course of formation of adducts of Va (10 µM) incubated with IgG to gp120(421-436) (1 µM). Insets, streptavidin-peroxidase stained 152 kD adducts in nonreducing SDS-electrophoresis gels formed with anti-gp120(421-436) IgG (top) and equivalent concentrations of nonimmune IgG (bottom). B, streptavidin-peroxidase stained nonreducing SDS-electrophoresis gels showing Va (10 µM) adducts formed by treatment with anti-gp120 (421-436) IgG (1 µM; 1 h) in the absence of competitor proteins (lane 1) and presence of albumin (3 µM) or gp120 (421-436)-BSA (3 µM BSA equivalents; 30 µM peptide equivalents).

Example 2

Figure 13:
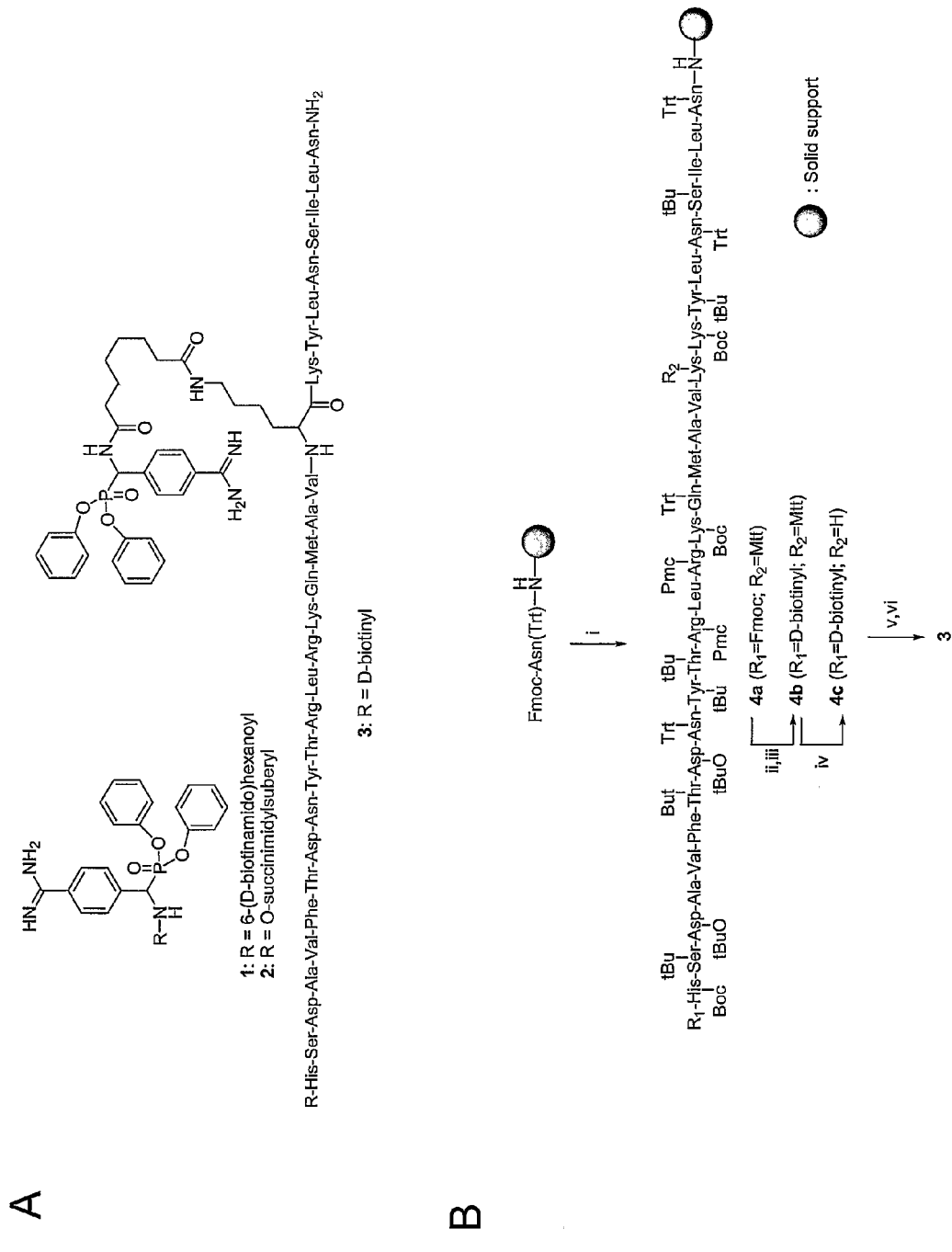

FIG. 13. (A) Structure of hapten CAL 1, VIP-CAL 3 and synthetic intermediate 2. (B) Scheme for synthesis of VIP-CAL 3. Reagents and Conditions for steps i-vi in Panel B: (i) Solid-phase peptide synthesis by 9-fluorenylmethoxycarbonyl chemistry [deprotection, 20% piperidine in DMF (3 min× 2, 20 min×1); coupling, N-(9-fluorenylmethoxycarbonyl) amino acid (2.5 equiv), PyBOP (2.5 equiv), 1-hydroxybenzotriazole (2.5 equiv), N,N-diisopropylethylamine (7.5 equiv) in DMF (60 min)]; (ii) 20% piperidine in DMF (3 min×2, 20 min×1); (iii) D-biotin (2.5 equiv), PyBOP (2.5 equiv), 1-hydroxybenzotriazole (2.5 equiv), N,N-diisopropylethylamine (7.5 equiv) in DMF (60 min); (iv) 1% TFA in $CH_2Cl_2$ (5 min×10); (v) 2 (3 equiv), 0.1 mM N,N-diisopropylethylamine in DMF (overnight); (vi) TFA-ethanedithiol-thioanisole-phenol (90:1:1:8, 2 h). All steps at room temperature. Protecting groups: Boc, tert-butoxycarbonyl; tBu, tert-butyl; Pmc, 2,2,5,7,8-pentamethylchroman-6-sulfonyl; Trt, trityl; Mtt, 4-methyltrityl.

FIG. 14. Specific covalent VIP-CAL binding by monoclonal anti-VIP IgG (clone c23.5). Panel A: Accumulation of VIP-CAL 3 or hapten CAL 1 adducts shown in arbitrary area units (AAU) of the adduct bands determined by electrophoresis and densitometry. Reaction conditions: 1 µM IgG, 10 µM CAL, 37° C. Data are means of closely agreeing duplicates. Correlation coefficients for curves fitted to progress curves by linear regression were 0.9 or greater. All reactions analyzed at 6 time points as shown for anti-VIP L chain. For clarity, only the final data points at 120 min are shown for anti-VIP H chain and control Ab H and L chains (UPC10 IgG). Inset, Streptavidin-peroxidase stained blots of SDS-gels showing 3-adducts of the c23.5 light (29 kD) and heavy (58 kD) chains.

Lanes 1-6 correspond to the reaction time shown in the graph (10, 20, 40, 60, 90, and 120 min). Panel B: Representative plot showing inhibition by VIP (10 μM) of formation of anti-VIP light chain adducts with VIP-CAL 3. % Inhibition determined as: $100-100(V_{app,+VIP})/(V_{app,-VIP})$, where +VIP and −VIP refer to the presence and absence of VIP, respectively. Inset, Streptavidin-peroxidase stained electrophoresis cut-outs showing light chain adducts formed in the absence and presence of VIP. Headers 1 through 6 correspond to the progressively increasing reaction time shown in the graph. Panel C: Streptavidin-peroxidase stained blots of SDS-electrophoresis gels showing CAL binding to anti-VIP Ab in the presence of human plasma (1% volume/volume; 1 h; CALs, 10 μM each; exogenously added Abs, 10 μM). Exogenous Abs and CALs used are: Anti-VIP c23.5 IgG+VIP-CAL 3 (lane 1); Control UPC10 IgG+VIP-CAL 3 (lane 2); VIP-CAL 3 alone (lane 3); Anti-VIP c23.5+hapten 1 (lane 4), UPC10 IgG+hapten 1 (lane 5); and, hapten 1 alone (lane 6). Biotin-containing bands in lanes 1-6 detected as in panel A. Lanes 7 and 8 are silver stained blots of human plasma (1% volume/volume) and molecular-weight standards, respectively. Panel D: Streptavidin-peroxidase stained blots of reducing SDS-electrophoresis gels showing inhibition of VIP-CAL binding to anti-VIP c23.5 light chain by DFP. Anti-VIP IgG c23.5 (1 μM) was incubated with or without DFP (5 mM) for 5 min, and then allowed to react with VIP-CAL 3 (2 μM) for 60 min.

FIG. 15. Inhibition of anti-VIP light chain c23.5 catalyzed Pro-Phe-Arg-AMC hydrolysis by VIP-CAL 3. Panel A: Progress curves of Pro-Phe-Arg-AMC (0.2 mM) cleavage by the light chain (0.8 μM) in the absence (○) and presence (●) of VIP-CAL 3 (3 μM). Curves are least-square-fits to the equation $[AMC]=V \cdot t$ ($r^2$ 0.99) (○) or $[AMC]/[AMC]_{max}=1-e^{-k_{obs} \cdot t}$ ($r^2$ 0.89) (●), where V is the velocity of AMC release; $[AMC]_{max}$, the extrapolated maximum value of AMC release, and $k_{obs}$, the observed first-order rate constant. Data are means of 3 replicates±SD. Fluorescence values expressed as released AMC by comparison with a standard curve constructed using authentic AMC. Background fluorescence in the absence of catalyst corresponded to 0.05±0.03 μM AMC. Panel B: Comparison of VIP-CAL 3 (●) and hapten CAL 1 (○) inhibition of light chain catalyzed Pro-Phe-Arg-AMC hydrolysis. Curves are fitted to the equation: % inhibition=$100/(1+10^{logEC50-log[CAL]})$ where EC50 is the concentration yielding 50% inhibition ($r^2$ 0.98). Reaction conditions as in Panel A except that varying CAL concentrations were employed (1, 3, 10, 30 μM). % inhibition computed as: $100 (V-V_{13})/V$, where $V_{13}$ represents the residual activity after incubation for 13 h (tangents of the least-square-fit progress curves obtained as in Panel A). Values are means of 3 replicates±SD. In the absence of CALs, the reaction rate was 22 nM AMC h$^{-1}$. Panel C: Stoichiometry of antibody light chain (c23.5) reaction with VIP-CAL 3. Shown is the plot of residual catalytic activity (Pro-Phe-Arg-AMC hydrolysis) of the light chain in the presence of varying VIP-CAL 3 concentrations (reaction conditions as in Panel B except that the VIP-CAL concentrations were 0.03, 0.1, 0.3, 1.0 and 3.0 μM, and reaction time was 36 h). Residual activity was determined as 100Vi/V, where V is the velocity in the absence of inhibitor and Vi is a computed value of the velocity under conditions of complete inhibitor consumption. Vi values were obtained from least-square-fits to the equation $[AMC]=Vi \cdot t + A(1-e^{-k_{obs} \cdot t})$, where A and $k_{obs}$ represent, respectively, the computed AMC release in the stage when inhibitor consumption is ongoing and the observed first-order rate constant, respectively ($r^2$ for individual progress curves, >0.97). The equation is valid for reactions with an initial first order phase and a subsequent zero order phase. The X-intercept shown in the plot was determined from the least-square-fit for data points at [VIP-CAL 3]/[light chain] ratio<1. Inset, Example progress curve from which Vi values were computed. VIP-CAL 3, 0.03 μM.

FIG. 16. Inhibition of polyclonal antibody catalyzed VIP cleavage by VIP-CAL 3 and hapten CAL 1. Panel A: Reversed-phase HPLC profiles showing cleavage of $[Tyr^{10}-^{125}I]$-VIP at multiple sites by human IgG HS-2. $[Tyr^{10}-^{125}I]$-VIP incubated in the presence (●) or absence (○) of HS-2 IgG (2 μM) for 16 h and subjected to HPLC [Nova-pak $C_{18}$ 3.9×150 mm; 0.1% TFA in water:0.1% TFA in 80% acetonitrile 95:5 for 10 min, 95:5 to 30:70 in 55 min, 30:70 to 0:100 in 5 min, 0:100 for 5 min (0.5 ml/min)]. Shown are values of $^{125}I$ radioactivity recovered in the HPLC fractions (0.5 ml). Panel B: Irreversible inhibition of HS-2 IgG-catalyzed $[Tyr^{10}-^{125}I]$-VIP cleavage by VIP-CAL 3 and hapten CAL 1. IgG (2 μM) was preincubated for 16 h in the absence or presence of increasing concentrations of VIP-CAL 3 (●) or hapten CAL 1 (○). Following removal of unreacted CAL by chromatography on immobilized Protein G, the residual catalytic activity of the IgG was measured using $[Tyr^{10}-^{125}I]$-VIP as substrate. Data are means±SD. Control HS-2 IgG incubated in the absence of CALs cleaved 2791 c.p.m. $[Tyr^{10}-^{125}I]$-VIP.

Example 3

FIG. 17: DNA-CALs 1-3. Schematic representation of DNA-CAL from psoralen-DNA interstrand cross-linking adduct. Panel A: The large DNA-CAL in is prepared by photochemical reaction of DNA with 4'-aminomethyl-4,5',8-trimethylpsoralen (AMT) followed by acylation of the amino group of AMT using a pre-activated CAL derivative (inset of Panel B). Upon UV irradiation (365 nm), AMT forms covalent nucleic acid adducts through photochemical addition. The primary reaction is cyclobutane ring formation between the 5,6 double bond of thymidine in DNA and either the 4',5' or 3,4 double bond of the psoralen. Reaction at the 4',5' double bond (arrow a) results in a furan-side monoadduct, which can further react at a site with a flanking pyrimidine on the opposite strand (arrow b) to form an interstrand cross-link (Panel B). The CAL moiety is introduced to the amino group of AMT (arrow c). Extensive modification might disrupt the DNA structure. Thus reaction conditions are optimized to give CAL-DNA adduct with approximate CAL/nucleotide molar ratio of 1:100. The amount of psoralen incorporated is determined by measuring primary amino groups using fluorescamine or analogous reagents. CAL incorporated is determined by measuring the primary amine consumed in the same manner. Abbreviations: AMT, 4'-aminomethyl-4,5',8-trimethylpsoralen; T, 3'-deoxythymidine monophosphate. Panel C: shows the backbone modified oligoDNA-CAL. Phosphate diester linkage of DNA are partially modified to phosphate triester or fluorophosphate moiety, of which susceptibility to nucleophiles is held to be comparable with diphenyl phosphonate and diisopropyl fluorophosphate. Arrows in Panel B indicate potential leaving groups. (i) The precursor, H-phosphonate DNA analog, is an intermediate in conventional solid-phase DNA synthesis by H-phosphonate method. (ii: phosphate triester type) After removal of base protecting group and solid support with aqueous ammonia, the backbone H-phosphonate functionalities are partially converted to 4-nitrophenyl phosphonate by using a limited amount of 4-nitrophenol. The unreacted H-phosphonate groups are oxidized with iodine, as in the conventional DNA synthesis, to give phosphate diester linkage (original DNA backbone structure). (iii) After solid-phase synthesis, the product is oxidized with iodine as in the usual DNA synthesis and treated with aqueous ammonia. The oligo-DNA obtained is treated with a limited amount of KF in the presence of 18-crown-6 and thionyl chloride to covert, in part, the phosphate diester to fluorophosphate. Chain length will be about bases. Substitution at backbone phosphate may result in considerable disruption of high-order structure of DNA. Thus the reaction conditions are optimized to give oligoDNA-CAL with approximate modified/unmodified phosphate molar ratio of 1:5. The average modified/unmodified ratio is determined by photometric measurement of 4-nitrophenol after hydrolysis with aqueous sodium hydroxide and by quantification of fluorine by elemental analysis. References: For psoralen-DNA adduct structures: (1) Straub, K.; Kanne, D.; Hearst, J. E.; Rapoport, H. Isolation and characterization of pyrimidine-psoralen photoadducts from DNA. J. Am. Chem. Soc. 1981, 103, 2347-2355. (2) Kanne, D.; Straub, K.; Rapoport, H.; Hearst, J. E. Psoralen-deoxyribonucleic acid photoreaction. Characterization of the monoaddition products from 8-methoxypsoralen and 4,5′,8-trimethylpsoralen. Biochemistry 1982, 21, 861-871. (3) Straub, K.; Kanne, D.; Hearst, J. E.; Rapoport, H. Isolation and characterization of pyrimidine-psoralen-pyrimidine photoadducts from DNA. J. Am. Chem. Soc. 1982, 104, 6754-6764. For DNA synthesis by H-phosphonate method: Froehler, B. C.; Ng, P. G.; Matteucci, M. D. Synthesis of DNA via deoxynucleoside H-phosphonate intermediates. Nucleic Acids Research 1986, 14, 5399-5407.

Figure 18:
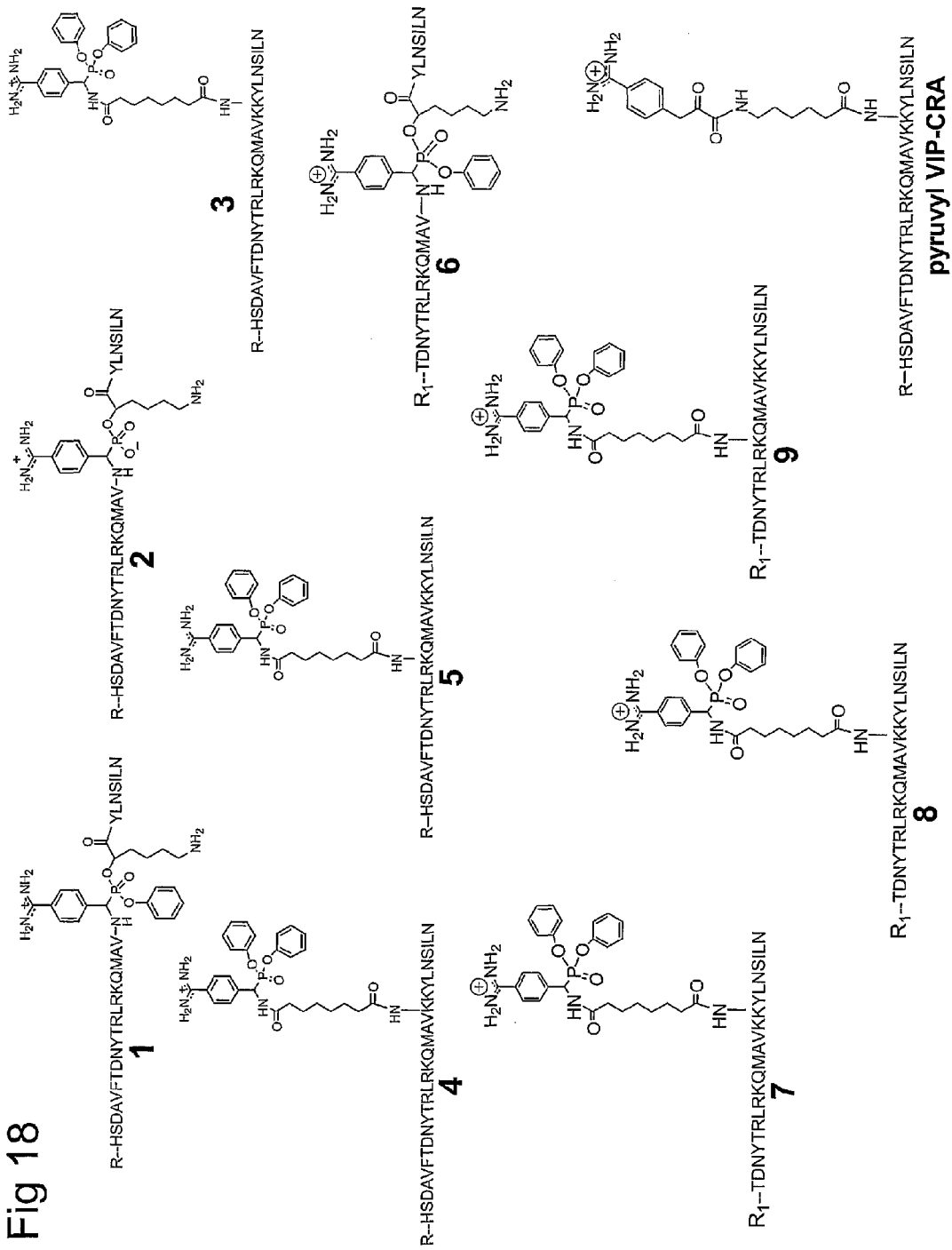

FIG. 18: VIP-CALs 1-9.

Figure 19:
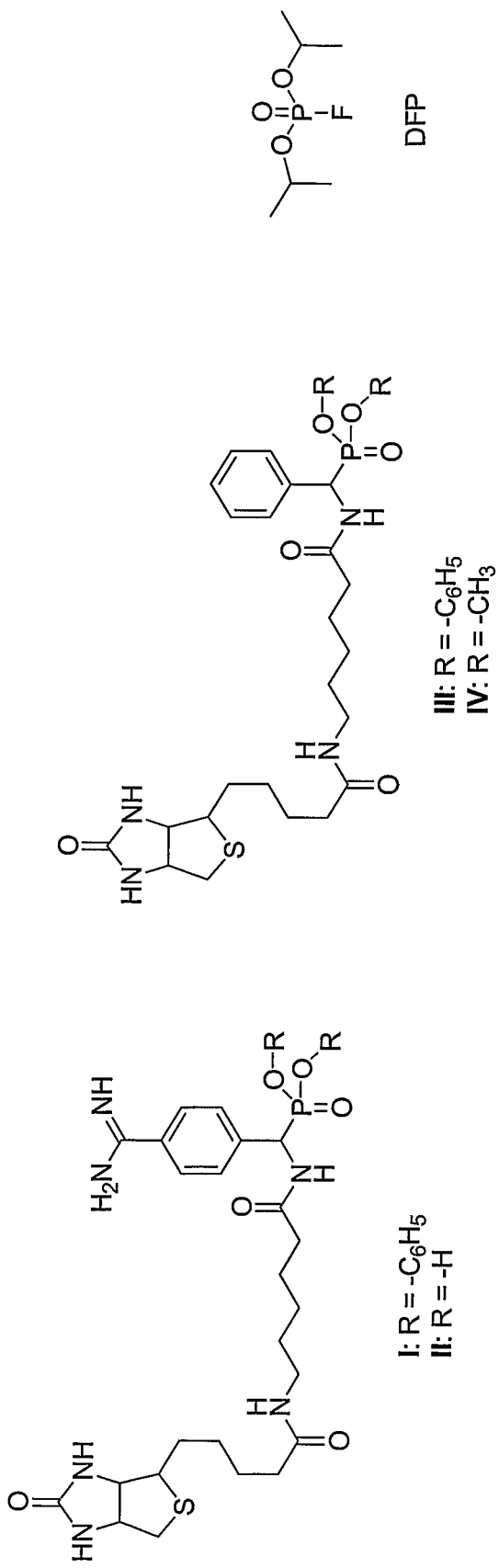

FIG. 19. Compounds I-IV, diisopropyl fluorophosphates (DFP). Hapten CAL I is an active site-directed inhibitor of trypsin-like enzymes. Compound II is the unesterified phosphonic acid analog of I devoid of covalent reactivity. III and IV are I-derivatives devoid of the side chain amidino function and contain a weaker leaving group, respectively. These structures are analogs of the irreversible serine protease inhibitor DFP.

FIG. 20. Hapten CAL I reactivity with spleen cells. A, Flow cytometry of murine splenocytes (naïve BALB/c mouse) stained with biotinylated hapten CAL I (grey line) and compound II (black line; both compounds 100 μM, 4 hours; streptavidin-FITC (50 μg/ml). Twenty five thousand cells counted. B, Anti-CD19 Ab staining (grey line; phycoerythrin conjugate) of hapten CAL I labeled cells; streptavidin-FITC 1 μg/ml). (black line) shows staining with the phycoerythrin conjugate of the isotype matched control antibody. C-F, Deconvoluted (5 iterations) fluorescence acquisitions showing two B cells labeled with CAL I (streptavidin-FITC, 1 μg/ml, panel C) and phycoerythrin conjugated anti-CD19 Ab (panel D). E shows a merged rendition of the FITC and phycoerythrin probes. F is a 3D wire frame model of the FITC emission patterns compiled from 30 individual sections and then subjected to split screen extraction. Blue counterstain, 4',6-diamidino-2-phenylindole.

FIG. 21. Immunochemical identification of hapten CAL I labeled Ig subunits in B cell extracts. A, SDS-gel electrophoresis lanes showing extract of B cells labelled with hapten CAL I (100 μM, 4 hours) following staining with silver (lane 1) and peroxidase conjugated streptavidin (lane 2). Migration of marker proteins shown on left. B, SDS-gel immunoblots of hapten CAL I labeled B cell extract stained with Abs to μ (lane 3), λ (lane 4), κ (lane 5) and γ (lane 6) chains. C, Streptavidin-peroxidase stained SDS-gels showing hapten CAL I labeled proteins recovered by affinity chromatograpy, of splenocyte extract on immobilized anti-μ (lane 7), anti-κ/λ (lane 8) and anti-γ Abs (lane 9).

Example IV

FIG. 22: Schematic structure of Factor VIII-CAL. The electrophilic phosphonate diester is linked to lysine side chains.

Example V

FIG. 23: Irreversible hapten CAL 1 (solid bars) and hapten CAL 2 binding (hatched bars) by non-enzymatic proteins. The proteins (1 μM) were incubated with the CAL (0.5 mM) in 10 mM PBS (pH 7.4) containing 1 mM CHAPS and 5% DMF at 37° C. (16 h) and subjected to SDS gel electrophoresis. Protein adducts of hapten CAL 1 and 2 were measured by densitometry of streptavidin-HRP stained blots of the SDS gels. Band intensities are expressed in arbitrary area units (AAU) corrected using biotinylated BSA included in each gel as a reference. Abbreviations: TRY, trypsin; SBTI, soybean trypsin inhibitor; BAL, bovine α-lactalbumin; OVA, ovalbumin; exEGFR, extracellular domain of epidermal growth factor receptor; HSA, human serum albumin; CaM, calmodulin.

FIG. 24: Irreversible hapten CAL 1 binding by gp120. (A) Time course of irreversible hapten CAL 1-binding. gp120 (MN strain, 1 μM) was incubated with 1 (0.5 mM) in 10 mM phosphate buffered saline (pH 7.4) at 37° C. for 15, 45, 90, 180, and 240 min, and 1-gp120 adduct bands were detected in the same manner as FIG. 23. The curve shown is the least-square-fit ($r^2$=0.98) for the first-order rate equation [$B/Bmax=1-e^{-kobs\cdot t}$; B, observed band intensity (AAU); Bmax, extrapolative maximum value of B (AAU); kobs, the pseudo-first-order rate constant; t, incubation time]. Inset, Streptavidin-peroxidase stained blot of SDS gel showing accumulation of 1-gp120 adducts after incubation for 15 (lane 1), 45 (lane 2), 90 (lane 3), 180 (lane 4), and 240 min (lane 5). (B) pH-dependency of kobs for irreversible 1-gp120 binding. gp120 (1 μM) incubated with 1 (0.1 mM) at 37° C. for 30, 60, 120, 180, 240, and 360 min in 50 mM acetic acid-50 mM MES-50 mM Tris (pH 3.9, 5.0, 6.0, 7.0, 8.0, 9.0) was subjected to SDS-electrophoresis. The kobs value at each pH was obtained as described in (A). The apparent pKa of the reactive site was computed as 7.31±0.08 from the least-square-fit (r2, >0.99) for the following equation: kobs=kobs (max)/$(1+10^{pKa-pH})$, where kobs(max) represents the extrapolative maximum value of kobs. (C) Kinetic parameters for irreversible 1-gp120 binding. Irreversible 1-binding by gp120 was analyzed in the same manner as in (A) using 0.05, 0.1, 0.2, 0.3, and 0.5 mM of 1. The kobs value at each 1 concentration was extracted from least-square-fitted progress curves ($r^2$, 0.93-0.99) as in (A). Dissociation constant of non-covalent 1-gp120 complex (Kd) and the first-order rate constant of covalent adduct formation from the noncovalent complex (k3) was computed from the least-square-fit of the kobs vs [1] plot ($r^2$, 0.96) to the equation, kobs=k2·[1]/(Kd+[1]).

FIG. 25: Irreversible hapten CAL 1 binding by trysin (Panel A) and IgG c23.5 (Panel B) pre-heated at varying temperatures. The proteins (1 μM) in 10 mM PBS (pH 7.4) containing 1 mM CHAPS were treated at 37, 50, 65, 80, and 100° C. for 30 min. The solutions were kept in an ice bath for 15 min, and then at 37° C. for 30 min. Pre-heated proteins (1 μM) was incubated with 1 (0.5 mM) in 10 mM PBS (pH 7.4) containing 5% DMF at 37° C. for 2 h. 1-bound proteins were measured in the same manner as FIG. 23. Data are expressed as % of 1-protein adduct band intensity relative to the protein treated at 37° C. Insets, Streptavidin-peroxidase stained blot of SDS gel showing 1-protein adducts (two independent reactions at each temperature). As the electrophoresis of the IgG reaction mixture was conducted under reducing conditions, separate 1-adducts of H chain (upper panel) and L chain (lower panel) (two independent reactions at each temperature).

FIG. 26: Irreversible binding of calmodulin with Bt-VIP-CAL. (A) Structure of Bt-VIP-CAL 3. (B) Kinetics of hapten CAL 1 and Bt-VIP-CAL 3 binding by calmodulin. Calmodulin (1 μM) was incubated with 3 (10 μM) or 1 (0.5 mM) in 60 mM HEPES (pH 7.3) containing 1 mM CHAPS, 1 mM CaCl2, 150 mM NaCl, 5% DMSO (for 3) or DMF (for 1) for 1, 2, 4, 8, 19 h at 37° C. The reaction mixtures were subjected to SDS gel electrophoresis and covalent adducts were measured in the same manner as described in FIG. 23. B and Bmax represent, respectively, the band intensity at a given incubation time and the extrapolative maximum value of B. The curve shown is the least-square-fit to the pseudo-first-order equation, $B/Bmax=1-e^{-kobs \cdot t}$ (kobs, the pseudo-first-order rate constant). The second-order rate constants of calmodulin-3 and -1 were 567±77 $M^{-1}$ $min^{-1}$ and 0.212±0.017 $M^{-1}$ $min^{-1}$, respectively. Inset, Streptavidin-peroxidase stained blot of SDS gel showing accumulation of 3-calmodulin adduct. (C) Inhibition of 3-calmodulin binding by VIP. Calmodulin (1 μM) was incubated with 3 (10 μM) in the presence and absence of VIP (100 μM) at 37° C. for 10, 20, and 30 min. % Inhibition by VIP under these conditions were determined from the apparent initial binding velocity in the absence ($V_{app}^-$) and presence ($V_{app}^+$) of VIP: % Inhibition=100(1−Vapp+/Vapp−)=65%.

Example VI

Figure 27:
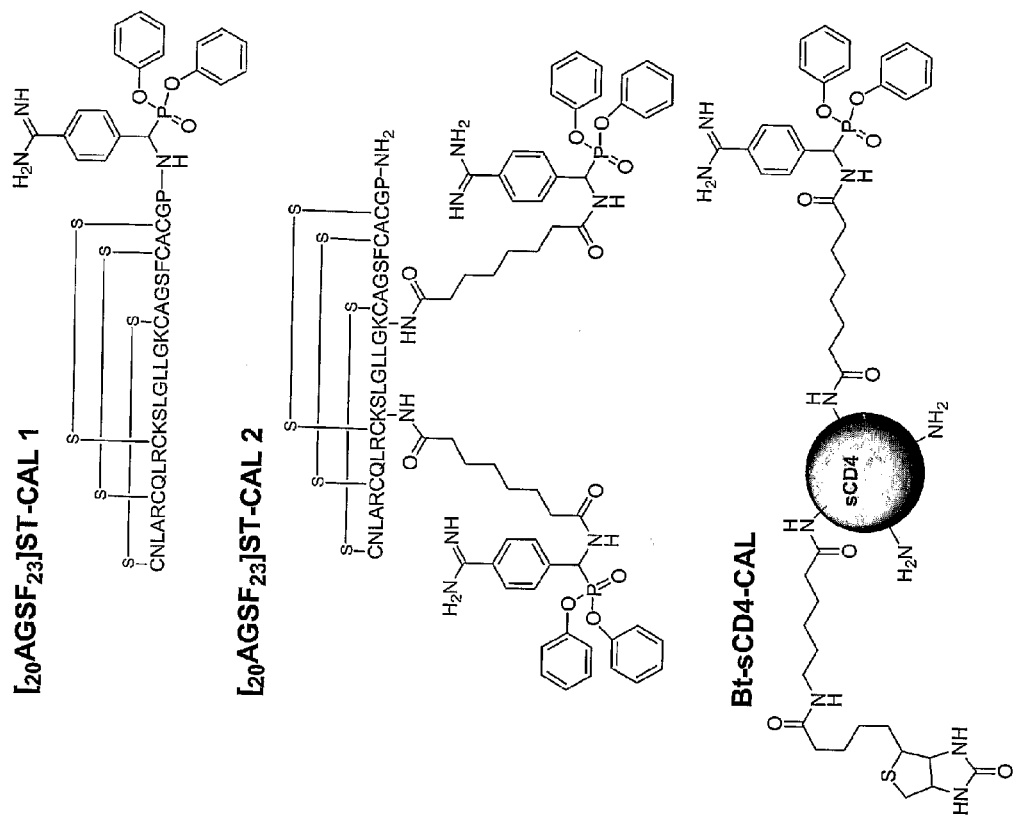

FIG. 27: Schematic structure of peptidyl and proteinic CD4-CALs.

Figure 28:
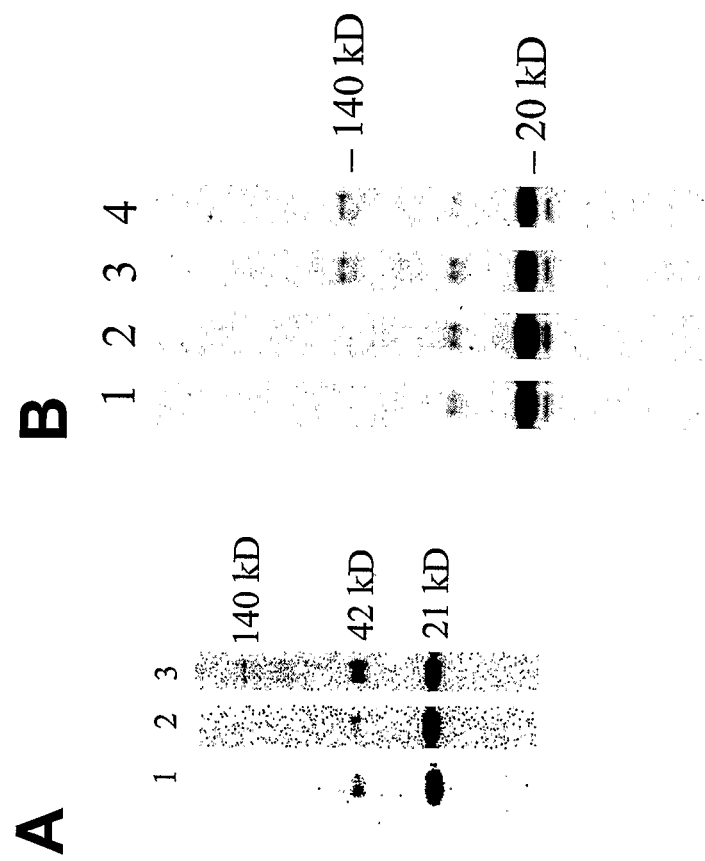

FIG. 28: Irreversible binding of sCD4-CAL with gp120. (A) Streptavidin-peroxidase stained blots of SDS-gels showing Bt-sCD4-CAL (0.1 μM) incubated for 2 h with gp120 (lane 3, 5 μM), bovine serum albumin (lane 2, 5 μM) or diluent (lane 1). Bt-sCD4-CAL contains 5 moles phosphonate diester and 1 mole biotin/mole sCD4 (residues 1-183). The biotinylated sCD4-CAL containing complex at 140 kD locates at the expected mass of the covalent gp120:CD4-CAL complex. The band at 21 kD is the CD4-CAL monomer and the band at 42 kD is consistent with the expected position of CD4-CAL dimers present in the starting material. (B) Inhibition of 140 kD gp120:sCD4-CAL complex formation by sCD4. Shown are streptavidin-peroxidase stained blots of SDS-gels of Bt-sCD4-CAL (0.1 μM) incubated for 8 h with gp120 (5 μM) in the presence of sCD4 (lane 2, 5 μM) or soybean trypsin inhibitor (lane 3, 5 μM), and in the absence of competitor (lane 4). Lane 1 shows the control incubation of sCD4 (5 μM) and Bt-sCD4-CAL (0.1 μM) in the absence of gp120.

Example VII

Figure 29:
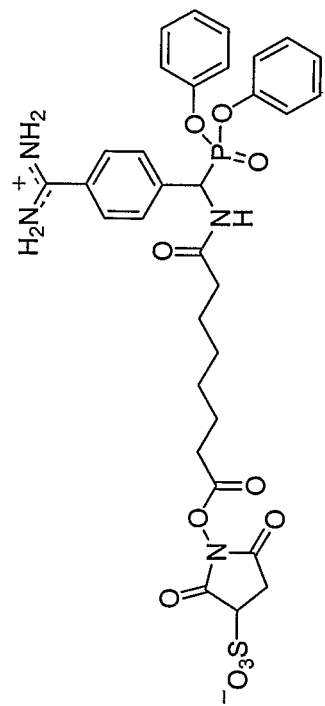

FIG. 29: Acylating Agent Used for gp120-CAL Preparation.

Figure 30:
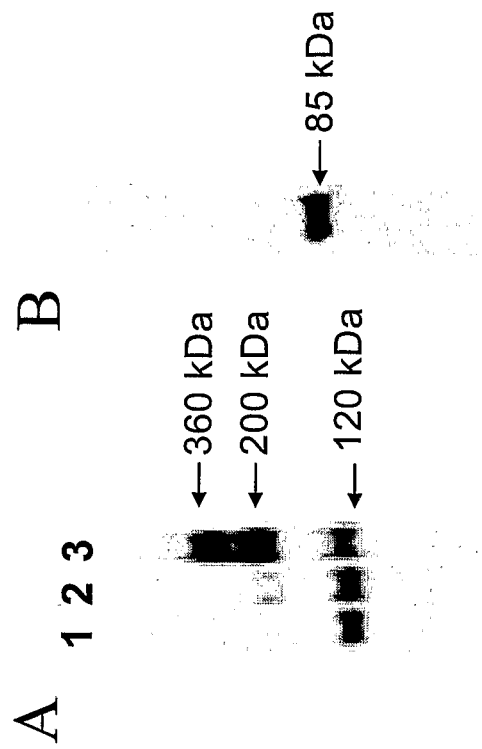

FIG. 30: Covalent trimerization of gp120-CAL. (A) Streptavidin-peroxidase stained blots of SDS-gels showing formation of oligomers in Bt-gp120-CALs containing various numbers of phosphonate groups per molecule of the protein. Lane 1, 4.4; lane 2, 14.2; lane 3, 23.4 mol phosphonate/mol gp120. Bt-gp120-CAL preparations were incubated for 4 h at 37° C. in a neutral pH buffer. (B) A streptavidin-peroxidase stained blot of SDS-gel showing no oligomerization of exEGFR-CAL treated as in A. Phosphonate/exEGFR ratio was 27.9 mol/mol.

Figure 24:
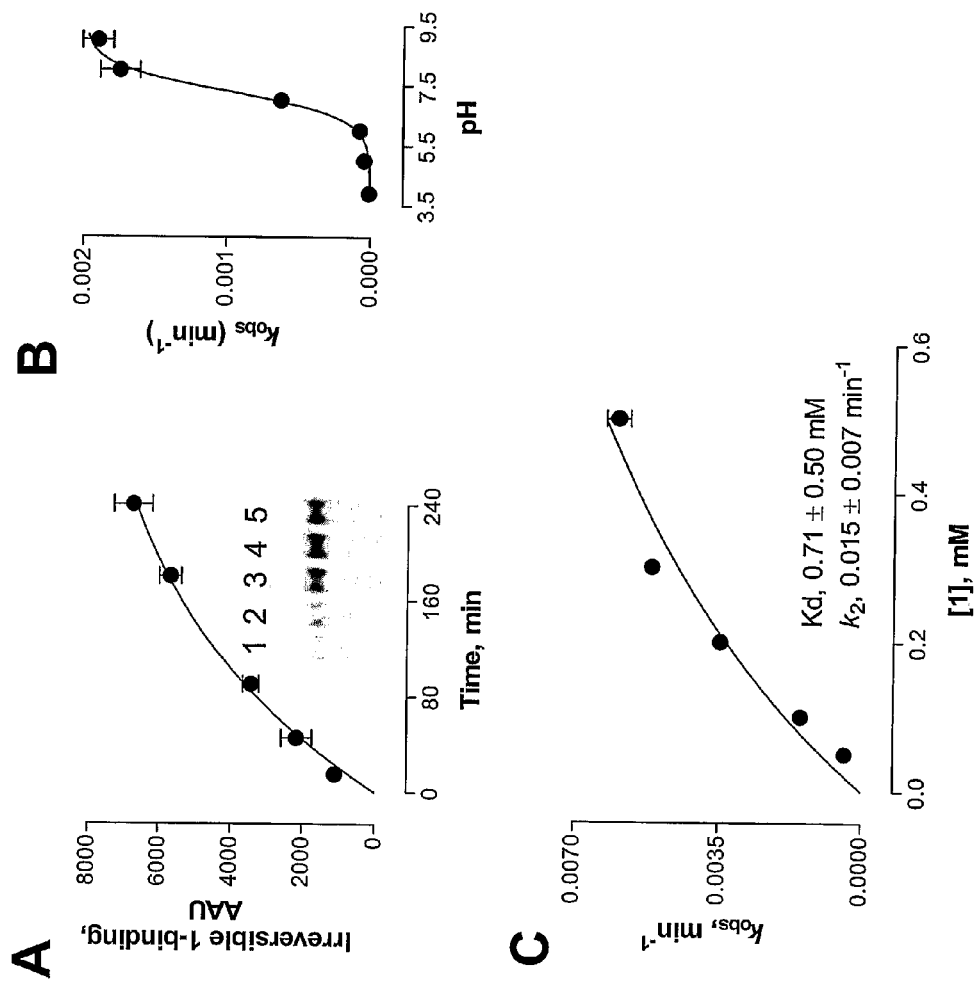
Figure 31:
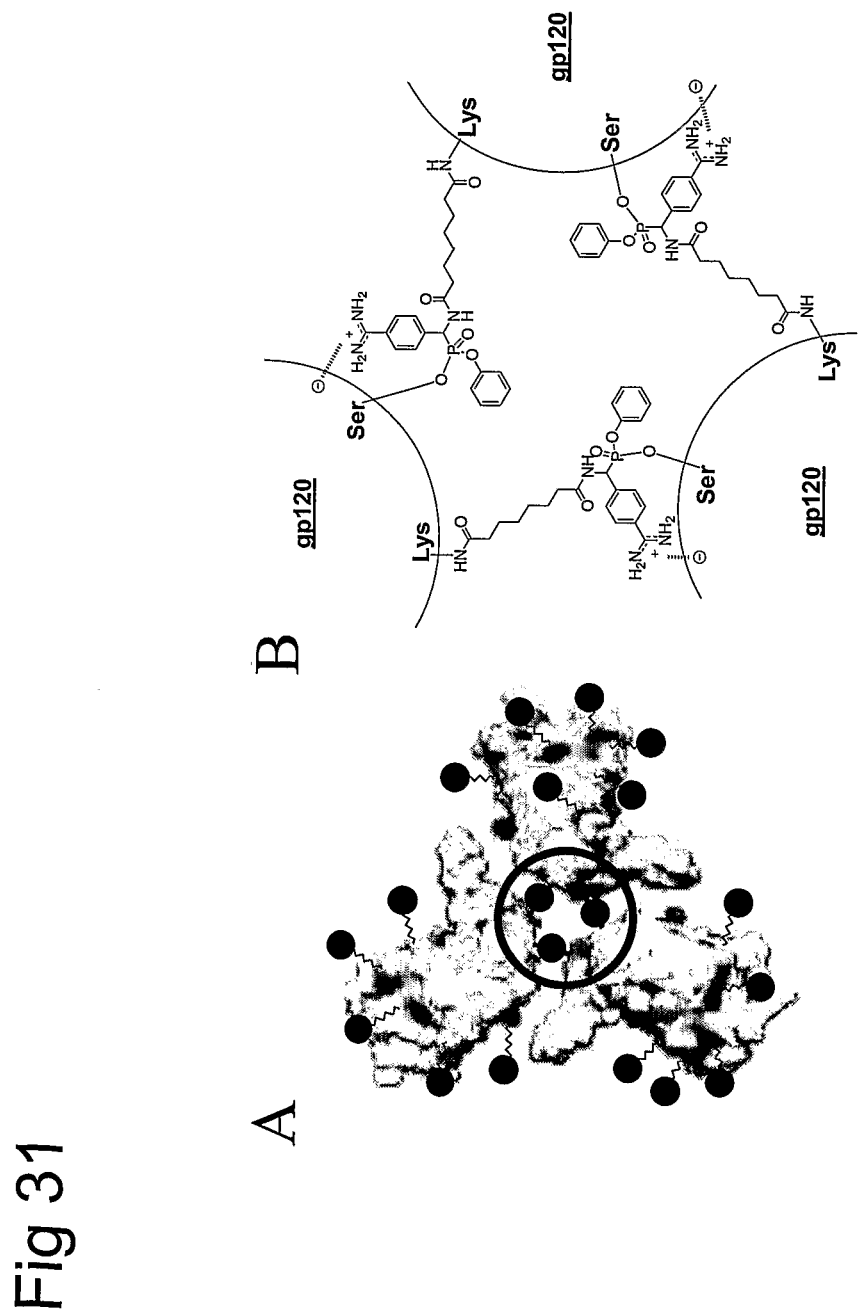

FIG. 31: Possible structures of gp120-CAL trimer (A) and its intersubunit linkage (B). The phosphonate diester moiety of a gp120-CAL molecule forms a covalent bond with the nucleophileic site of another gp120 molecule. The near neutral pKa of the nucleophilic site of gp120 (FIG. 24) suggests the potential involvement of a Ser or a Thr as the nucleophile.

Figure 32:
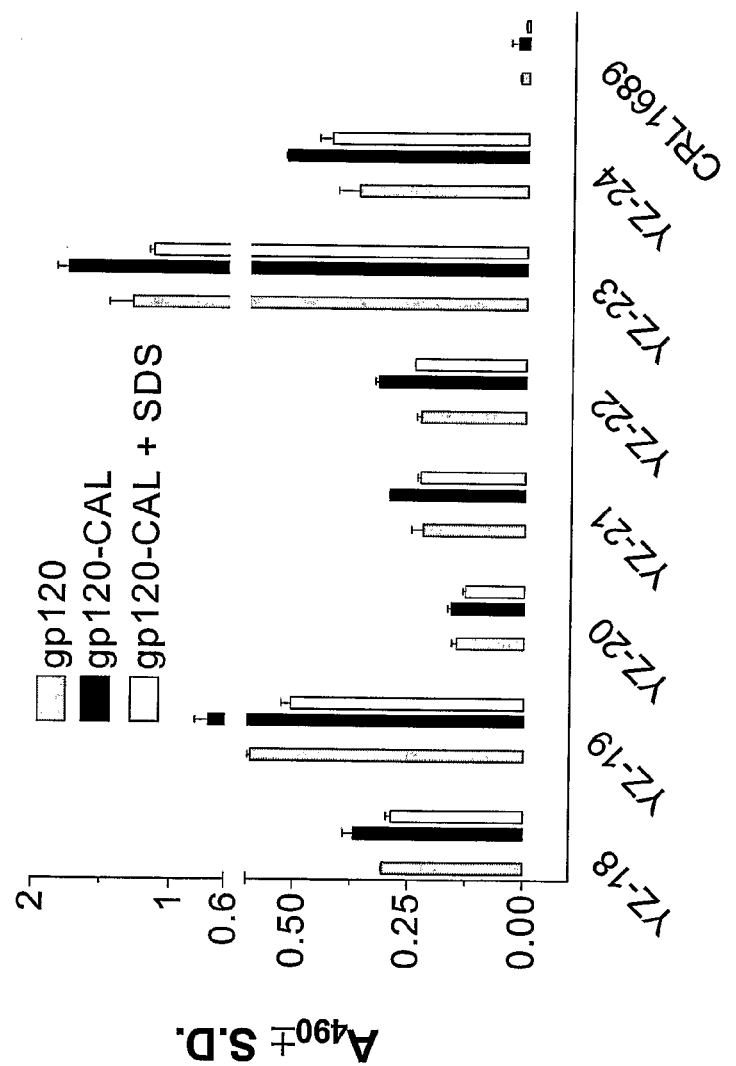

FIG. 32: gp120-CAL and gp120 binding by monoclonal anti-gp120-CAL Abs. ELISA showing gp120-CAL and gp120 binding by tissue culture supernatants containing monoclonal Abs raised by immunization with gp120-CAL (YZ series). Monoclonal Ab CRL1689 is an irrelevant monoclonal IgG with same isotype as YZ21 and YZ23. SDS-resistant gp120-CAL binding indicated by bars and curve labeled gp120-CAL+SDS.

Figure 33:
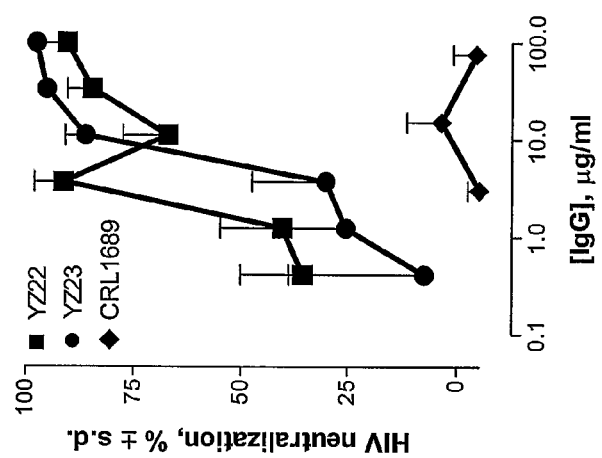

FIG. 33: Concentration-dependent HIV-1 neutralization by monoclonal IgG raised by immunization with gp120-CAL. PBMC infected with primary HIV-1 isolates ZA009. Electrophoretically pure IgG was used for assay. Equivalently purified irrelevant control Abs are: isotype-matched CRL1689. IgG b12 was used as a positive control (IC50 was 25 μg/ml). Neutralization determined by measuring p24 levels. Values are means of 4 replicates.

DESCRIPTION OF THE INVENTION

1. Antibody Nucleophilic Reactivity.

Protein nucleophilic reactivities arise from activation of certain amino acid side chains. In serine proteases, precise spatial positioning of the Ser-His-Asp triad allows formation of a hydrogen bonded network that imparts nucleophilic reactivity to the Ser oxygen. Abs were predicted in 1973 to express enzyme-like active sites based on sequence homology between CDR1 of Bence Jones proteins and the peptide region surrounding the active site Ser residue of serine proteases (1). A serine protease-like catalytic triad composed of Ser27a-His93-Asp1 has been identified in the light chain (L chain) of an antibody (Ab) to VIP by site-directed mutagenesis (2).

Figure 1:
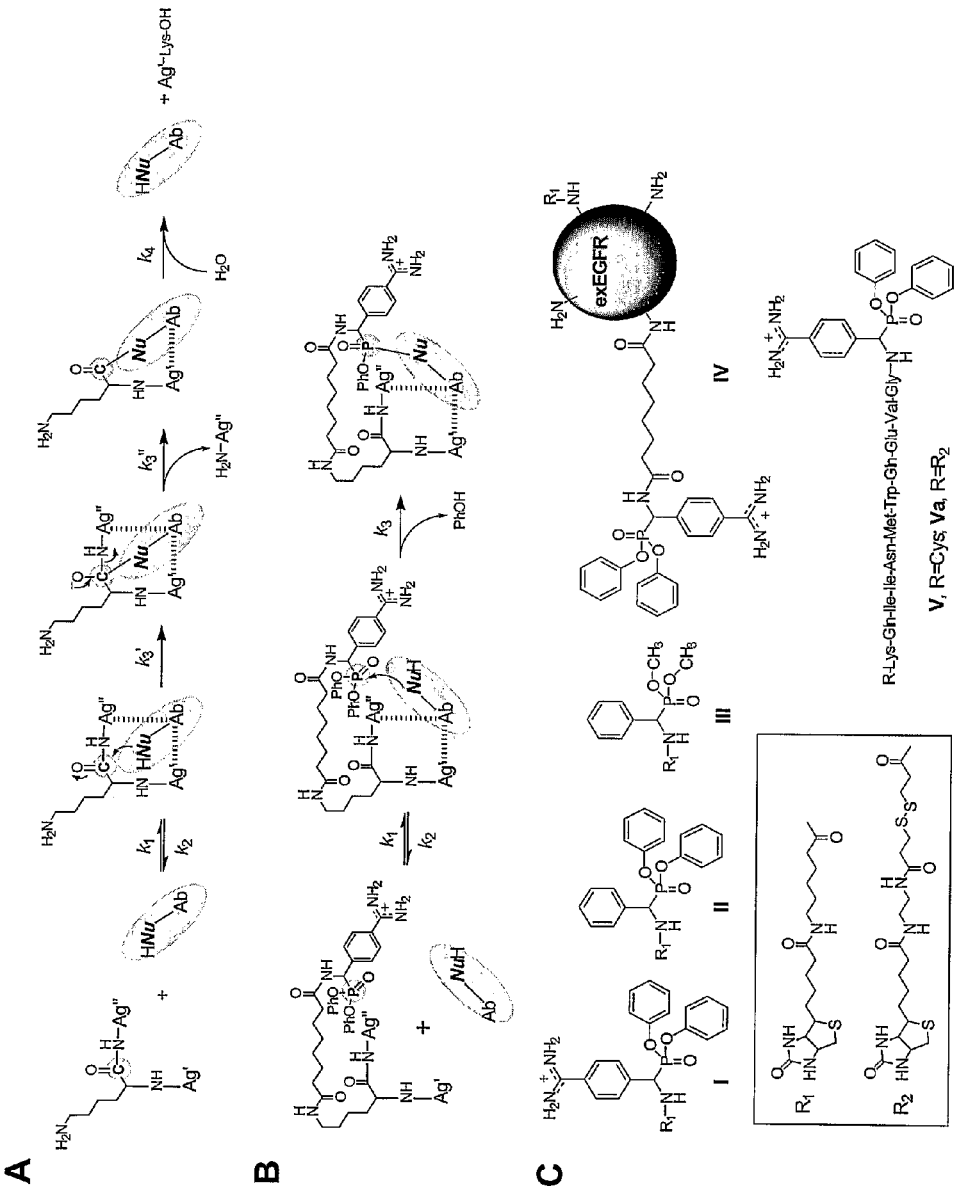
FIG. 1. Panels A and B, Reaction of serine protease-like Abs with antigens and phosphonate diester-containing antigen analogs, respectively. Panel C, CAL structures. In panel A, Nu denotes a nucleophile; Ag' and Ag" are components of the antigenic epitope at which noncovalent contact with the Ab occurs; Ag'-Lys-OH is the N-terminal antigen fragment; and NH2-Ag" is the C-terminal antigen fragment. The active site nucleophile attacks the carbonyl carbon of the scissile bond in the antigen (substrate) to form the tetrahedral transition-state complex. The C-terminal antigen fragment is released and the acyl-Ab complex is formed. Hydrolysis of the acyl-Ab complex results in release of the N-terminal antigen fragment and regeneration of the catalytic Ab. The catalytic rate constant kcat is the sum of k3'+k3". In panel B, the Ab nucleophile attacks the electrophilic phosphonate diester (instead of the carbonyl group) and the phosphonate-containing antigen (CAL) recapitulates the remaining interactions in the ground and transition state Ab-Ag complex (noncovalent binding at peptide epitopes), but unlike the acyl-Ab intermediate, the phosphonyl-Ab adduct is a stable product. In panel C, I is an active site-directed inhibitor of trypsin-like enzymes. II and III are I-derivatives devoid of the side chain amidino function and containing a weaker leaving group, respectively. IV and V are intended, respectively, to permit detection of nucleophiles in specific Abs to exEGFR and residues 421-432 of gp120. The biotin and phosphonate diester groups were incorporated in IV at Lys side chains. Va contains biotin at the N terminus and the phosphonate diester at the C terminus.

The covalent reactivity is a necessary but not sufficient condition for serine protease catalysis. This is because completion of the catalytic cycle requires facilitation of events occurring after formation of the covalent acyl-enzyme intermediate, i.e., hydrolysis of the intermediate and release of product peptides (FIG. 1). Thus proteins can express nucleophilic reactivity despite the absence of catalytic activity. Recent studies indicate that a large proportion if not all Abs express nucleophilic reactivity at levels greater than conventional enzymes (3). These Abs were identified using covalently activated ligands, designated CALs. These CALs contained an electrophilic phosphorus atom that forms a stable covalent bond with activated nucleophiles. Previous studies have indicated that the nucleophilic activity is a heritable trait, encoded by germline V domains (2,4). [About 50 $V_H$ and 50 $V_L$ genes along with a smaller number of diversity and joining genes constitute the inherited Ab repertoire.]. Because the nucleophilic reactivity is germline-encoded, in principle, the immune system should be capable of mounting nucleophilic Ab responses to any polypeptide antigen.

We have found that IgG preparations can display stronger nucleophilic reactivity than trypsin, as determined from rates of formation of covalent adducts with hapten phosphonate diesters of the present invention. Studies of polyclonal IgG and individual single chain Fv (scFv) clones indicate that an evidently universal nucleophilic reactivity in Abs. Perturbations in the level of nucleophilic reactivity are evident when the Abs were subjected to heat treatments, consistent with the idea that activation of the nucleophile depends on the native conformation of the protein.

Figure 2:
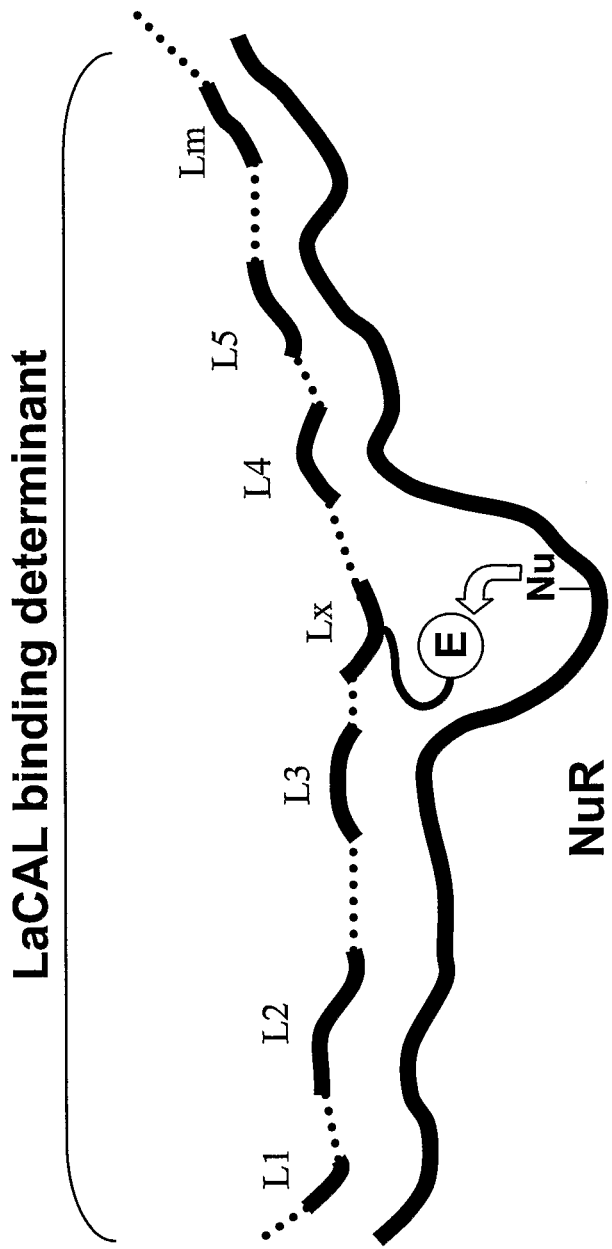
FIG. 2: Schematic representation of the interaction between nucleophilic receptors (NuRs) and large covalent analogs of ligands (LaCALs). The unit structure of LaCALs can be represented by the general formula L-E, where L and E represent, respectively, the receptor binding determinant of the parent ligand molecule and a unit chemical modification that contains an electrophilic group capable of forming a full or partial covalent bond with nucleophilic group Nu of the receptor NuR. L is composed of a linear or discontinuous regions [L1 . . . Lx . . . Lm] that are recognized by the receptor (NuR). Dotted lines connecting [L1 . . . Lx . . . Lm] represent short or extended lengths of the ligand region that do not serve as receptor binding determinants. Linkage of E to the ligand can be accomplished directly or through the use of an adaptor functionality, which is then considered to be a component of E in the general LaCAL formula shown here. Lx corresponds to a functional group of the ligand to which E is coupled. Typical examples of Lx are the —NH2, —COOH, —SH and —OH groups. As macromolecular ligand can express one or more receptor binding determinants, the LaCAL may contain one or more set of each reactive unit composed of [L1 . . . Lx . . . Lm] and E. The covalent bonding between Nu of the receptor and E of LaCAL occurs in conjunction with the classical receptor-ligand interactions mediated by L.

Functional coordination between the traditional non-covalent binding forces responsible for antigen-specific recognition of mature Abs and their nucleophilic sites was examined using large polypeptide CALs (LaCALs). LaCALs contain the phosphonate group within the peptide backbone or the side chain groups of proteins (FIG. 2). Abs specific for the peptide epitopes incorporated in LaCALS displayed irreversible binding at levels exceeding irrelevant Abs (3). As described in Example I, this was true for every Ab examined, including several non-catalytic Abs.

Despite excellent antigen-specific nucleophilic reactivity, most IgG Abs do not express antigen-specific catalytic activity. Occupancy of the B lymphocyte receptor (BCR; surface Ab associated with Igα/Igβ) by the antigen drives B cell proliferation. Efficient BCR catalysis will abort clonal proliferation if the rate of product release is more rapid than BCR transmembrane signaling necessary to induce cell division. This feature of the immune system poses a physiological barrier limiting adaptive improvement of the catalytic function over the course of the immune response. In comparison, there is no bar to improved Ab nucleophilicity if this prolongs BCR occupancy. In the extreme case, increased nucleophilicity could result in formation of a full covalent bond with the antigen. A lesser manifestation is the formation of partial covalent bonds by resonant electron sharing mechanisms (see FIG. 3; a familiar example of a weak bond with partial covalent character is the hydrogen bond). A nucleophilic Ab may also form stable, dead-end covalent complexes with the antigen—two such examples are published (5,6), and in an unpublished study in our lab, we observed stable binding of albumin by certain Abs that were resistant to SDS treatment.

2. Broad Distribution of Protein Nucleophilicity Coordinated with Noncovalent Binding Forces.

As disclosed in Example V, screening of a panel of purified proteins for covalent binding to small CALs (hapten CALs) has revealed that the nucleophilic reactivity is broadly distributed in diverse proteins, including HIV gp120, albumin, the soluble extracellulat domain of the epidermal growth factor receptor (sEGFR), casein and the soluble extracellular domain of CD4 (sCD4). None of these proteins possesses any known enzymatic activity. The level of the nucleophilic reactivity is variable in different proteins, suggesting that it is unique molecular property of each protein.

Also disclosed in the present invention is the facilitatory influence of noncovalent binding interactions on covalent binding between CAL derivatives of two ligands, sCD4-CAL and VIP, by their receptors, gp120 and calmodulin, respectively. High affinity sCD4-gp120 and VIP-calmodulin binding due to noncovalent interactions have been described previously (7,8). SCD4-CAL and VIP-CAL displayed specific and irreversible binding to gp120 and calmodulin, respectively at levels superior to control non-proteinic hapten CALs. The covalent bonding interactions are made possible by the occurrence of the natural nucleophiles expressed by gp120 and calmodulin within their active sites responsible for noncovalent binding to sCD4 and VIP, respectively. gp120 and calmodulin are examples of nucleophilic receptors (NuRs) susceptible to covalent activation or inactivation by LaCALs.

In retrospect, the widespread interactions distribution of protein nucleophilic reactivity coordinated with conventional noncovalent binding forces may be understood as an intrinsic property of protein determinants responsible for intermolecular protein-protein binding. In this novel model of natural protein-protein complexes, certain atoms in the complex are capable of sharing electrons in common orbitals, resulting in stabilization of the complexes. There is no requirement that the natural covalent bonding interactions in the complex be equivalent in strength to a stable covalent bond. The bonding may involve interactions with partial covalent character (a hydrogen bond, for example, serves as an example of a bond with partial covalent character). As noted above, sharing of electrons between the nucleophilic oxygen and the electrophilic carbon atom in the complex shown in FIG. 3 qualifies as an example of a pseudocovalent bond responsible for stabilization of the ground state of the complex. Until now, such bonding interactions were thought to be formed exclusively in the transition state complexes associated with enzymatic catalysis, but there is no theoretical basis to predict that partial covalent bonding is restricted to transition state interactions. The occurrence of nucleophile-electrophile bonding interactions is perceived in our model to occur as a mechanism stabilizing natural intermolecular binding between proteins in the ground state complexes, with no requirement that the reaction proceed to the further steps in chemical catalysis. We view the discovery of nucleophilic reactivity observed using CALs and LaCALs in the present invention, thus, as a reflection of the intrinsic capability of protein active sites to engage in covalent bonding interactions of varying strengths with their natural ligands.

3. Covalent Macromolecular Assemblies.

Intermolecular homoassociation reactions involving the individual molecules of the same protein involves forces similar to those employed in heterocomplexation reactions between different proteins. Disclosed in the present invention is the spontaneous formation of covalent homoassemblies of proteins, including but not limited to HIV gp120-CAL preparations. As in the case of heterocomplexation between LaCALs and NuRS, the assembly is guided by noncovalent interactions involved in formation of natural assemblies of gp120. This protein is well-known to be expressed on the surface of HIV as a noncovalent oligomer. The formation of covalent assemblies of gp120-CAL simulating the native structure of noncovalent gp120 oligomers occurs because the contact regions between of gp120 oligomers contain natural nucleophile-electrophile pairs that are bonded in our model via partial covalent forces. The gp120-CAL preparation disclosed in the present invention contains artificial electrophiles that express stronger covalent reactivity than the natural electrophiles. Therefore, stable covalent bonds are formed with the natural nucleophiles, resulting in assembly of the gp120-CAL oligomers with conformation similar to native gp120 oligomers.

4. CAL Structure.

Diverse hapten CAL and LaCAL structures are disclosed in the present invention to exploit their utility in different types of biological phenomena. CAL design is driven by considerations that will allow the covalently reactive electrophile and the weak binding groups to come into register spatially to obtain specific covalent binding to NuR active sites. Examples of the design features are disclosed as follows.

Hapten CALs are defined as small CALs, usually with mass 1000 Da or less. The reactivity of hapten CALs with NuRs is restricted to covalent reaction with an electrophile contained in the hapten CAL along with noncovalent recognition of adjacent groups. LaCALs can be represented by the general formula L-E, in which L provides weak bonding interactions and E provides the ability to bind covalently to NuRs. NuRs can be membrane bound receptors, soluble receptors, enzymes or antibodies. In the case of a self-assembly reaction, the natural nucleophiles within a NuR reacts with the artificially inserted electrophile in the LaCAL derivative of another NuR molecule. In general, LaCAL structural design is based on the split site model of binding interactions, in which the weak binding ligand subsites in the L component and the electrophilically reactive subsite in the E component are treated as distinct but functionally coordinated regions of the molecule (FIG. 2).

For convenience of explanation, the small molecular weight hapten CALs can be considered equivalent to the E units incorporated within the large L-E structure of LaCALs. Electrophile-nucleophile pairing resulting in covalent bonding takes place at the E unit. For the purpose of this invention, the term "large" includes any entity that can furnish sufficient weak binding forces with aggregate free energy of binding of 7.1 kcal/mole or more (corresponding to Kd $10^{-5}$ M or less). The term "weak" includes traditional noncovalent binding forces, along with natural electrophile-nucleophile pairing reactions leading to bonding with partial covalent character. The specified energy minimum corresponds to the minimum binding energy of interactions typical of weak binding leading to specific receptor-ligand interactions, enzyme-substrate interactions, antigen-antibody interactions and macromolecular self-assembly reactions involved in natural biological reactions.

As an example, the L unit of the LaCALs can be composed of a peptide composed of 4 or more amino acids. Alternatively, a linear or discontinuous epitope contained within a discrete L contained in a large protein can serve as the L component. Oligonucleotides, oligosaccharides and oligolipidic repeat structures also qualify for inclusion as the weak binding L moieties in LaCALs.

In the case of polypeptides, [L1 ... Lx ... Lm] are the component amino acids of the ligand determinant recognized weakly by the LaCAL. These weak interactions occur in conjunction with covalent interaction between one or more LaCAL electrophile and one or more NuR nucleophile (Nu). [L1 ... Lx ... Lm] can be a linear or discontinuous set of amino acids that are spatially in proximity with electrophile. Dotted lines in FIG. 2 connecting [L1 ... Lx ... Lm] represent short or extended lengths of the polypeptide backbone that do not provide binding interactions. As proteins can express one or more binding determinants, polypeptide LaCALs may contain one or more sets of each covalently reactive electrophiles, each in conjunction with its own [L1 ... Lx ... Lm] subsites.

The general LaCAL structure is shown in FIG. 4. The electrophile E is an essential component of all CALs. The covalent reaction with nucleophiles (Nu) found in the targeted protein (the NuR) occurs at an electrophilic atom within E. E is minimally composed of the general formula Y"-Y'-Y, in which: (a) Y contains an electrophilic group; (b) Y' contains a positively charged group, a negatively charged group, a bulky aromatic group or a neutral group that fulfils the non-covalent recognition of the P1 site; (c) Y" is an adaptor group designed to allow linkage to L.

E can be located in LaCAL backbone or at one of the sidechain groups. U.S. Pat. No. 6,235,714 discloses a variant of LaCALs useful for catalytic antibody applications, that is, an electrophile located in the backbone of peptides with an adjacent P1 positively charged group. In the present invention are disclosed additional LaCALs with general utility, i.e., LaCALs with E in the backbone with diverse adjacent P1 and P1' groups, including negatively charged groups, bulky aromatic groups and small and large neutral groups. Additional LaCALs with E located in the side chain groups of L are disclosed in the present invention.

The electrophilic atom (Z) in Y can be any electrophilic atom that can form a stable covalent bond with NuRs, for example, a phosphorus atom, a carbon atom, a boron atom or a vanadium atom (FIG. 5A). In certain LaCALs, Y contains an additional partial or fully charged atom adjacent to the electrophilic atom, for example, the negatively charged oxygen atom of LaCALs containing phosphonate monoesters (FIG. 4, Example 1). U.S. patent application Ser. No. 10/114,716 (filing date Apr. 1, 2002) discloses a variant of LaCALs useful for catalytic antibody applications, that is, a phosphonate monoester LaCAL containing an electrophilic phosphorus atom with an adjacent negatively charged oxygen located within the backbone of peptides. Additional LaCALs are disclosed in the present invention in which Y groups containing an electrophilic atom with an adjacent negatively charged group located in the LaCAL side chains.

Figure 5B:
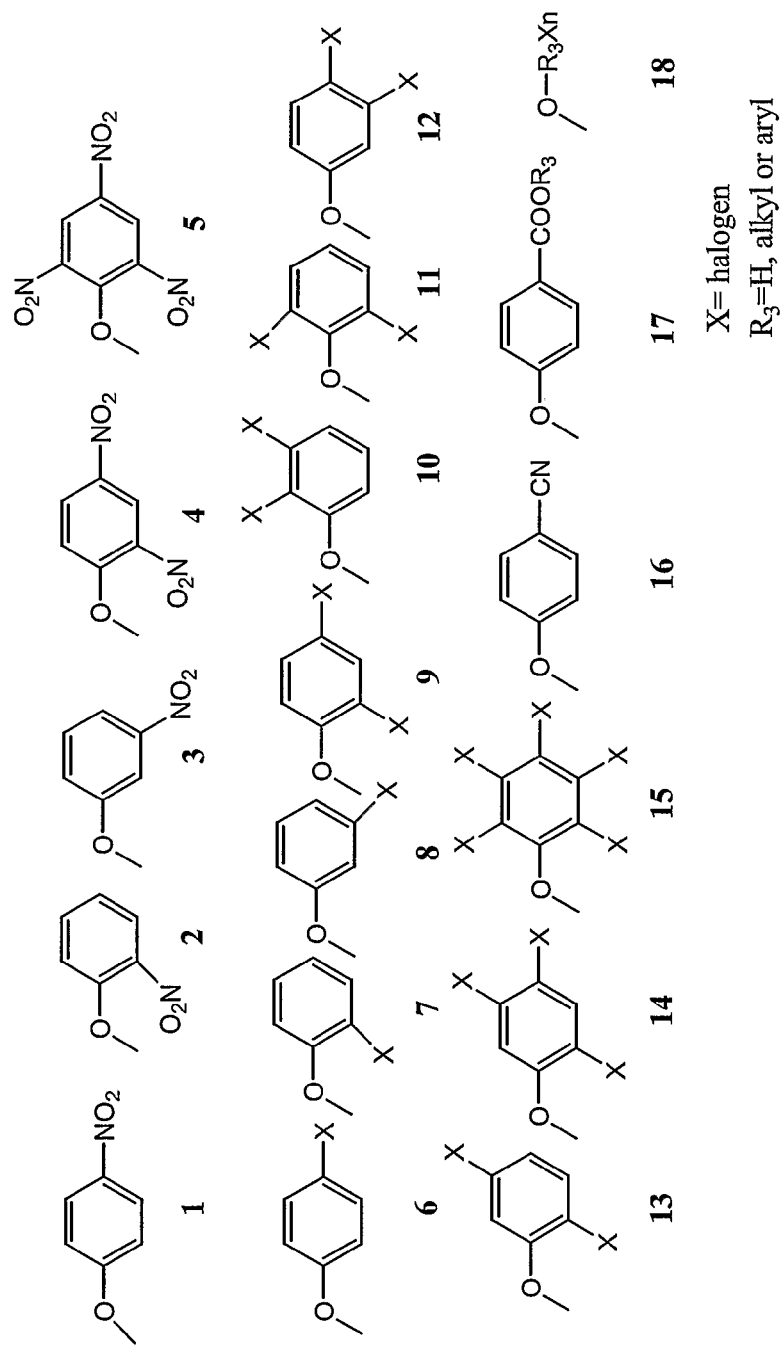
FIG. 5. (A) Y variants. The electrophilic group Y is composed of an electron deficient atom (Z), which forms a covalent bond with Nu, and one (example 2) or more (example 1) substituents (—R1 and —R2) attached to Z. R1 and R2 can be any atoms or groups that permit covalent bonding between Z and Nu. Typical examples of R1 and R2 include alkyl groups, alkoxy groups, aryl groups, aryloxyl groups, hydrogen, and hydroxyl group. R1 and R2 can be pairs of the same or different substituents. (B) Examples of R1 and R2 to increase the covalent reactivity of Y. The electronic characteristics of R1 and R2 control the electrophilic reactivity of Y. Shown are examples of R1 and R2 that increase the covalent reactivity of Y. (C) Examples of R1 and R2 that decrease the covalent reactivity of Y. (D) Examples of R1 and R2 with peptide extensions.
Figure 5C:
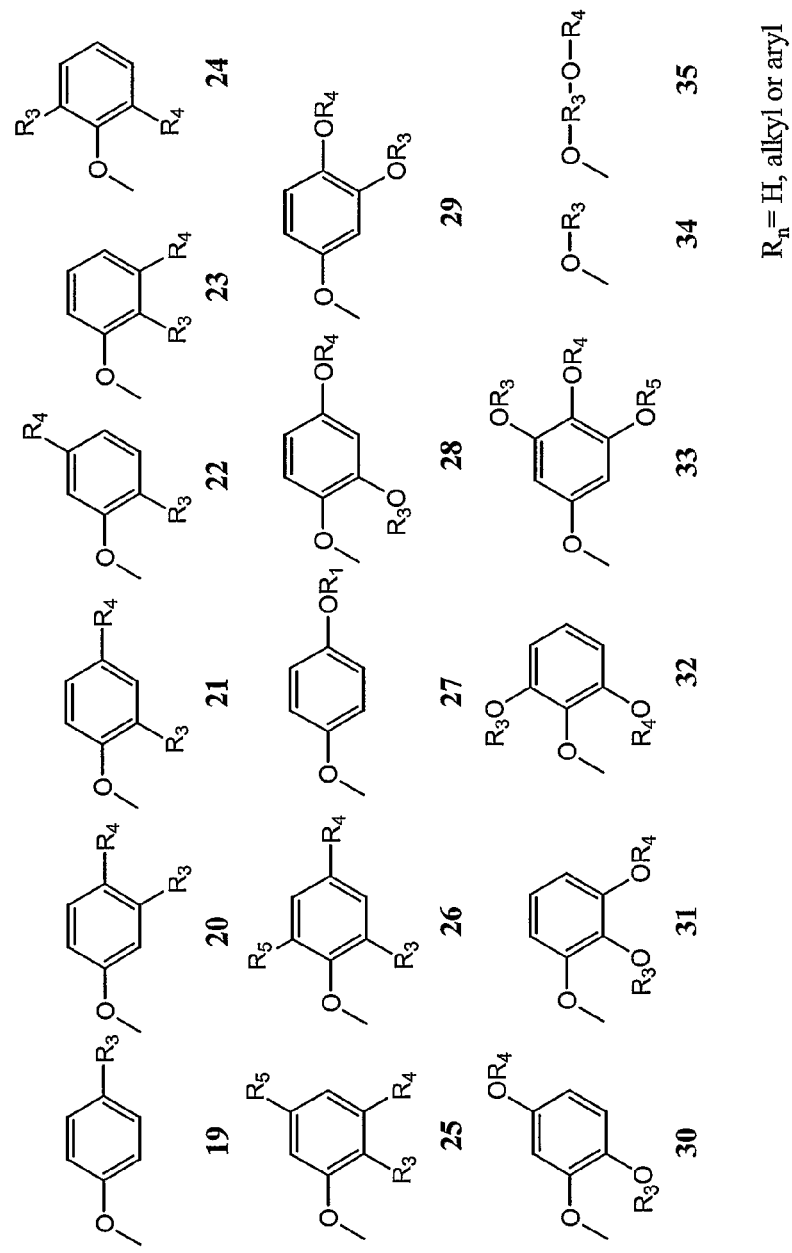

In addition to the electrophilic group, Y can contain substituents with defined electron withdrawing and electron donating capability. Examples of such substituents are shown in FIGS. 5B and 5C. The electron withdrawing and donating groups are linked directly to the electrophilic atom or via spacer groups to enhance and decrease the covalent reactivity of the electrophile with nucleophiles, owing to inductive effects. Substituents 1-18 in FIG. 5B represent groups with varying electron withdrawing capacity. The ideal substituent is one that permits selective binding to the active site of the desired NuR without binding other NuRs. For example, increasing the covalent reactivity of the electrophilic atom to very high levels is undesirable because this may result in covalent binding to enzymes essential for life, such as acetylcholinesterase. Decreases in the covalent reactivity of the phosphorus atom are achieved using substituents 19-35 shown in FIG. 5C.

The P1 and P1' noncovalent recognition requirements of NuRs are fulfilled by incorporating groups with the appropriate charge and bulk within Y' and Y, respectively. Different NuRs have different P1 and P1' recognition requirements. Thus, a positive charge group, a negative charged group, a bulky group or a neutral group are incorporated in these positions to optimize the interaction of LaCALs with the targeted NuR.

Y" represents the adaptor functionality to which the Y'—Y unit can be attached. For example, linkage of Y'—Y to the amino acid side chains of polypeptide ligands can be accomplished directly or through the use of an adaptor group, which is then considered to be a component of E in the general LaCAL structure. The adaptor functionality is also useful for the purpose of varying the flexibility of the construct, as well as features such as the solubility of the overall LaCAL. For example, adaptors can be used that contain only single bonds around which unhindered rotation is possible. This allows the electrophile and other accessory groups included in the constructs to sample a greater extent of conformational space, increasing the opportunity of contact with the nucleophile of the targeted NuR. Similarly, the solubility features of the LaCALs can be modified by including within Y" groups that tend to solvate water, e.g., amines and carboxyl groups.

Figure 6:
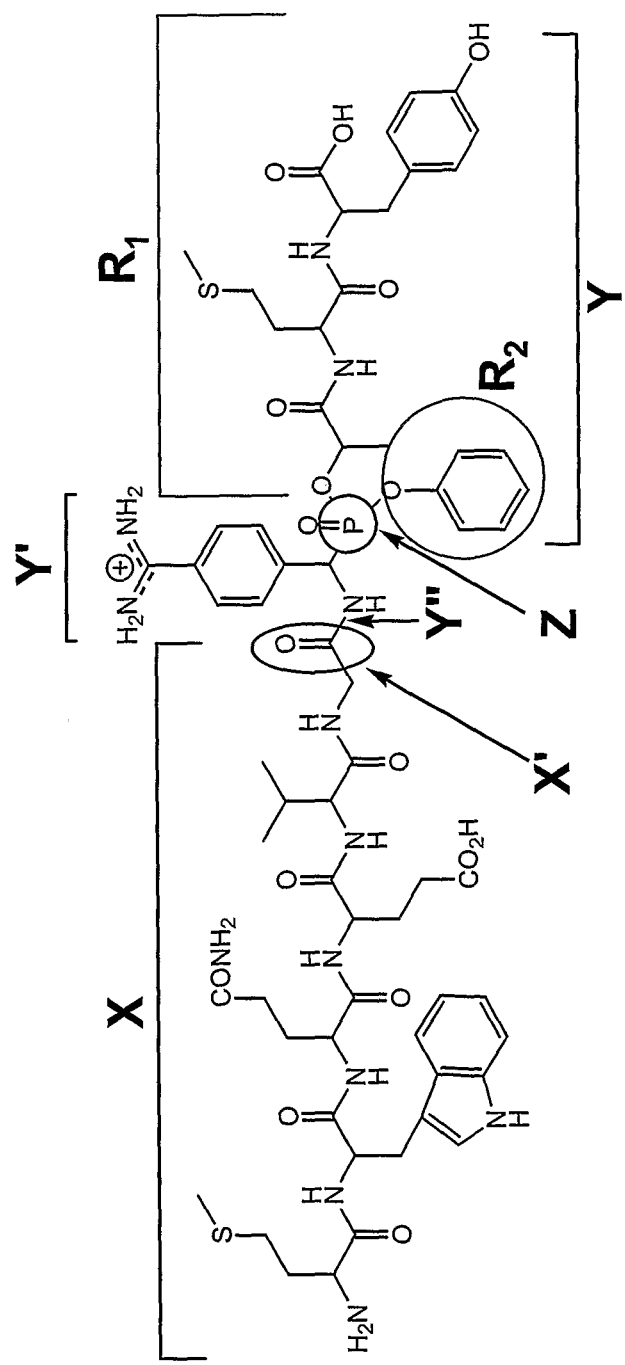
FIG. 6. LaCAL example with a peptide extension on R1. X is composed of the residues 426-431 of HIV-1 gp120. The carboxyl group of Gly431 (X') is connected to the phosphonate diester group Y via an amide bond (Y") and (4-amidinophenyl)methylamine group (Y'). The Y subunit is composed of the reactive phosphorus atom (Z) with two substituents (R1 and R2). The R1 group shown here is an example of 44 in FIG. 3D, where R3 is ethyl group and V is the dipeptide Met-Tyr.

Lx in the general structure corresponds to the functional group of a ligand to which E is attached. In the case of polypeptides, typical examples of Lx are the side chains of Lys, Asp, Glu, Cys, Ser, Thr and Tyr. Examples of the site of linkage of Y"—Y'—Y to these amino acids include the —NH2, —COOH, —SH and —OH groups. In the case of polypeptides, Lx can also correspond to the amine or carboxyl terminus. If X' is the amino or carboxyl terminus of a peptide, and if a peptide is also employed as a component of Y (e.g., FIG. 6), the resultant LaCAL will contain the electrophilic group with peptide flanks on either side.

5. CAL Utility.

CALs that bind covalently to the targeted NuRs can be used for the following purposes:
Permanent inactivation of soluble NuRs;
Permanent inactivation of microbial NuRs;
Potent antagonism and agonism of NuRs expressed on cellular surfaces;
Inactivation or activation of various cellular activities and functions
Induction of growth arrest of death of cells expressing NuRs on their surface;

Generation of covalent mimetics of natural, self-assembled arrays of biomolecules;

Use of the covalent gp120 oligomer mimetic as a vaccine candidate;

Sensitive imaging of cells and microbial organisms expressing NuRs on their surface;

Isolation, induction and inhibition of antibodies in an antigen-specific manner;

Sensitive detection of antibodies and antigens in diagnostic immunoassay applications.

(a) Permanent inactivation of soluble NuRs. One class of soluble NuRs is secreted antibodies with pathogenic effects, e.g., antibodies to transplantation antigens involved in transplant rejection and autoantibodies to self-antigens involved in the pathogenesis of autoimmune disease. Examples of covalent LaCAL engagement of antibodies to epidermal growth factor receptor (EGFR), vasoactive intestinal peptide (VIP), gp120, DNA and Factor VIII are described in Examples I, III and IV. Antibodies to Factor VIII are responsible for bleeding disorders in certain hemophilia patients. Antibodies to EGFR are associated with the autoimmune disease systemic sclerosis. Antibodies to DNA are believed to play a pathogenic role in the autoimmune disease systemic lupus erythematosus. Treatment of antibody mediated diseases is limited at present to drugs that produce nonspecific immunosuppression, with the result that useful immune responses are also suppressed as a side effect. The development of LaCALs allows, for the first time, the targeting of individual antibody populations for inactivation based on their antigenic specificity. LaCALs bind the individual antibody populations specifically and irreversibly. Therefore, they offer an advantage over conventional antigens, in that the latter molecules dissociate from antigen-antibody complexes, regenerating the pathogenic antibodies.

Certain additional soluble NuRs are amenable to the beneficial effect of LaCALs, for example soluble calmodulin described in Example V, FIG. 26). Calmodulin is an important regulator of cellular metabolic functions, as it controls the activity of many signal transducing enzymes, e.g., mysosin light chain kinase and phosphodiesterase. VIP binds calmodulin with high affinity and inhibits calmodulin activation of enzymes. The VIP-CAL described in Example II, FIG. 13 and III, FIG. 18, therefore, can be applied as an irreversible calmodulin antagonist in situations where such an effect will be beneficial, e.g., muscle cell hyperactivity.

Additional soluble NuR targets of LaCALs are shown in Table 1. Exemplary molecules in this group include TNF, IL-1beta, EGF, TGFα, p53 products, prostate specific antigen, carcinoembryonic antigen, prolactin, human chorionic gonadotropin, c-myc, c-fos, c-jun, p-glycoproteins, multi-drug resistance associated proteins, metalloproteinases, steroid receptors and angiogenesis factors. CALs using as starting materials reagents known to bind these NuRs with high affinity, e.g., a LaCAL derivative of the soluble receptors for EGF for targeting of EGF and a CAL derivative of the steroid for targeting of the steroid receptor. Such CALs can be used for treatment of various diseases, including but not limiteds to cancer, inflammatory diseases and cardiovascular diseases.

(b) Permanent inactivation of microbial NuRs. Microbial proteins can also be targeted for inactivation by the LaCALs of the present invention. These include but are not limited to gp120, gp160, Lex1 repressor, gag, pol, hepatitis B surface antigen, bacterial exotoxins (diptheria toxin, C. tetani toxin, C. botulinum toxin, pertussis toxin).

Irreversible binding of HIV gp120 by sCD4-CAL is described in Example VI. Due to the permanent occupancy of the CD4 binding site of gp120 by the sCD4-CAL, the gp120 is no longer capable of binding host cell CD4 receptors, with the result that HIV-1 can not gain entry into the host cells. sCD4 has been proposed as a candidate for HIV therapy, but the potency of sCD4 is too low for it to be useful for therapeutic purposes. The ability of sCD4-CAL to bind gp120 covalently may be anticipated to enhance the therapeutic potency of sCD4 preparations.

(c) Potent antagonism and agonism of NuRs expressed on cellular surfaces. Covalent engagement of the ligand binding site of cellular receptors for hormones, neurotransmitters and other soluble ligands can be anticipated to exert antagonistic or agonistic effects depending on the precise site of covalent attachment within the receptor binding site and the resultant effect on receptor conformation. Cellular receptors mediate the biological effects of ligands by specific ligand binding followed by a signal transducing event. Ligand binding induces changes in the conformation of the receptor, which activates various second messenger systems. For example, VIP binding to cellular VIP receptors activates the enzyme adenylate cyclase and results in increased cyclic AMP production. EGF binding to the EGF receptor activates the intracellular tyrosine kinase domain of the receptor and allows increased phosphorylation of various cellular proteins. If the covalent binding of VIP-CAL to the VIP receptor mimics exactly the weak binding of VIP to the receptor, persistent activation of the receptor will occur, which will be terminated when the receptor becomes uncoupled from its signal tranducing system, for example, by internalization of the receptor. Binding of antagonists to receptors, on the other hand, does not activate the signal tranducing systems underlying the biological effects of the ligands, presumably because the conformational changes induced in the receptor do not mimic sufficiently those required for successful signal transduction.

Regardless of their precise antagonist or agonist effects on membrane receptors, CALs represent a new class of potential therapeutic reagents. For example, overproduction of VIP is associated with certain pancreatic cancers, resulting in life-threatening watery diarrhea (9). The development of potent and specific VIP-CAL as an antagonist for VIP receptors can be applied to control the watery diarrhea. Moreover, the VIP receptor is overexpressed on many cancers and VIP stimulates the growth of certain tumors (10). An anatagonistic VIP-CAL can be employed to control tumor growth. Similarly, an antagonistic EGF-CAL can be employed to control the growth of EGFR overexpressing tumors. Anatgonists of the tyrosine kinase activity of the EGFR and antibodies to EGFR are currently in clinical use as anti-cancer agents (Iressa).

Agonistic effects of CALs can also be perceived to be advantageous, in that the permanent binding to the receptor can activate signal transduction more persistently than reversible ligand binding. A beneficial example is the use of an insulin-CAL to achieve persisten activation of the insulin receptor in diabetes.

Table 1 contains a list of receptors that can be targeted by CALs in this approach. The targets include but are not limited to cytokine receptors, growth factor receptors, hormone receptors, neurotransmitter receptors and angiogenesis factor receptors.

(d) Induction of death of lymphocytes expressing NuRs on their surface. Lymphocytes are responsible for mounting harmful immune responses in various autoimmune diseases and transplant rejection. No effective means are available at present to induce immune tolerance against predetermined antigenic targets. Consequently, generalized immunosuppressive therapies such as treatment with cyclophosphamide and corticosteroids are the mainstay of treatment of these immunological disorders.

Figure 20:
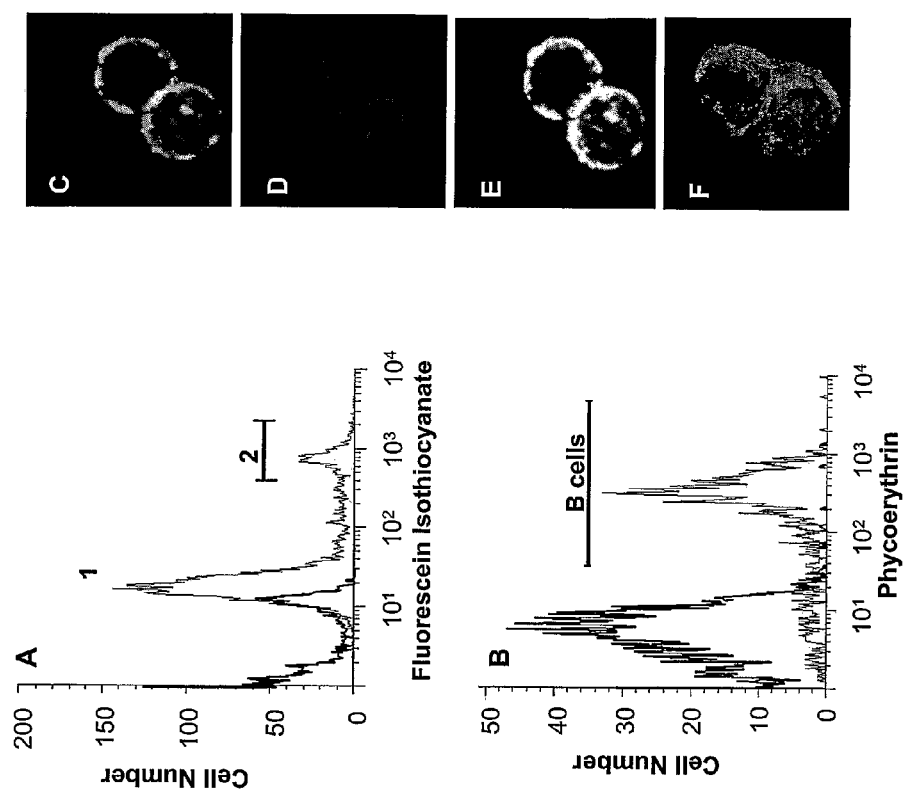

The CALs of the present invention are suitable to achieve permanent occupancy of B cell receptors (BCRs) and T cell receptors (TCRs). Selective covalent binding of hapten CALs by BCRs expressed on the cellular surface is described in Example III FIG. 20. The ability of the BCR to bind antigens specifically derives from the same noncovalent forces underlying specific antigen binding by secreted antibodies. As in the case of secreted antibodies, therefore, inclusion of the appropriate antigenic epitope in the LaCAL allows their selective and covalent binding to antigen-specific BCRs (BCRs are composed of surface antibody complexed to Igα and Igβ subunits). The TCR also expresses specificity for individual antigens. Thus, LaCALs are capable of targeting individual B and T cell populations based on their antigenic-specificity.

Persistent receptor occupancy is well known to induce immunological tolerance. For example, immunization with large doses of antigens results in induction of tolerance due to this effect. Essentially, the persistent receptor occupancy leads to apoptosis, as opposed to clonal selection of the cells. Treatment with large doses of purified Factor VIII, for example, is successful in inducing tolerance in a subpopulation of hemophila patients expressing antibodies to Factor VIII. Irreversible binding of Factor-VIII-CAL to Factor VIII-specific BCRs on the cell surface offers a more potent and cost-effective way to induce immunological tolerance as a therapy for hemophilia in these patients. Smaller amounts of the Factor VIII-CAL are required in this application compared to Factor VIII due to the non-reversible character of Factor VIII-CAL binding to antibodies. Like B cells, T cells are susceptible to tolerance induction by the LaCALs due to persistent TCR occupancy by these compounds. In the case of T cell tolerance induction, it is desirable to employs as LaCALs peptide fragments of the antigen known to serve as T cell epitopes, as LaCAL binding to the TCR can then occur in conjunction with MHC antigens.

Induction of immunological tolerance by LaCALs is a potentially general approach regardless of the exact molecular characteristics of the antigen. Thus, tolerance induction to various protein, nucleic acid, sugar and lipidic antigens is feasible by this approach.

Importantly, cytotoxic agents can be attached to LaCALs if needed to induce the death of B and T cells based on their antigenic specificity, thus supplementing tolerance induction due to persistent receptor occupancy. This is feasible because covalent LaCAL binding to antigen-specific B and T cells can selectively induce the death of these cells, while sparing the organism from generalized negative effects due to the cytotoxic agent. An example of LaCAL-toxin conjugates useful for this purpose is shown in FIG. 17.

(e) Generation of covalent mimetics of natural, self-assembled arrays of biomolecules; covalent gp120 oligomer mimetics as a vaccine candidate. Example VII, FIG. 31 describes the spontaneous assembly of an HIV gp120-CAL into dimers and trimers. The control EGFR-CAL did not display this behavior, and the rate of covalent binding of a hapten CAL with gp120 was considerably smaller than the rate of gp120-CAL self-assembly. These observations suggest that weak noncovalent interactions leading to intermolecular aggregation of native gp120 into oligomers on the viral surface facilitate the self-assembly of gp120-CAL into dimers and trimers. Design of gp120 oliogmers that mimic the native structure of oligomeric gp120 on the surface of HIV has been an intense area of research in the last decade, because the conformation of the monomeric protein deviates significantly from that of the native oligomeric structure, and the monomeric protein induces mainly antibodies to the most mutable region of gp120, the V3 domain. This is a likely contributory reason for the failure of purified monomeric gp120 preparation as a vaccine for HIV-1 infection, as reported by Vaxgen Inc recently (11). Yet, gp120 preparations remains the best hope for vaccination against HIV-1, because this protein is responsible for viral entry into host cells by virtue of its role in host cell CD4 binding and chemokine receptor binding.

We observed that a gp120-CAL preparation containing the covalently assembled dimers and trimers induces the formation of nucleophilic Abs that can neutralize the infectivity of primary HIV-1 isolates in culture. Gp41, an integral membrane protein to which the gp120 oligomers are bound noncovalently, is added to gp120-CAL preparations to promote correctly assembled covalent gp120-CAL oligomers. The gp120-CAL oligomer preparations are potentially useful in two ways: (a) Development of monoclonal antibodies to gp120 for passive immunotherapy of HIV infection; and (b) As a vaccine capable of inducing prophylactic antibodies against HIV-1.

(f) Sensitive imaging of tumor cells expressing NuRs on their surface. Binding of macromolecules to receptors on tumor cells is useful to image primary tumors and the locations of their metastases. For example, radiolabeled somatostatin analogs are useful imaging of tumors expressing somatostatin receptors (12). Radiolabeled VIP has been employed to image VIP receptor-expressing tumors (13). Irreversible binding of the appropriate LaCALs to tumor cell receptors represents an improved and more sensitive method for such imaging applications. For example, the VIP-CAL described in Example II FIG. 13, and Example III, FIG. 18 can be radiolabeled and administered to patients intravenously for imaging of tumor locations. The method is particularly suitable for probes with short half-lives in vivo, as the irreversibly bound LaCAL does not dissociate from the tumor cells, with the result that a smaller concentration of the LaCAL is required to achieve tumor labeling compared to a conventional, reversibly-binding ligand. Radioactive probes are used frequently in these applications. Other probes amenable for modern imaging applications are also available, e.g, near infrared fluorescent probes and positron emission tomography radiotracers (14,15).

(g) Isolation, induction and inhibition of covalent and catalytic antibodies. U.S. Pat. No. 6,235,714, U.S. patent application Ser. No. 10/114,716 (filing date Apr. 1, 2002), and a PCT patent application entitled Proteolytic and Covalent Antibodies, submitted contemporaneously with the present application, describe methods in which LaCALs are employed for the purpose of isolating covalent and catalytic antibodies from autoimmune repertoires, inducing the synthesis of such antibodies by immunization methods and inhibiting the pathogenic effects of such antibodies.

(h) Sensitive detection of antibodies and antigens in diagnostic immunoassay applications. Irreversible LaCAL binding by antibodies offers increased sensitivity of detection. Reversibly binding ligands mixed with antibodies proceed towards the equilibrium state of the reaction, at which the rate of the forward and back reactions become equivalent and the concentration of the antigen-antibody complex remains constant. In comparison, the binding reaction continues to completion for LaCALs until all of the LaCAL has been consumed by covalent binding to the antibody. For example, a diagnostic test for HIV infection is the presence of high levels of antibodies to reversibly binding HIV antigens (gp120, gp160, p24) using immunoblotting or enzyme linked immunosorbent methods. Use of gp120-CAL, gp160-CAL and p24-CAL instead of the reversibly binding antigens in these techniques can be anticipated to increase the amount of bound antibodies, thereby allowing improved antibody detection. As an example, the gp120-CAL described in Example VII, FIG. 31 can be coated on ELISA plates, the test human serum in which the antibodies are to be detected can be incubated with the immobilized gp120-CAL for a suitable length of time, unbound material washed away and the bound antibodies can be detected using anti-human antibodies linked to a fluorescent probe. Detailed ELISA methods are described in refs 3,16.

Empirical experimental criteria considered significant in designing the structure of the hapten CALs and LaCALs include:

The best hapten CALs and pCALs are identified by screening panels of these compounds for rate of binding to NuRs. This includes measurement of the magnitude of the Kd for the reversibly binding step and the first order rate constant k3 for the covalent binding step.

Specificity of hapten CALs and LaCALs is determined by screening for binding to a panel of NuRs, including NuRs unrelated in structure to the targeted NuR. Screening for binding of conventional serine protease and serine esterase enzymes is conducted to ensure that the CALs and LaCALs do not display unacceptable nonspecific to these proteins.

6. Administration of CALs

CALs as described herein are intended to be administered to a patient as a pharmaceutical preparation. The term "patient" as used herein refers to human or animal subjects. The pharmaceutical preparation comprising the hapten CALs and LaCALs of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of hapten CALs and LaCALs in the chosen medium will depend on the hydrophobic or hydrophilic nature of the medium. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the CALs to be administered, its use in the pharmaceutical preparation is contemplated.

Conventional immunization methods are applied to induce antibody synthesis. Several injections of the immunogens (about 100 μg peptide each) are administered to induce Ab synthesis. RIBI will be used in the animal studies. For human use, alum will be employed as the adjuvant. Alum is approved for human use. RIBI is a low toxicity replacement for Freund's Complete Adjuvant, and reproducibly facilitates good antibody responses to a variety of antigens. The immunogens may be administered parenterally by intravenous injection into the blood stream, or by subcutaneous, intramuscular or intraperitoneal injection. Pharmaceutical preparations for parenteral injection are commonly known in the art.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation intended to inhibit NuRs may be administered at appropriate intervals, for example, once a day until the pathological symptoms are reduced or alleviated, after which the dosage may be reduced to a maintenance level. The appropriate interval in a particular case would normally depend on the condition and the pathogenic state sought to be treated in the patient.

In a preferred embodiment, CALs are infused intravenously into the patient. For treatment of certain medical disorders, steps must be taken to ensure that sufficient amounts of the molecules reach their target cells to exert a biological effect.

The lipophilicity of the molecules, or the pharmaceutical preparation in which they are delivered may have to be increased so that the molecules can arrive at their target locations. Furthermore, the Abs of the invention may have to be delivered in a cell-targeted carrier so that sufficient numbers of molecules will reach the target cells. Methods for increasing the lipophilicity and targeting of therapeutic molecules, which include capsulation of the Abs of the invention into antibody studded liposomes, are known in the art.

The CALs that are the subject of the present invention can be conjugated to a carrier such as polyethylene glycol. In addition the CALs can be bound to carriers capable of causing the transfer of said CALs across cell membranes or various blood-tissue barriers, including the blood-brain barrier.

CALs will be selected that will that will fulfill the standard criteria for acceptable prophylatic or therapeutic agents: (1) Covalent binding of the NuRs will lead to a beneficial change in a pathological process by either functionally activating or functionally inactivating the target peptide antigen; and (2) Administration of said CALs will result in a favorable therapeutic index such that the clinical benefit gained outweighs the morbidity associated with any side-effects. Discussions of how such criteria are established for the acceptability of prophylatic or therapeutic agents are common in the art can be found in such texts as *Guide to Clinical Trials* by Bert Spilker, Raven Press, New York, 1991. Acceptable criteria for demonstration of efficacy include, for example, in the case of tumor therapy, a reduction in tumor volume, time to progression and improved survival. In the case of HIV immunotherapy, efficacy is determined by measuring viral burden in the blood, CD4+ T cell counts and the incidence of opportunistic infections.

Any exposed NuR epitope known to be suitable for inactivation, for example by using monoclonal Abs, is a suitable candidate target for the CALs that are the subject of the present invention. The CALs contemplated in the present invention will constitute a major improvement over such conventional monoclonals because of their superior potency, resulting in decrease in the cost of treatment. A listing of some of the NuRs suitable for CAL therapy and the corresponding medical indications are shown in Table 1.

Suitable categories of prophylatic or therapeutic target NuRs for the practice of the present invention include but are not limited to cytokines, growth factors, cytokine and growth factor receptors, proteins involved in the transduction of stimuli initiated by growth factor receptors, clotting factors, integrins, antigen receptors, enzymes, transcriptional regulators particularly those involved in cellular program (differentiation, proliferation and programmed cell death) control, other inducers of these cellular programs, cellular pumps capable of expelling anticancer agents, microbial and viral peptide antigens.

Active immunization will be done using previously developed methods with vaccines designed to elicit protective antibody responses against the desired antigens. For example, the gp120-CAL mixed with a suitable adjuvant formulation such as alum can be administered intramuscularly at a dose optimized for maximum antibody synthesis, and two or three booster injections can be administed at 4 week intervals, until the catalytic antibody concentration in the serum reaches plateau levels. The protective immunity so generated is anticipated to last for several years, because vaccination will result in formation of specific, long lived memory cells that can be stimulated to produce Abs upon exposure to the offending organism or cancer cell. Because Ab synthetic response to most antigens are T cell dependent, an appropriate T cell epitope can be incorporated into the immunogen by peptide synthesis. Alternatively, a carrier such as keyhole limpet hemocyanin can be conjugated to the CALs via coupling through lys side chain amino groups or Cys side chain sulfahydryl groups to maximize the antibody response if necessary.

While certain of the preferred embodiments of the present invention have been described and specifically exemplified, it is not intended that the invention be limited to such embodiments. Various modifications may be made thereto without departing from the scope and spirit of the present invention.

The following examples are provided to facilitate an understanding of the present invention. Methods are disclosed for preparing diverse CALs and LaCALs, detecting their irreversible binding by soluble NuRs and cell surface NuRs, measuring inactivation of NuR bioactivity by CALs, preparing covalent self-assemblies of LaCALs and raising antibodies to LaCALs.

References

1. Erhan S, Greller L D. Do immunoglobulins have proteolytic activity? Nature 1974 Sep. 27; 251(5473):353-5.
2. Gao Q S, Sun M, Rees A R, Paul S. Site-directed mutagenesis of proteolytic antibody light chain. J Mol Biol 1995 Nov. 10; 253(5):658-64.
3. Planque S, Taguchi H, Burr G, Bhatia G, Karle S, Zhou Y X, Nishiyama Y, Paul S. Broadly Distributed Chemical Reactivity of Natural Antibodies Expressed in Coordination with Specific Antigen Binding Activity. J Biol Chem 2003 May 30; 278(22):20436-20443.
4. Gololobov G, Sun M, Paul S. Innate antibody catalysis. Mol Immunol 1999 December; 36(18):1215-22.
5. Rao G, Philipp M. Irreversible inhibition of a monoclonal antibody by a nitrophenyl ester. J Protein Chem 1991 February; 10(1):117-22.
6. Lefevre S, Debat H, Thomas D, Friboulet A, Avalle B. A suicide-substrate mechanism for hydrolysis of beta-lactams by an anti-idiotypic catalytic antibody. FEBS Lett 2001 Jan. 26; 489(1):25-8.
7. Garlick R L, Kirschner R J, Eckenrode F M, Tarpley W G, Tomich C S. *Escherichia coli* expression, purification, and biological activity of a truncated soluble CD4. AIDS Res Hum Retroviruses 1990 April; 6(4):465-79.
8. Stallwood D, Brugger C H, Baggenstoss B A, Stemmer P M, Shiraga H, Landers D F, Paul S. Identity of a membrane-bound vasoactive intestinal peptide-binding protein with calmodulin. J Biol Chem 1992 Sep. 25; 267(27):19617-21.
9. O'Dorisio T M, Mekhjian H S, Gaginella T S. Medical therapy of VIPomas. Endocrinol Metab Clin North Am. 1989 June; 18(2):545-56.
10. Scholar E M, Paul S. Stimulation of tumor cell growth by vasoactive intestinal peptide. Cancer. 1991 Mar. 15; 67(6):1561-4.
11. Watanabe M E. Skeptical scientists skewer VaxGen statistics. Nat. Med. 2003 April; 9(4):376.
12. Shih W J, Hirschowitz E, Bensadoun E, Woodring J, Ryo Y U, Kraman S. Biodistribution on Tc-99m labeled somatostatin receptor-binding peptide (Depreotide, NeoTec) planar and SPECT studies. Ann Nucl Med. 2002 May; 16(3):213-9.
13. Rao P S, Thakur M L, Pallela V, Patti R, Reddy K, Li H, Sharma S, Pham H L, Diggles L, Minami C, Marcus C S. 99mTc labeled VIP analog: evaluation for imaging colorectal cancer. Nucl Med Biol. 2001 May; 28(4):445-50.
14. Ntziachristos V, Bremer C, Graves E E, Ripoll J, Weissleder R. In vivo tomographic imaging of near-infrared fluorescent probes. Mol. Imaging. 2002 April-June; 1(2):82-8.
15. Cohade C, Wahl R L. PET scanning and measuring the impact of treatment. Cancer J. 2002 March-April; 8(2):119-34.
16. Paul S, Planque S, Zhou Y X, Taguchi H, Bhatia G, Karle S, Hanson C, Nishiyama Y. Specific HIV gp120-cleaving Antibodies Induced by Covalently Reactive Analog of gp120. J Biol Chem 2003 May 30; 278(22):20429-20435.

EXAMPLE I

Broadly Distributed Chemical Reactivity of Natural Antibodies Expressed in Coordination with Specific Antigen Binding Activity Many enzymes exploit covalent interactions with substrates to catalyze chemical transformations. Most studies on Ab catalysis, on the other hand, have focused on non-covalent binding forces as the mechanism by which the energy barrier between reactants and products is lowered, e.g., the electrostatic forces that stabilize the negatively charged oxyanionic transition state of ester hydrolysis (reviewed in 1,2). The underlying assumption has been that Abs interact with their ligands exclusively by non-covalent means. Initial indications that natural Abs express chemical reactivity indistinguishable from enzymes came from reports of proteolytic and nuclease activity of autoantibodies (3,4). Similar activities were later found in Ab light chains from multiple myeloma patients (5), alloantibodies from patients with transfusion-induced hemophilia (6), Abs raised by routine immunization with polypeptides (7,8) and anti-idiotypic Abs to anti-enzyme Abs (9). From mutagenesis and inhibitor studies, it appears that the proteolytic activity of natural Abs originates from nucleophilic mechanisms similar to those utilized by conventional serine proteases (10,11). The catalytic activity of natural Abs could be construed to violate the principles of B cell clonal selection theory. Antigen-specific Abs develop over the course of the immune response by sequence diversification of germline genes encoding the V domains, followed by selective antigen binding by B cell receptors with the greatest affinity, which stimulates clonal proliferation Abs. Catalysis entails chemical transformation of the antigen and release of products (surface immunoglobulins associated with Igα and Igβ subunits), which is predicted to result in cessation of B cell selection. Adaptive selection of Ab catalytic activity, therefore, may be a disfavored event. For this reason, catalysis by naturally occurring Abs is often assumed to be a molecular accident arising from sequence variability of the V domains, as opposed to a general phenomenon with functional implications.

The foregoing restrictions do not apply to the initial step in the catalytic cycle of serine proteases catalyst. In analogy with conventional enzymes, a nucleophile belonging to a proteolytic Ab (Nu in FIG. 1A) is conceived to initiate nucleophilic attack on the antigen following formation of the noncovalent ground state complex. Adaptive development of Ab nucleophilicity is fully compatible with B cell clonal selection if the outcome is formation of a covalent acyl-Ab complex, as occupancy of the B cell receptor will be maintained. Whether the catalytic cycle is completed depends on the efficiency of hydrolysis of the acyl-Ab complex and release of the product. Recently, hapten phosphonate esters have been developed as probes for covalent binding to the active site nucleophiles in Abs displaying serine protease and serine esterase activity (11,12) (designated CALs, covalently reactive antigen analogs). These compounds can be applied for direct study of Ab chemical activity independent of additional activities needed for accomplishment of catalysis. In addition, the phosphonates can be placed within peptides and proteins (FIGS. 1B and 1C) for studying the interplay between Ab nucleophilic reactivity and noncovalent forces permitting specific recognition of individual polypeptides.

We describe here observations suggesting the broad distribution of nucleophilic reactivity in IgG and recombinant Fv preparations at levels exceeding that of the conventional serine protease trypsin. Originally prepared as probes for catalytic Abs, CAL analogs of EGFR and an HIV gp120 synthetic peptide were observed to form covalent adducts with ordinary Abs raised by immunization with antigens devoid of the phosphonate groups, suggesting that adaptive maturation processes favor expression of nucleophilic reactivity. These observations argue for Ab nucleophilicity as a force responsible for shaping the expressed Ab repertoire and suggest novel routes towards permanent inactivation of Abs.

Methods

Abs. Human polyclonal IgG was prepared by affinity chromatography on Protein G-Sepharose (Amersham Pharmacia) from sera of 6 healthy human subjects (lab codes 1086, 1087, 1088, 1091, 1092, 1518). IgG from pooled serum from 8 BALB/c mice (4-5 wk) was obtained similarly. Preparation of polyclonal Abs by hyperimmunization with synthetic Cys-gp120(421-436) (KQIINMWQEVGKAMYA; residues 421-436 of gp120 HIV SF2 strain) conjugated to KLH is described in (13). Polyclonal Abs to exEGFR were raised by immunizing female BALB/c mice (5-6 wk) intraperitoneally with exEGFR (10 µg/injection) on days 0, 27 and 41 in RIBI adjuvant and with A431 tumor cells ($10^7$ cells in saline) on day 14. Monoclonal Abs to exEGFR (clones C225, H11, and C111.6) were purchased from Labvision (Fremont, Calif.). A control monoclonal anti-BSA IgG (clone BGN/H8) was from Biogenesis (Kingston, N.H.). Single chain Fv constructs (N=15) were picked randomly from a human Fv library derived from lupus patients described in (11) (MM series clones; 12, 14, 18, 20, 24, F1, F2, F4, F5, F6, F7, F11, F12, F14, F17, F18). The scFv proteins were purified to electrophoretic homogeneity (27 kDa band) by metal affinity chromatography on Ni-NTA columns (11). Expression levels were 0.3-5.7 mg/liter bacterial culture. The library contains diverse scFv clones determined by nucleotide sequencing (11), assuring a broad sampling of Ab V domains. One of the scFv clones examined in the present study, MM-F4, was sequenced (GenBank #AF522073) and its VL and VH domains were determined to belong to families X and I, respectively, and the germline gene counterparts were V1-13 and VH1-2, respectively. Confirmation of scFv band identities in SDS-electrophoresis gels was by immunoblotting using a monoclonal Ab to c-myc (10).

Probes for nucleophiles. Synthesis of hapten CAL I (FIG. 8) and its covalent reactivity with naturally occurring proteolytic Abs has been described previously (11,14). The electrophilic phosphonate diester mimics the peptide bond, the positively charged amidino group mimics the Lys/Arg P1 preference of naturally occurring proteolytic Abs (11), and the biotin group permits sensitive detection of Ab-phosphonate adducts. II was prepared by condensation of diphenyl amino(phenyl)methanephosphonate (compound a) and 6-biotinamidohexanoic acid N-hydroxysuccinimide ester (Sigma) as described for I. For preparation of III, compound a (160 mg, 0.34 mmol) was treated with 30% HBr/CH3COOH (5 ml). The resulting diphenyl amino(phenyl) methanephosphonate hydrobromide (100 mg, 0.24 mmol) was dissolved in 0.5 M sodium methoxide in methanol (9.5 ml), and the solution was stirred under $N_2$ (room temperature, 2 h). After removing solvent under reduced pressure, the residue was extracted with $CH_2Cl_2$ (50 ml), the extract washed with water (5 ml×3), dried over $Na_2SO_4$, and evaporated to dryness. The yellowish oily residue was dissolved in diethyl ether (30 ml). HCl (1 M) in diethyl ether (0.25 ml) was added, yielding a precipitate that was collected by filtration and washed with diethyl ether; yield 35 mg, 68%; $t_R$ 11.8 min (>97% purity; C18 column, 5-80% acetonitrile in 0.1% trifluoroacetic acid, 50 min, 1.0 ml/min); m/z by electrospray ionization mass spectroscopy 216 ($MH^+$). Biotinylation of this compound was done as usual (14). To prepare IV, diphenyl N—[O-(3-sulfosuccinimidyl)suberoyl]amino(4amidinophenyl)methanephosphonate (compound b) was first synthesized by mixing diphenyl amino(4-amidinophenyl) methanephosphonate (0.13 mmol) in DMF (2 ml) containing N,N-diisopropylethylamine (0.11 ml, 0.63 mmol) and bis (sulfosuccinimidyl)suberate disodium salt (150 mg, 0.26 mmol; Pierce) for 2 h. b was purified by reversed-phase HPLC and lyophilized to give a colorless powder; yield 54%, 50 mg; m/z 715 ($MH^+$). Electrophoretically pure exEGFR (0.5 mg; from Dr. O'Connor-McCourt, ref 15) was reacted with 6-biotinamidohexanoic acid N-hydroxysuccinimide ester (59 nmol; Sigma) in 0.53 ml 10 mM HEPES, 150 mM NaCl, 0.1 mM CHAPS, pH 7.5 buffer (50 min, 25° C.). Unreacted biotinylation reagent was removed by gel filtration (Micro Bio-Spin 6 column, BioRad). Biotinylated exEGFR (0.33 mg) was then reacted with compound b (136 nmol) in 3.3 ml buffer for 2 h. Following removal of excess b by gel filtration in 50 mM Tris-HCl, 100 mM glycine, 0.1 mM CHAPS, pH 7.8, the concentration of free amines in the initial and CAL-derivitized proteins was measured using fluorescamine (16). Biotin content determined using 2-(4'-hydroxyazobenzene)benzoic acid (17) was 1.1 mol/mol exEGFR. The density of phosphonate diester labeling was 19 mol/mol exEGFR. Total protein was measured using BCA (Pierce). Some experiments were done using exEGFR CAL IVa. This compound is identical to IV but for the presence of a disulfide bond in linker. To prepare IVa, the precursor diphenyl N-((3-sulfosuccinimidyl)-3,3'-dithiobispropionyl)amino (4-amidinophenyl) methanephosphonate (compound c) was obtained as described for compound b using 3,3'-dithiobis (sulfosuccinimidylpropionate) (Pierce); yield 6.0 mg, 21.4%; tR 24.49 min, >98 purity; 20-50% acetonitrile in 0.1% TFA, 60 min); m/z 751 (MH+). Labeling with biotin and c was as described for IV (biotin and phosphonate diester content of IVa, respectively, 2.3 mol and 18.3 mol/mol exEGFR). Synthesis of peptidyl-CALs V and Va and their chemical characterization are described in (18). V was conjugated with BSA using γ-maleimidobutyric acid N-hydroxysuccinimide ester as in (13). BSA was pretreated with diphenyl N-(benzyloxycarbonyl)amino(4-amidinophenyl)methanephosphonate (BSA, 21.3 µM; phosphonate, 0.5 mM; solvent, 10 mM PBS containing 5% DMSO; 15.5 h) to block potential V binding sites. V/BSA molar ratio was 3.9 determined from consumption of —SH groups using Ellman's reagent. Storage of I-III was at −70° C. as 10 mM solutions in N,N-dimethylformamide. IV and IVa were stored at −70° C. in 50 mM Tris-HCl, pH 8.0, 0.1M glycine, 0.1 mM CHAPS. V and Va were stored at −70° C. as 10 mM solutions in N,N-dimethylformamide.

ELISA. Maxisorp 96-well microtitre plates (Nunc) were coated with gp120(421-436) conjugated to BSA (20 ng peptide equivalent/well; see ref 13 for peptide conjugation method), V conjugated to BSA (20 ng peptide-CAL equivalent/well), exEGFR (200 ng/well) or exEGFR-CAL V (200 ng protein equivalent/well) in 100 mM sodium bicarbonate buffer (pH 8.6, 2 h). ELISA procedures were essentially as described in (13). Bound murine IgG was detected with goat anti-mouse IgG-HRP conjugate (Fc specific; Sigma, Saint-Louis, Mo.; 1:1000).

Irreversible CAL binding. Following incubation of biotinylated CALs with Abs or trypsin (porcine, type IX, Sigma) in 50 mM Tris, HCl, 100 mM glycine, 0.1 mM CHAPS, pH 7.7 at 37° C., the reaction mixtures were boiled (5 min) in 2% SDS and subjected to SDS-PAGE (4-20%, Biorad or 8-25% Phast gels, Amersham). Electroblotting and biotin detection procedures using streptavidin-HRP and a chemiluminescent substrate (Supersignal, Pierce) are described in (11). Imaging and quantification was on X ray film (Kodak) using Unscan-it software (Silk scientific, Orem, Utah) or Fluoro-STM Multi-Imager (Biorad). Band intensities are expressed in arbitrary area units (AAU). Valid comparisons of band intensities from different experiments is not possible as exposure and development times were not held constant. Diisopropyl fluorophosphate (Sigma) was kept at 4° C. until used. In some experiments, biotinylated BSA (Pierce, 8 mol biotin/mol protein) was electrophoresed at several concentrations in parallel with the samples and the biotin content of the CAL adducts was determined. Pseudo-first order rate constants ($k_{obs}$) were computed from reaction progress curves by fitting to the equation $B_t = B_{max}(1-\exp(-k_{obs}t))$ where $B_t$ represents adduct concentration at various times and $B_{max}$, the initial Ab concentration. Immunoblotting with goat anti-mouse IgG Abs was as in (7).

Proteolysis assay. Catalytic activity was measured by fluorimetric determination ($\lambda_{ex}$ 360 nm, $\lambda_{em}$ 470 nm; Varian Cary Eclipse) of the cleavage of amide bond linking aminomethylcoumrain to the C terminal amino acid in short peptide-MCA substrates (10). Catalysts were incubated with peptide-MCA substrates (Pro-Phe-Arg-MCA, Boc-Glu-Ala-Arg-MCA, Boc-Ile-Glu-Ala-Arg-MCA; 200 µM; Peptide International) in 50 mM Tris HCl, 0.1M glycine, 0.025% Tween-20, pH 8.0 at 37° C. in 96-well plates. In some assays, comparison of IgG and trypsin proteolytic activity was done in 10 mM sodium phosphate, pH 7.4, 0.137M NaCl, 2.7 mM KCl, 0.1 mM CHAPS. Authentic aminomethylcoumarin (Peptide International) was used to construct a standard curve from which product release was computed in molar values.

Results

Ab nucleophilicity identified with hapten CALs. Phosphonate hapten CALs I-III (FIG. 8) are analogs of known active site-directed inhibitors of serine proteases (19). Like the serine protease trypsin, IgG from a healthy human subject formed adducts with CAL I that were resistant to boiling and the denaturant SDS FIG. 9; IgG, 150 kD adducts; trypsin, 21 kD adducts). Pooled IgG from immunologically unmanipulated BALB/c mice formed similar I adducts. The positively charged amidino group in CAL I was originally incorporated in this compound to allow selective recognition of trypsin, which displays preference for basic residues at the P1 site (the residue immediately adjacent to the cleavage site in peptide substrates; ref 20). CAL II lacks the positively charged amidino group adjacent to the covalently reactive phosphorus atom. IgG was 240-fold less reactive with II than I, suggesting the trypsin-like P1 specificity of Abs. III, which contains a weaker leaving group than I did not form detectable adducts with IgG (the presence of methoxy leaving groups reduces the electrophilicity of the phosphorus atom; methoxy-containing phosphonate diesters are reported to bind weakly with certain serine proteases, ref 21). Increasing formation of covalent I adducts with IgG and trypsin was evident as a function of reaction time (FIG. 9 B). The velocity of the reaction for IgG was 14.5 fold greater than for trypsin measured under identical conditions (172.7±14.2 and 11.9±0.6 AAU/min, respectively; from linear regression of FIG. 9 B data). Assuming hydrolysis of the phosphonylated-protein complex is equivalent (see reaction scheme in FIG. 1), it may be concluded that the nucleophilic efficiency of IgG is superior to that of trypsin.

IgG preparations from healthy humans and immunologically unmanipulated mice have been documented to cleave small model peptide substrates on the C terminal side of basic residues; the cleavage activity was observed in each of several IgG preparations examined; the activity comigrated with intact 150 kD IgG in denaturing gel filtration studies, and it was expressed by Fab preparations prepared by papain digestion (22). In the present study, we compared the proteolytic activity of trypsin and IgG from a healthy human subject (the same preparation as in the nucleophilicity studies). With Glu-Ala-Arg-MCA and Pro-Phe-Arg-MCA substrates, initial rates of proteolysis by IgG were, respectively, $1.8 \times 10^5$-fold and $6.8 \times 10^5$-fold smaller than by trypsin (FIGS. 8A and 8B, determined from the slopes of the progress curves). Glu-Ala-Arg-MCA is the preferred substrate for trypsin. Glu-Ala-Arg-MCA and Pro-Phe-Arg-MCA are the preferred substrates for human IgG determined from previous screening of a panel of peptide-MCA substrates (22). The magnitude of proteolysis by this IgG preparation falls within the range reported previously for other human IgG preparations. Despite its superior nucleophilic reactivity, the IgG is evidently a poor catalyst compared to trypsin.

CAL I and DFP (another active-site directed inhibitor of serine proteases) inhibited the catalytic activity of IgG-catalyzed peptide-MCA cleavage (FIG. 8 C), and DFP inhibited the irreversible binding of CAL I by the IgG (by 95%). These results provide assurance that CAL I binds the catalytic sites of IgG. As DFP binds the active site of serine proteases, its inhibitory effect confirms the serine protease character of the I binding sites of IgG. Electrophoresis of I-IgG adducts under reducing conditions revealed labeling of both subunits by the hapten CAL, evident as biotin-containing bands at 50 kD heavy chain bands and 25 kD light chain bands (FIG. 8 D). Irreversible I binding activity of IgG was lost by preheating the protein at 60° C. for 10 min, indicating the dependence of the nucleophilic reactivity on the native protein conformation.

Each of 5 polyclonal IgG preparation from healthy humans displayed irreversible binding to I (Table 3). Each of 16 randomly picked scFv clones from a human library formed I-adducts (see example in FIG. 9A), indicating the V domain location of the binding site and suggesting that the nucleophilic reactivity is a shared property of diverse Abs. Ninety one % of the total protein available in Fv MM-F4 shown in FIG. 11A (GenBank #AF522073) displayed nucleophilic reactivity [computed as mol biotin/mol Fv protein in the 27 kD I adduct band; Fv valency 1]. Analyzed by electrophoresis under nonreducing conditions, some scFv reaction mixtures contained CAL I adducts at 55-90 kD in addition to the monomer scFv adducts at 27 kDa. All of the CAL-adduct bands were also stainable with Ab to c-myc, confirming the presence of scFv in the adducts (the recombinant proteins contain a 10 residue c-myc peptide, ref 10). The tendency of scFv to form aggregates has been reported previously (23). Diminished levels of I-adducts were detected when an scFv clone was treated with DFP prior to I-treatment (by 72%). The rate of covalent adduct formation by different Fv clones was variable over a 34-fold range (Table 3), indicating distinct levels of nucleophilic reactivity of different Abs. The reactivity of the 5 polyclonal IgG samples, which represent mixtures of different Abs, was less variable (by 5.4). Comparison of the peptide-MCA cleaving activity (Glu-Ala-Arg-MCA substrate) and irreversible I binding by the scFv clones indicated a strong correlation ($P<0.005$, $r^2=0.77$; FIG. 9B), confirming the functional importance of superior nucleophilic reactivity.

Specific covalent binding of peptidyl and protein CAL. Protein CAL IV and peptide CAL Va were analyzed to assess whether antigen-specific Abs can express nucleophilic reactivity coordinated with noncovalent recognition of the antigen. CAL IV is the extracellular domain of a tumor-associated protein, exEGFR, presenting diverse antigenic epitopes derivitized at Lys side chains with the phosphonate diester (19 mol/mol) along with a small amount of biotin to allow detection of adducts. SDS-electrophoresis of CAL IV revealed a major silver-stained and biotin-containing band with nominal mass 90 kDa (mass of exEGFR 85 kDa; mass of hapten phosphonate group, 714 Da). CAL V corresponds to residues 421-431 of the HIV coat protein gp120, along with the amidino surrogate of Lys432 and the covalently reactive phosphonate diester group located at the C terminus. The purity and chemical characterization of this peptidyl CAL has been reported previously (18). Abs raised by routine immunization with exEGFR and the synthetic peptide corresponding to residues 421-436 of gp120 were initially employed to assure the antigenic integrity of these CALs. ELISA studies indicated that binding of IV and Va (conjugated to BSA) by polyclonal Abs to exEGFR and synthetic gp120(421-436), respectively, was only marginally lower than of the control antigens devoid of phosphonate diester groups, i.e., exEGFR and gp120(421-436), respectively (FIG. 10). Evidently, the epitope structure of the two antigens is preserved despite the introduction of the phosphonate diester in Lys sidechains (IV) and at the C terminus (Va). No binding of anti-exEGFR or anti-gp120(421-436) Abs to immobilized calmodulin and albumin was detected (A490<0.05 at antisera dilution 1:1000), confirming the absence of nonspecific protein binding effects. Immobilized CAL IV and CAL Va (conjugated to BSA) did not display unusual binding to nonimmune Abs used as controls for ELISA, indicating that the phosphonate diester group does not result in indiscriminate covalent binding effects.

Covalent binding by the Abs was studied using denaturing electrophoresis as described for the hapten CALs. Saturable formation of biotin-containing IV adducts with Abs to exEGFR was evident (nominal mass 250 kD). IV adducts of nonimmune IgG were not detectable (FIG. 11). As IV concentration is small (0.2 µM in FIG. 11) formation of adducts similar to those observed using hapten CAL I is not predicted. Little or no adducts were formed in the presence of exEGFR (1 µM) but adduct formation was not impeded by an equivalent concentration of calmodulin, indicating that the covalent binding reaction is at or near the antigen binding site of the Abs. The 250 kD IV adducts were stainable with anti-IgG (data not shown). Each of 3 commercially available monoclonal Abs to exEGFR formed covalent adducts with IVa (according to the suppliers, Ab C225 binds residues 351-364 in the extracellular domain of EGFR; the linear peptide determinant recognized by Abs H11 and C111.6 is not known, but both Abs bind the extracellular domain of the protein), an irrelevant monoclonal Ab did not, and formation of the adducts by the monoclonal Abs was inhibited by exEGFR devoid of phosphonate diester groups but not by the unrelated protein calmodulin. Essentially similar results were obtained using CAL Va (FIG. 12). Formation of biotin-containing 152 kD adducts was saturable as a function of time (mass of Va, 2.2 kD), adduct formation was inhibited by the gp120(421-436)-BSA conjugate (3 µM) but not an equivalent concentration of BSA, and the reaction with nonimmune Abs proceeded slowly compared to the specific Abs.

The pseudo-first order rate constant $k_{obs}$ for accumulation of IV adducts of polyclonal IgG to exEGFR was $1.0\pm0.1$ h$^{-1}$. As no reaction was detected with nonimmune IgG, a precise estimate of $k_{obs}$ is not possible. Using the detection sensitivity of the imaging system as the upper limit for accumulation of adducts over the period of observation in FIG. 12 (133 AAU), the upper limit for $k_{obs}$ is $7.2\times10^{-3}$ h$^{-1}$. Similarly, $k_{obs}$ for accumulation of anti-peptide IgG adducts of Va was 496-fold greater than of nonimmune IgG adducts ($17.8\pm3.3$ h$^{-1}$ and $0.4\times10^{-1}\pm0.1\times10^{-1}$ h$^{-1}$, respectively; FIG. 12 data).

Discussion

Activated nucleophilic residues in conventional serine proteases react covalently with phosphonate diester probes, e.g., the Ser residue activated by hydrogen bonding in the catalytic Ser-His-Asp triad of serine proteases. The presence of such nucleophiles in proteolytic and esterolytic Abs has been deduced from mutagenesis and covalent phosphonate binding studies (10-12). Nucleophilic attack on the substrate is the rate limiting step in catalysis by certain enzymes (24). As the reported catalytic rate constants (kcat) of Abs are generally orders of magnitude lower than of enzymes, it has generally been assumed that the deficiency resides in the nucleophilic reactivity of Abs. Studies reported here indicate otherwise. Despite their low proteolytic activity, IgG preparations displayed stronger nucleophilic reactivity than trypsin determined from rates of formation of covalent adducts with hapten phosphonate diesters. Study of polyclonal IgG and individual scFv clones indicated an apparently universal nucleophilic reactivity. In control experiments, the reactivity was lost upon thermal denaturation, consistent with expectations that activation of the nucleophile is dependent on the native structure of the protein. Covalent Ab binding to the phosphonate diester was inhibited by the established serine protease-reactive reagent DFP. Moreover, Ab proteolytic activity was inhibited by the phosphonate as well as DFP, confirming the serine protease-like character of nucleophiles reactive with the phosphonate. These studies suggest nucleophilic reactivity as an intrinsic property of Abs expressed independent of noncovalent antigen binding forces developed over the course of the immune response. This conclusion is consistent with our previous report that the catalytic triad of a proteolytic Ab light chain is encoded by a germline V gene (25).

Both Ab subunits of IgG displayed covalent binding of hapten phosphonate diester I, consistent with studies in which catalytic Ser nucleophiles have been identified in the light (8,10) and heavy chains (12,26). Study of recombinant scFv clones confirmed the presence of nucleophilic sites in the V domains. The nucleophiles are located within or in the immediate vicinity of the antigen binding site, as suggested by observations of improved covalent binding of antigen-specific Abs to protein CAL IV and peptidyl CAL Va. We did not examine the presence of nucleophilic sites in the constant domains, as the present study was conducted in the context of catalytic activity attributed to the V domains. As the genes encoding the V and constant domains express certain sequence identities (27), the existence of constant domain nucleophiles can not be excluded. Notwithstanding their impressive nucleophilic reactivity, the rate of catalysis by Abs is limited. Presumably, this is because of energetic barriers associated with the deacylation and product release steps (FIG. 1). This statement does not conflict with observations of correlated proteolysis and nucleophilicity of the scFv clones, as increased accumulation of the acylated reaction intermediate will accelerate proteolysis according to the laws of mass action regardless of limitations at subsequent steps in the reaction cycle. In addition to proteases, diverse enzymes involved in chemical transformation of lipids, carbohydrates and nucleic acids owe their catalytic power to covalent mechanisms (28-30). Some of these enzymes are reported to react with phosphonate probes (e.g., 31). An dolase Ab has been raised by immunization with a phosphonate diester hapten (32), but its relationship with innate Ab nucleophilicity is unclear. In addition to protease and esterase activities, Abs express nuclease (4), peroxidase (33) and kinase (34) activities. Conceivably, nucleophilic Ab reactivity described here may play a role in these reactions.

Specific polyclonal and monoclonal Abs to EGFR and synthetic gp120(421-436) peptide displayed covalent binding to the CAL-analogs of these antigens (IV and Va, respectively) at levels substantially greater than nonimmune IgG, indicating that the nucleophiles express their reactivity in coordination with noncovalent antigen binding interactions. Noncovalent Ab-antigen binding may be interpreted, therefore, as a mechanism that permits more efficient delivery of the electrophiles (phosphonate groups) to the Ab nucleophiles. The cognate antigens devoid of phosphonate diester groups inhibited the covalent reaction, suggesting spatial proximity between the nucleophile and residues at which non-covalent binding takes place. The following conditions must be met to explain the experimentally observed antigen-specific formation of the CAL adducts: (a) the germline-encoded nucleophiles must be retained in the Ab combining sites or novel nucleophiles must generated over the course of adaptive Ab specialization; (b) a mechanism must be available to allow improved approach of the Ab nucleophile within covalent binding distance of the phosphonate probe. Precise spatial alignment of Ab nucleophiles in register with the phosphonate groups in IV and Va is unlikely because the Abs were raised by immunization with polypeptides that do not contain these groups. Conversely, the phosphonate electrophiles were placed at the side chain Lys residues of protein IV and the C terminus of peptide Va without foreknowledge of the spatial relationship between the noncovalent and nucleophilic binding sites in the Abs. These considerations suggest that the nucleophiles enjoy sufficient conformational freedom to make contact with imprecisely located phosphonate electrophiles in the antigenic epitope. The mobility of individual amino acids in Ab combining sites following binding to antigen has been reported by other groups (35,36). Previous epitope mapping and mutagenesis studies indicated that the catalytic residues of proteolytic Abs participate minimally in stabilizing the Ab-antigen ground state complex (11,37), suggesting that the mobility of the nucleophile is not restricted by noncovalent binding interactions. Further support for this model is available from observations that MAbs to VIP (38) and gp41 (8) can leave multiple peptide bonds in these antigens, presumably by formation of alternate transition states in which the nucleophile is free to initiate attack on spatially neighboring peptide bonds.

Adaptive improvement in the rate of catalysis by Abs is limited by the mechanisms responsible for clonal selection of B cells. If product release exceeds the rate of transmembrane signaling by the BCR necessary to stimulate cell division, cellular proliferation will cease. On the other hand, there is no bar to adaptive improvement of Ab nucleophilicity, as suggested by the results of the present study. The improved nucleophilic reactivities of antigen-specific Abs described here results from routine immunization with polypeptides. It is difficult to ascribe the reactivity to a fortuitous immunological phenomenon, as it was observed in polyclonal Abs directed to two different antigens and three distinct monoclonal Abs. Nucleophilic attack on the natural counterparts of the phosphonate groups in IV and Va, e.g., the electrophilic carbonyl groups in the peptide backbone and side chain amides, is predicted to result in formation of covalent acyl-Ab complexes (FIG. 1), allowing prolonged occupancy of the BCR and favoring emergence of Abs with improved reactivity. Admittedly, the phosphonate diester group in CALs is more electrophilic than the carbonyl group in proteins antigens, but Ab nucleophilicity is comparable or superior to that of trypsin, suggesting the feasibility of nucleophilic Ab attack on protein antigens. Two examples of Abs with the ability to form irreversible covalent complexes with hapten antigens have been reported (39,40) and certain Abs display SDS-resistant binding to albumin (Paul and coworkers, to be published elsewhere). Ab nucleophilic reactivity could conceivably contribute to Ab-antigen binding without formation of stable covalent bonds. For instance, the nucleophilic reaction may lead to a structure with partial covalent character that does not progress to the acyl-Ab complex because no mechanism is available to donate a proton to the nitrogen atom of the leaving group (C terminal peptide fragment in FIG. 1; ammonia if attack occurs on side chain amide groups).

Important biological effects have been ascribed to the proteolytic activity of Abs found in autoimmune, alloimmune and lymphoproliferative disease (41), e.g., interference with the immunoregulatory (42) and smooth muscle relaxant effects (43) of the neuropeptide VIP. In view of enhanced covalent Ab binding of phosphonate diester groups facilitated by noncovalent binding interactions, peptidyl and proteinic CALs may be hypothesized to permit permanent and selective blockade of the catalytic activity. Moreover, to the extent that expression of nucleophilicity coordinated with noncovalent antigen binding is a general Ab characteristic, CAL inhibition may be generally useful means to inhibit Ab biological effects regardless of catalytic activity. CALs IV and Va, for instance, may be used to study the functional roles of Abs from patients with systemic sclerosis and lupus, which are reported to bind EGFR (44) and synthetic gp120(421-436) (45), respectively.

References for Example I
1. Schultz, P. G., and Lerner, R. A. (1995) *Science* 269, 1835-1842
2. Stewart, J. D., and Benkovic, S. J. (1995) *Nature* 375, 388-391
3. Paul, S., Volle, D. J., Beach, C. M., Johnson, D. R., Powell, M. J., and Massey, R. J. (1989) *Science* 244, 1158-1162
4. Shuster, A. M., Gololobov, G. V., Kvashuk, O. A., Bogomolova, A. E., Smirnov, I. V., and Gabibov, A. G. (1992) *Science* 256, 665-667
5. Matsuura, K., and Sinohara, H. (1996) *Biol. Chem.* 377, 587-589

6. Lacroix-Desmazes, S., Moreau, A., Sooryanarayana-Bonnemain, C., Stieltes, N., Pashov, A., Sultan, Y., Hoebeke, J., Kazatchkine, M. D., and Kaveri, S. V. (1999) *Nat. Med.* 5, 1044-1047
7. Paul, S., Sun, M., Mody, R., Tewary, H. K., Stemmer, P., Massey, R. J., Gianferrara, T., Mehrotra, S., Dreyer, T., Meldal, M., and Tramontano, A. (1992) *J. Biol. Chem.* 267, 13142-13145
8. Hifumi, E., Okamoto, Y., and Uda, T. (1999) *J. Biosci. Bioengin.* 88, 323-327
9. Izadyar, L., Friboulet, A., Remy, M. H., Roseto, A., and Thomas, D. (1993) *Proc. Natl. Acad. Sci. USA* 90, 8876-8880
10. Gao, Q.-S., Sun, M., Rees, A., and Paul, S. (1995) *J. Mol. Biol.* 253, 658-664
11. Paul, S., Tramontano, A., Gololobov, G., Zhou, Y.-X., Taguchi, H., Karle, S., Nishiyama, Y., Planque, S., and George, S. (2001) *J. Biol. Chem.* 276, 28314-28320
12. Kolesnikov, A. V., Kozyr, A. V., Alexandrova, E. S., Koralewski, F., Demin, A. V., Titov, M. I., Avalle, B., Tramontano, A., Paul, S., Thomas, D., Gabibov, A. G., and Friboulet, A. (2000) *Proc. Natl. Acad. Sci. USA* 97, 13526-13531
13. Karle, S., Nishiyama, Y., Zhou, Y.-X., Luo, J., Planque, S., Hanson, C., and Paul, S. (2003) *Vaccine* 21, 1213-1218
14. Nishiyama, Y., Taguchi, H., Luo, J. Q., Zhou, Y.-X., Burr, G., Karle, S., and Paul, S. (2002) *Arch. Biochem. Biophys.* 402, 281-288
15. Brown, P. M., Debanne, M. T., Grothe, S., Bergsma, D., Caron, M., Kay, C., and O'Connor-McCourt, M. D. (1994) *Eur. J. Biochem.* 225, 223-233
16. Udenfriend, S., Stein, S., Bohlen, P., Dairman, W., Leimgruber, W., and Wegele, M. (1972) *Science* 178, 871-872
17. Green, N. M. (1965) *Biochem. J.* 94, 23c-24c
18. Taguchi, H., Burr, G., Karle, S., Planque, S., Zhou, Y.-X., Paul, S., and Nishiyama, Y. (2002) *Bioorg. Med. Chem. Lett.* 12, 3167-3170
19. Oleksyszyn, J., and Powers, J. C. (1994) in Methods in Enzymology vol. 244 (Barrett, A. J., ed.) pp. 423-441, Academic Press, New York
20. Oleksyszyn, J., Boduszek, B., Kam, C. M., and Powers, J. C. (1994) *J. Med. Chem.* 37, 226-231
21. Zhao, Q., Kovach, I. M., Bencsura, A., and Papathanassiu, A. (1994) *Biochemistry* 33, 8128-8138
22. Kalaga, R., Li, L., O'Dell, J. R., and Paul, S. (1995) *J. Immunol.* 155, 2695-2702
23. Whitlow, M., Bell, B. A., Feng, S. L., Filpula, D., Hardman, K. D., Hubert, S. L., Rollence, M. L., Wood, J. F., Schott, M. E., Milenic, D. E. and et al. (1993) *Protein Eng.* 6, 989-995
24. Fersht, A. (1985) Enzyme Structure and Mechanism, W. H. Freeman and Company, New York
25. Gololobov, G., Sun, M., and Paul, S. (1999) *Mol. Immunol.* 36, 1215-1222
26. Zhou, G. W., Guo, J., Huang, W., Fletterick, R. J., and Scanlan, T. S. (1994) *Science* 265, 1059-1064
27. Wuilmart, C., and Urbain, J. (1976) *J. Immunogenet.* 3:1-14
28. Jia, Y., Kappock, T. J., Frick, T., Sinskey, A. J., and Stubbe, J. (2000) *Biochem.* 39, 3927-3936
29. Vocadlo, D. J., Davies, G. J., Laine, R., and Withers, S. G. (2001) *Nature* 412, 835-838
30. Interthal, H., Pouliot, J. J., and Champoux, J. J. (2001) *Proc. Natl. Acad. Sci. USA* 98, 12009-12014
31. Crennell, S. J., Garman, E. F., Philippon, C., Vasella, A., Laver, W. G., Vimr, E. R., and Taylor, G. L. (1996) *J. Mol. Biol.* 259, 264-280
32. Wirsching, P., Ashley, J. A., Lo, C. L., Janda, K., and Lerner, R. (1995) *Science* 270, 1775-1782
33. Takagi, M., Kohda, K., Hamuro, T., Harada, A., Yamaguchi, H., Kamachi, M., and Imanaka, T. (1995) *FEBS Lett.* 375, 273-276
34. Nevinsky, G. A., Kit, Y. Ya., Semenov, D. V., Khlimankov, D. Yu., and Buneva, V. N. (1998) *Appl. Biochem. Biotechnol.* 75, 77-91
35. Jimenez, R., Salazar, G., Baldridge, K. K., and Romesberg, F. E. (2003) *Proc. Natl. Acad. Sci. USA* 100, 92-97
36. Braden, B. C., and Poljak, R. J. (1995) *FASEB J.* 1, 9-16
37. Paul, S., Volle, D. J., Powell, M. J., and Massey, R. J. (1990) *J. Biol. Chem.* 265, 11910-11913
38. Sun, M., Gao, Q. S., Kirnarskiy, L., Rees, A., and Paul, S. (1997) *J. Mol. Biol.* 271, 374-385
39. Rao, G., and Philipp, M. (1991) *J. Protein Chem.* 10, 117-122
40. Lefevre, S., Debat, H., Thomas, D., Friboulet, A., and Avalle, B. (2001) *FEBS Lett.* 489, 25-28
41. Paul, S. (2000) in Chemical Immunology: Catalytic Antibodies, Vol. 77 (Paul, S., ed) pp. 1-158, S. Karger and A. G. Basel, Switzerland
42. Berisha, H. I., Bratut, M., Bangale, Y., Colasurdo, G., Paul, S., and Said, S. I. (2002) *Pulm. Pharmacol. Ther.* 15, 121-127
43. Voice, J. K., Grinninger, C., Kong, Y., Bangale, Y., Paul, S., and Goetzl, E. J. (2003) *J. Immunol.* 170, 308-314
44. Planque S., Zhou Y.-X., Nishiyama Y., Sinha, M., O'Connor-McCourt M., Arnett F. C. and Paul S. (2003) *FASEB J.* 17, 136-143
45. Bermas, B. L., Petri, M., Berzofsky, J. A., Waisman, A., Shearer, G. M., and Mozes, E. (1994) *AIDS Res. Hum. Retroviruses* 10, 1071-1077

EXAMPLE 2

Towards Selective Covalent Inactivation of Pathogenic Antibodies: A Phosphonate Diester Analog of Vasoactive Intestinal Peptide that Inactivates Catalytic Autoantibodies Specific antigen recognition by the variable domains underlies the pathogenic effects of certain antibodies (Abs) produced as a result of autoimmune, allergic and anti-transplant reactions. For instance, Abs found in myasthenia gravis (reviewed in ref. 1) and hemophilia (reviewed in ref. 2) bind important epitopes of the acetylcholine receptor and Factor VIII, respectively, which interfere with the biological activity of these proteins by a steric hindrance mechanism. Other Abs utilize their Fc region to mediate pathogenic effects but antigen recognition by Ab variable domains is the stimulus initiating these effects, e.g., Ab recognition of erythrocyte antigens stimulates complement activation by the Fc region in autoimmune hemolytic anemia and incompatible blood transfusions. Similarly, allergen recognition by IgE bound to Fc receptors on the surface of mast cells stimulates their degranulation. In other diseases, the mechanism of Ab pathogenicity is less clear. For example, Abs to nucleic acids in lupus (reviewed in ref. 3) and to thyroglobulin in Hashimoto's thyroiditis (reviewed in ref. 4) are unambiguously disease-associated, but additional immune abnormalities are also evident in these diseases, and the precise functional effects of the Abs remain debatable. Recently, a novel variable domain mechanism underlying Ab pathogenicity has emerged, viz., the catalytic cleavage of antigens. Hydrolytic catalysts such as Abs to polypeptides (5-8) and nucleic acids (9) hold the potential of permanent antigen inactivation. Moreover, catalysts are endowed with turnover capability, i.e., a single Ab molecule can hydrolyze multiple antigen molecules, suggesting that such Abs may exert functional effects that are more potent than Abs dependant on stoichiometric antigen recognition. Abbreviations: Ab, antibody; AMC, 7-amino-4-methylcoumarin; BSA, bovine serum albumin; CAL, covalently reactive antigen analog; DFP, diisopropyl fluorophosphate; exEGFR, extracellular domain of human epidermal growth factor receptor; KLH, keyhole limpet hemocyanin; MCA, methylcoumarinamide; V domain, variable domain; VIP, vasoactive intestinal peptide Abs that catalyze the cleavage of VIP have been identified in patients with autoimmune disease (10). VIP is a 28 amino acid peptide with important biological actions, including immunoregulation via actions on T lymphocytes (reviewed in ref. 11) and control of blood and air flow via actions on the smooth muscle (reviewed in ref. 12). A model proteolytic Ab interferes with cytokine synthesis by cultured T cells accompanied by depletion of cellular VIP (13) and administration of the Ab to mice interferes with relaxation of airway smooth muscle (14). Proteolytic Abs to VIP appear to utilize a covalent catalytic mechanism reminiscent of serine proteases. This is suggested by studies in which replacement of the active site Ser residue resulted in loss of catalytic activity (15), and by inhibition of catalysis by haptenic phosphonate diesters (10). These compounds form adducts with the activated nucleophiles of enzymes by virtue of the covalent reactivity of the electrophilic phosphorus atom (reviewed in ref. 16), and have been developed recently as probes for the active site nucleophiles in Abs displaying serine protease and serine esterase activity (17,18) [designated covalently reactive antigen analogs (CALs)].

As in the case of ordinary Abs, traditional noncovalent antigen recognition is hypothesized to underlie the specificity of the proteolytic Abs for VIP. CALs of the VIP sequence represent, therefore, a potentially specific means to target the Abs by virtue of offering a reaction surface that combines covalent binding to the Ab active site with noncovalent binding at neighboring peptide epitope(s). Here we describe the antigen-specific covalent reaction of monoclonal and polyclonal Abs with a synthetic VIP-CAL compound. Despite positioning of the phosphonate group at a single site, Lys20, the covalent reaction resulted in irreversible inhibition of polyclonal Abs that cleave VIP at several peptide bonds located between residues 7 and 22. The results suggest the feasibility of targeted inactivation of individual Ab populations based on their antigenic specificity.

Materials and Methods

CALs. Diphenyl N-(6-biotinamidohexanoyl)amino(4-amidinophenyl)methanephosphonate (1) was prepared from diphenyl amino(4-amidinophenyl)methanephosphonate (19, 20) and 6-biotinamidohexanoic acid (Anaspec; San Jose, Calif.) by the aid of PyBOP (Novabiochem; San Diego, Calif.). The HPLC-purified material [retension time 20.76 min, purity 95% (220 nm); YMC ODS-AM column (4.6×250 mm), 0.05% TFA in water (A):0.05% TFA in acetonitrile (B) 90:10 to 20:80 in 45 min (1.0 ml/min)] was characterized by ESI-MS [Observed m/z 721.3 (MH$^+$; calculated MH$^+$ for $C_{36}H_{45}N_6O_6PS$, 721.3)] and stored as 10 mM solution in DMF at −70° C. The active ester 2 was prepared by acylating the same precursor amine with disuccinimidyl suberate (Pierce; Rockford, Ill.) and characterized in the same way [Observed m/z, 635.3 (MH$^+$; calculated MH$^+$ for $C_{32}H_{35}N_4O_8P$, 635.2)]. VIP-CAL (3) was synthesized as follows. The VIP sequence with N-terminal biotin was constructed on Rink amide MBHA resin (0.72 mmol/g; Novabiochem) by the standard 9-fluorenylmethoxycarbonyl protocol (21) except that 4-methyltrityl (22) was used for side-chain protection of Lys20. The peptide-resin was treated with 1% TFA in dichloromethane (5 min×10) to remove the 4-methyltrityl group and the deprotected amino group of Lys20 was acylated with 2 in 1-methyl-2-pyrrolidinone containing 0.1 mM N,N-diisopropylethylamine. The peptide resin was treated with TFA-ethanedithiol-thioanisole-phenol (90:1:1:8) at room temperature for 2 h. After removing the resin by filtration, diethyl ether was added to the solution to afford a precipitate, which was collected by centrifugation and washed with diethyl ether. The HPLC-purified material [retention time 50.25 min, purity 96% (220 nm); Vydac 214TP C4 column (4.6×250 mm); A:B 90:10 to 60:40 in 60 min (1.0 ml/min)] was characterized by ESI-MS [Observed m/z, 4071.4 (MH$^+$; calculated MH$^+$ for $C_{185}H_{282}N_{49}O_{49}PS_2$, 4072.0) and stored as 10 mM solution in DMSO at −70° C.

Abs. Monoclonal anti-VIP IgG clone c23.5 and control isotype-matched IgG clone UPC10 (IgG2a, κ; Sigma; St. Louis, Mo.) were purified from ascites by affinity chromatography on immobilized Protein G-Sepharose (23). Polyclonal IgG from the serum of a human subject with chronic obstructive pulmonary disease (designated HS2 in ref. 24) was also purified by Protein G-Sepharose chromatography. The recombinant light chain of anti-VIP Ab clone c23.5 (GenBank # L34775) was expressed in bacterial periplasmic extracts and purified by binding of the his6 tag to a Ni-affinity column (15). All Abs were electrophoretically homogeneous. Protein concentrations were determined with Micro BCA Protein Assay kit (Pierce).

CAL adducts. Covalent binding assays were carried out as described previously (17,20). Briefly, IgG (1 μM) was incubated with compound 1 or 3 (10 μM) in 10 mM sodium phosphate, 0.137 M NaCl, 2.7 mM KCl (PBS, pH 7.4) containing 1 mM CHAPS and 0.1% DMSO (in 3-binding experiments) or 0.1% DMF (in 1-binding experiments) at 37° C. In some experiments, the reaction was conducted in the presence of human plasma collected in EDTA (pooled from 8 healthy blood donors; 1% v/v). Aliquots of the reaction mixtures at 10, 20, 40, 60, 90 and 120 min were boiled in 2% SDS containing 3.3% 2-mercaptoethanol in a water bath (5 min) and then subjected to electrophoresis (4-20% polyacrylamide gels; Bio-Rad; Hercules, Calif.). Following electroblotting onto nitrocellulose membranes (TransBlot; Bio-Rad), biotin-containing adducts were stained with a streptavidin-peroxidase conjugate and a chemiluminiscent substrate kit (Supersignal; Pierce). Band density was expressed in arbitrary area units (AAU) determined using a Fluoro-STM MultiImager (Bio-Rad), taking care that the densities were within the linear response range.

Catalysis assays. Pro-Phe-Arg-AMC (0.2 mM; Peptides International, Louisville, Ky.) was incubated with Ab (0.8 μM) in 96 well plates in 50 mM Tris.HCl-0.1M glycine (pH 8.0) containing 0.6% DMSO and 0.025% Tween 20 at 37° C. and release of AMC determined by fluorometry (λem 470 nm, λex 360 nm; Cary Eclipse spectrometer; Varian; Palo Alto, Calif.). Preparation and assay of cleavage of [Tyr$^{10}$-$^{125}$I]-VIP were described previously (24). To determine if the CALs inhibit Abs irreversibly, IgG (2 μM) was incubated (37° C.) with 1 or 3 for 16 h in 50 mM Tris.HCl-0.1M Gly (pH 8.0) containing 2.5% DMSO and 0.025% Tween 20. Unreacted 1 or 3 was then removed by chromatography of the reaction mixtures (0.2 ml) on protein G columns as in ref 35 (50 μl settled gel; washed with 0.8 ml 50 mM Tris.HCl, pH 7.4; eluted with 0.2 ml 0.1 M Gly.HCl, pH 2.7; neutralized with 1M Tris.HCl, pH 9). Fifty μl aliquots of the recovered IgG (and IgG-CAL complexes) were incubated with [Tyr$^{10}$-$^{125}$I]-VIP (86,000 c.p.m.) for 18 h and peptide cleavage was determined by measuring the radioactivity soluble in trichloroacetic acid. Control IgG samples were incubated without CAL, chromatographed and analyzed for VIP cleaving activity in the same way.

Results

VIP-CAL. Important features in design of the VIP-CAL (compound 3, FIG. 14A) are: (a) Inclusion of the electrophilic phosphonate diester group capable of selective reaction with activated nucleophiles such as are found in serine proteases (16); (b) Location of the positively charged amidino group in proximity to the phosphonate to allow recognition by the model proteolytic IgG clone c23.5, which cleaves peptide bonds preferentially on the C terminal side of basic amino acids (Arg/Lys) (23,25); and (c) Incorporation of these groups on the side chain of Lys20 in the sequence of VIP. Hapten CAL 1 contains the phosphonate diester and amidino groups but is devoid of the VIP sequence. Location of the covalently reactive moiety at Lys20 is based on observations that the Lys20-Lys21 peptide bond is one of the bonds cleaved by monoclonal Ab clone c23.5 (23) and polyclonal human IgG preparations containing Abs to VIP (24). Peptide inhibitors of proteases customarily contain the covalently reactive group located within the peptide backbone or at the peptide termini (e.g., 26,27). In the present study, our purpose was to maximize the opportunity for approach of the phosphonate group within covalent binding distance of the nucleophile contained in diverse Ab active sites. For this reason, the phosphonate group was placed at the side chain of Lys20 using a flexible linker, which allows rotation at several C—C bonds (as opposed to inclusion of the phosphonate within the peptide backbone, which may impose a greater level of conformational constraints on accessibility of this group).

VIP-CAL 3 was synthesized by the regioselective on-resin acylation as outlined in FIG. 14B. The VIP sequence was constructed by solid-phase peptide synthesis with standard 9-fluorenylmethoxycarbonyl chemistry except that the 4-methyltrityl group was used for side-chain protection of Lys at position 20 (4a). After selective removal of 4-methyltrityl, peptide resin 4b was acylated with 2, which was prepared from diphenyl amino(4-amidinophenyl)methanephosphonate and disuccinimidyl suberate. The resulting peptide resin 4c was treated with anhydrous TFA to give 3, which was purified with HPLC, yielding a single species with the anticipated mass (m/z, 4071.4; calculated value, 4072.0).

Covalent Ab Labeling. Monoclonal Ab c23.5, raised by hyperimmunization with VIP. It is characterized by strong recognition of the ground state of VIP (Kd 1.9 nM; Km 0.34 nM), made possible by traditional noncovalent Ab paratope-epitope interactions (23). The catalytic site of the Ab is located in the light chain subunit and is composed of a serine protease-like catalytic triad (15). Here, we compared the covalent binding of this Ab by VIP-CAL 3 and hapten CAL 1. The isotype-matched Ab UPC10 (IgG2a, .kappa.) served as the control to determine background Ab nucleophilic reactivity independent of noncovalent recognition of VIP. The covalent reaction was visualized by boiling the reaction mixtures followed by denaturing SDS-electrophoresis and detection of biotin-containing adducts (FIG. 15A, inset). Accumulation of covalent VIP-CAL 3 adducts with the anti-VIP Ab increased linearly as a function of time, (the CAL-Ab reactions are predicted to follow the second-order rate law, and linear adduct accumulation will occur in the initial stage of the reaction) with the light chain subunit accounting for the majority of the adducts (nominal mass 29 kD determined by comparison with molecular mass standards). Adducts of VIP-CAL 3 with the control Ab were formed at lower levels. Similarly, hapten CAL 1 reacted with anti-VIP and control Abs slowly compared to the VIP-CAL, and there was no preference for covalent binding of the hapten CAL at the light chain subunit. Apparent reaction velocities (V.sub.app) were obtained from the slopes of linear regression curves fitted to the progress data by least square analysis ([Ab-CAL]=V.sub..appt, where [Ab-CAL] represents the intensity of Ab-CAL adduct band in AAU, and t, the reaction time]. V.sub.app values are compiled in Table 5. For the anti-VIP Ab, V.sub.app of the VIP-CAL 3 reaction with the light chain was 6.6-fold greater than the heavy chain. Hapten CAL 1 V.sub.app values for the two subunits of this Ab were nearly equivalent. V.sub..app for the reaction of VIP-CAL with the anti-VIP light chain was 66-fold greater than the corresponding reaction with the control Ab light chain. These observations indicate the selective nucleophilic reactivity of the ant-VIP light chain. Inclusion of VIP devoid of the phosphonate group in the reaction mixture inhibited the formation of VIP-CAL 3 adducts with the anti-VIP light chain (FIG. 15B; inhibition in 3 repeat experiments, 41.0.+7%). It may be concluded that selective covalent binding of VIP-CAL 3 by the anti-VIP Ab is made possible by noncovalent interactions due to the presence of the VIP sequence. The CAL-Ab reactions are predicted to follow the second-order rate law, but linear adduct accumulation will occur in the initial stage of the reaction.

Pooled plasma from healthy humans was included in the reaction along with VIPase c23.5 to investigate further the selectivity of the VIP-CAL. As expected, the predominant VIP-CAL 3 adduct appeared at the position of the light chain subunit of the VIPase Ab (FIG. 15C). Little or no reaction of the VIP-CAL with plasma proteins and the control IgG subunits was observed. Similarly, the reaction mixtures of hapten CAL 1 yielded little or no adduct formation with plasma proteins or the exogenously added monoclonal Abs. Faint biotin bands were observed upon prolonged exposure in each of the lanes shown in FIG. 15C at mass 67-70 kD. These bands presumably reflect low level adduct formation of the hapten CAL and VIP-CAL with albumin, the major protein present in plasma (see silver-stained electrophoresis lane in FIG. 15C). Covalent reactions of albumin with organophosphorus compounds have been reported previously (28,29).

Diisopropyl fluorophosphate (DFP), a well-established serine hydrolase inhibitor, was previously reported to inhibit catalysis by anti-VIP light chain c23.5 (15). In the present study, DFP inhibited the covalent VIP-CAL binding to the light chain (FIG. 15D), consistent the presence of a serine protease-like binding site(s).

Inhibition of Catalytic Activity. The cleavage of the model peptide substrate Pro-Phe-Arg-AMC by the recombinant light chain of anti-VIP Ab c23.5 has been reported previously (15). Site-directed mutagenesis studies have suggested that the light chain contains a catalytic triad similar to the active site of serine proteases (15). Here, the progress of Pro-Phe-Arg-AMC cleavage by the light chain was measured fluorimetrically by determining AMC generated due to cleavage at the Arg-AMC amide bond. As expected, a linear increase of AMC fluorescence was evident (FIG. 16A). Inclusion of VIP-CAL 3 in the reaction mixture inhibited the reaction in a time dependent manner. The deviation of the progress curve from linearity in the presence of VIP-CAL suggests an irreversible inhibition mode (30). Inhibitory potency comparisons using VIP-CAL 3 and hapten CAL 1 indicated the superior potency of the former compound (IC$_{50}$ 1.5 μM and 27 μM, respectively; FIG. 16B). The superior potency of VIP-CAL 3 is consistent with the covalent adduct data reported in the preceding section and may be attributed to improved noncovalent recognition of the peptidyl component of VIP-CAL 3. The stoichiometry of the inhibition was determined by titration with limiting amounts of VIP-CAL 3 ([3]/[light chain] ratio: 0.0375-3.75; FIG. 16C). The x-intercept of the residual activity (%) vs [VIP-CAL 3]/[light chain] plot was 0.89, suggesting a 1:1 stoichiometry. This is consistent with the observed molecular mass of the light chain:VIP-CAL adduct, i.e., 29 kD (light chain, 25 kD; VIP-CAL, 4 kD).

Figures 17A, 17B, 17C:
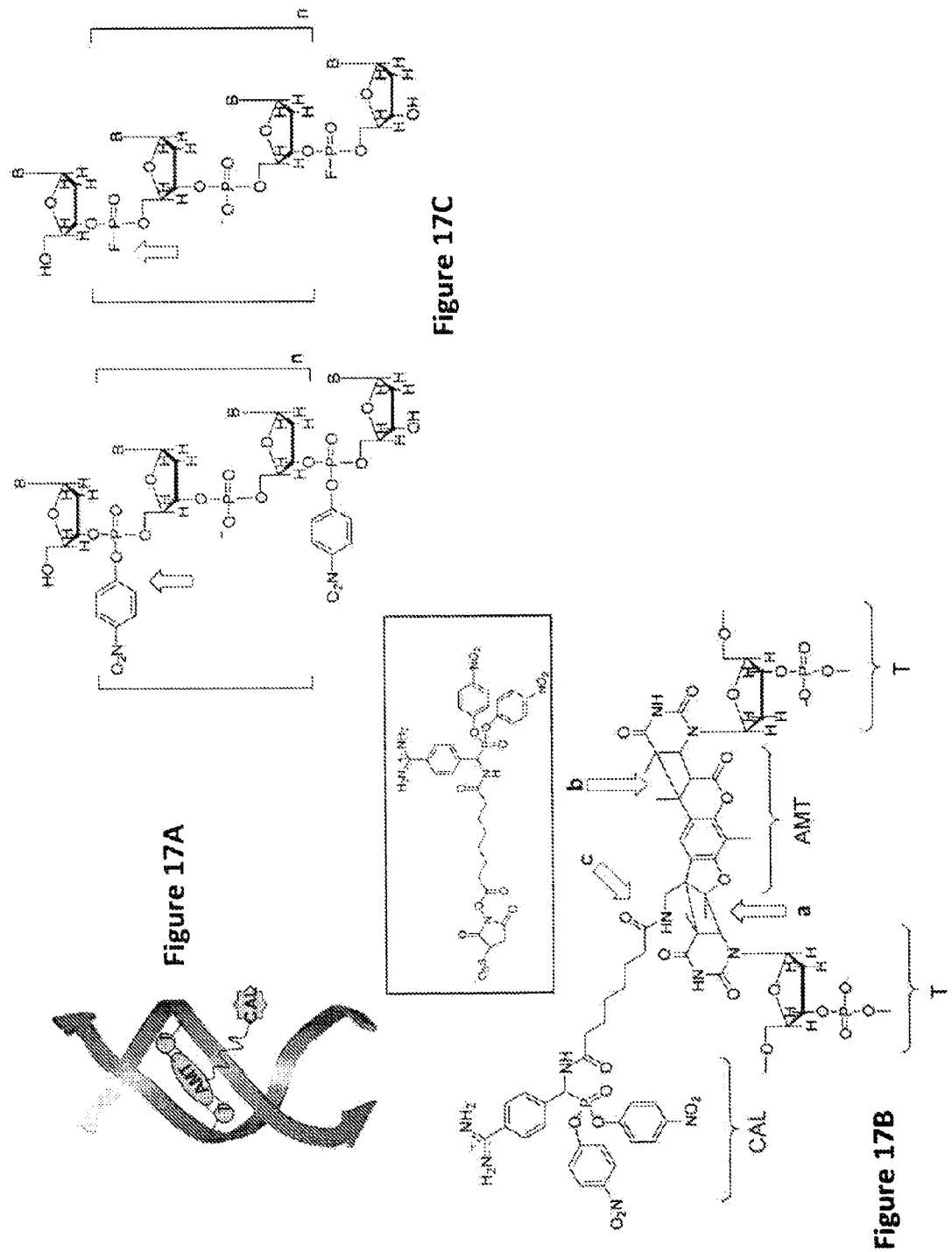

Next, we turned to a human polyclonal IgG preparation isolated from a subject with airway disease (designated HS-2 in ref. 24). Cleavage of VIP by this preparation has been attributed to IgG autoantibodies based on retention of the activity in Fab fragments, adsorption of the activity by IgG binding reagents and absence of VIP cleavage by control, identically-purified human IgG preparations. N-terminal sequencing of VIP fragments generated by this IgG has identified the following scissile bonds: Thr7-Asp8, Arg14-Lys15, Gln16-Met17, Met17-Ala18, Ala18-Val19, Lys20-Lys21 and Lys21-Tyr22 (24). Here, we initially confirmed the ability of the polyclonal IgG preparation to cleave multiple peptide bonds in VIP. Three new radioactive peaks were generated from [Tyr$^{10}$-$^{125}$I]-VIP by treatment with the IgG (FIG. 17A). The observed radioactive product peaks in FIG. 17A likely represent mixtures of peptide fragments, as the VIP fragments generated by cleavage at the aforestated peptide bonds have previously been noted to elute from the HPLC with similar retention times (24).

To determine whether VIP-CAL 3 is an irreversible inhibitor, aliquots of the IgG treated with varying concentrations of this compound (10, 20, 40, 80 µM) were subjected to affinity chromatography on protein G to remove the unreacted inhibitor, followed by assay of the cleavage of [Tyr$^{10}$-$^{125}$I]-VIP (FIG. 17B). Control IgG was subjected to an identical incubation without VIP-CAL followed by the chromatographic procedure. Dose-dependent inhibition of catalytic activity was evident, and near-complete inhibition of catalysis was observed at VIP-CAL concentrations >20 µM. The observed irreversible inhibition suggests that VIP-CAL forms covalent adducts with the polyclonal Abs, similar to its behavior with the monoclonal Ab examined in the preceding section. Selectivity of the VIP-CAL inhibitory effect was confirmed by comparison with happen CAL 1. As expected, the VIP-CAL inhibited the cleavage of VIP more potently than the hapten CAL ($IC_{50}$: 7 µM and 36 µM, respectively).

Discussion

The following conclusions may be drawn from these data: (a) Functionally coordinated noncovalent and covalent interactions allowed nucleophilic anti-VIP Abs to form specific and covalent adducts with the VIP-CALs; and (b) The VIP-CAL inhibits each of the reactions involving cleavage of VIP at several peptide bonds, indicating its potential as a universal inhibitor of diverse anti-VIP catalytic Abs. The importance of noncovalent Ab paratope-antigen epitope binding in directing the VIP-CAL to the Ab nucleophile is evident from the following observations: lower reactivity of the anti-VIP monoclonal Ab with the hapten CAL devoid of the VIP sequence; limited reactivity of the irrelevant isotype-matched Ab and plasma proteins with the VIP-CAL; and, inhibition of the anti-VIP Ab covalent reaction with the VIP-CAL by VIP devoid of the CAL moiety. Recently, CAL derivatives of other polypeptide antigens (HIV gp120 and epidermal growth factor receptor) have also been reported to form covalent adducts with specific Abs directed to these antigens, with only minor levels of reactions evident with Abs directed to irrelevant Abs (31,32). Taken together, these considerations open the route towards permanent inhibition of individual Ab subpopulations based on their antigenic specificity.

The light chain subunit accounted for most of the covalent reactivity of the anti-VIP monoclonal Ab with the VIP-CAL. Reactivity with the hapten CAL serves as an index of Ab nucleophilicity independent of traditional noncovalent forces responsible for Ab-antigen complexation. Hapten CAL reactivities of the anti-VIP heavy and light chain subunits were comparable, suggesting that differences in intrinsic nucleophilic reactivity do not account for rapid formation of adducts of the light chain with the VIP-CAL. It may be concluded that the light chain nucleophile is in the immediate vicinity of the Ab noncovalent binding site, and the noncovalent binding interactions facilitate covalent binding. This statement is consistent with observations that the purified light chain of this Ab is capable of specifically catalyzing the cleavage of VIP (25). Previously, the purified light and heavy chain subunits of the Ab were reported to bind VIP independently, determined by a conventional assay for noncovalent Ab-antigen complexes (Kd for light chain, heavy chain and intact IgG, respectively: 10.1, 6.8 and 1.9 nM; ref. 33). In addition to the light chain, the heavy chain subunit appears to contribute noncovalent binding energy for Ab complexation with VIP, but the heavy chain nucleophile does not seem to be sufficiently in register with the phosphonate group of the VIP-CAL to participate in the covalent reaction.

Additional evidence for irreversible and specific Ab recognition by the VIP-CAL is available from the catalysis assays. VIP-CAL adducts of the Abs obtained following removal of unreacted VIP did not display catalytic activity. Catalytic cleavage of Pro-Phe-Arg-AMC by the recombinant light chain of the monoclonal Ab has been documented previously (15). This reaction is characterized by 57.5-fold higher Km than the cleavage of VIP by the light chain, and is attributed to cross-reactivity of the catalytic site with peptide substrates devoid of an antigenic epitope capable of participating in high affinity noncovalent binding. Pro-Phe-Arg-AMC cleavage by the light chain was inhibited more potently by the VIP-CAL than the hapten CAL. Similarly, the cleavage of VIP by polyclonal human autoantibodies to VIP was inhibited more potently by the VIP-CAL than the hapten-CAL.

Ab diversity poses an interesting challenge in achieving antigen-specific covalent inactivation of pathogenic Abs. Structural differences in the variable domains underlies Ab specificity for individual antigenic epitopes, and even Abs to small molecules presenting a limited surface area can contain structurally distinct binding sites (e.g., 34,35). Catalytic IgG preparations from patients with autoimmune disease cleave several backbone bonds in polypeptide (7,24) and oligonucleotide (9) antigens. This may be due to the presence of multiple Ab species in polyclonal IgG preparations, each with a distinct scissile bond specificity. We have suggested previously that the nucleophiles enjoy some measure of mobility within Ab active sites that is not subject to restriction when noncovalent binding of Abs and antigens takes place (31,32). To the extent this hypothesis is valid, Abs with differing peptide bond specificity could react covalently with the VIP-CAL even if the phosphonate group is located somewhat imprecisely in the antigenic epitope. In the present study, placement of the phosphonate on the Lys20 side chain (as opposed to the peptide backbone) and inclusion of a flexible linker represent attempts to expand further the conformational space available for the covalent reaction. Complete inhibition of catalytic hydrolysis of VIP by polyclonal Abs that cleave several bonds between VIP residues 7 and 22 by the VIP-CAL was evident. Promising means to obtain antigen-specific covalent inhibition of diverse Abs include, therefore, the exploitation of intrinsic conformational properties of Ab catalytic sites and the provision of enhanced access to the phosphonate group by manipulating the linker structure. In comparison, if Ab-antigen binding is conceived as a rigid body interaction involving inflexible surface contacts, covalent inhibitor design must entail close topographical simulation of the transition state of each scissile bond, and individual inhibitors must be developed to effectively inhibit different catalytic Abs. The importance of evaluating conformational factors in inhibitor design is supported by previous reports suggesting a split-site model of catalysis (31,32) in which antigen binding at the noncovalent subsite imposes little or no conformational constraints on the catalytic subsite, allowing the catalytic residue to become positioned in register with alternate peptide bonds as the transition state is formed.

As noted previously, catalytic Abs are proposed to contribute in the pathogenesis of autoimmune disease. Specific covalent inhibitors represent a novel means to help define the precise functional effects of the Abs. Such inhibitors may serve as prototypes for development of therapeutic agents capable of ameliorating harmful Ab effects. In addition to inactivation of secreted Abs, reagents such as the VIP-CAL may be useful in targeting antigen-specific B cells. The feasibility of this goal is indicated by evidence that CATs bind covalently to Abs expressed on the surface of B cells as components of the B cell receptor. Ab nucleophilicity may be viewed as an indication of their competence in completing the first step in covalent catalysis, i.e., formation of an acyl-Ab reaction intermediate. This is supported by observations that the magnitude of Ab nucleophilic reactivity is correlated with their proteolytic activity (31). A recent study suggests that noncatalytic Abs also contain nucleophiles but are unable to facilitate steps in the catalytic cycle following covalent attack on the antigen, viz., water attack on the acyl-Ab intermediate and product release (31). Regardless of the physiological functions of nucleophiles expressed by noncatalytic Abs, their presence may allow CAL-targeting of Ab populations with established pathogenic roles, e.g., anti-factor VIII Abs in hemophilia.

[3] S. Paul and coworkers, unpublished data.

References for Example II
1. Vincent, A. (2002) *Nat. Rev. Immunol.* 2, 797-804
2. Gilles, J. G., Vanzieleghem, B., and Saint-Remy, J. M. (2000) *Semin. Thromb. Hemost.* 26, 151-155
3. Rekvig, O. P., and Nossent, J. C. (2003) *Arthritis Rheum.* 48, 300-312
4. Tomer, Y. (1997) *Clin. Immunol. Immunopathol.* 82, 3-11
5. Paul, S., Volle, D. J., Beach, C. M., Johnson, D. R., Powell, M. J., and Massey, R. J. (1989) *Science* 244, 1158-1162
6. Matsuura, K., and Sinohara, H. (1996) *Biol. Chem.* 377, 587-589
7. Lacroix-Desmazes, S., Moreau, A., Sooryanarayana, Bonnemain, C., Stieltjes, N., Pashov, A., Sultan, Y., Hoebeke, J., Kazatchkine, M. D., and Kaveri, S. V. (1999) *Nat. Med.* 5, 1044-1047
8. Hatiuchi, K., Hifumi, E., Mitsuda, Y., and Uda, T. (2003) *Immunol. Lett.* 86, 249-257
9. Shuster, A. M., Gololobov, G. V., Kvashuk, O. A., Bogomolova, A. E., Smirnov, I. V., and Gabibov, A. G. (1992) *Science* 256, 665-667
10. Bangale, Y., Karle, S., Planque, S., Zhou, Y. X., Taguchi, H., Nishiyama, Y., Li, L., Kalaga, R., and Paul, S. (2003) *FASEB J.* 17, 628-635
11. Voice, J. K., Dorsam, G., Chan, R. C., Grinninger, C., Kong, Y., and Goetzl, E. J. (2002) *Regul. Pept.* 109, 199-208
12. Maggi, C. A., Giachetti, A., Dey, R. D., and Said, S. I. (1995) *Physiol. Rev.* 75, 277-322
13. Voice, J. K., Grinninger, C., Kong, Y., Bangale, Y., Paul, S., and Goetzl, E. J. (2003) *J. Immunol.* 170, 308-314
14. Berisha, H. I., Bratut, M., Bangale, Y., Colasurdo, G., Paul, S., and Said, S. I. (2002) *Pulm. Pharmacol. Ther.* 15, 121-127
15. Gao, Q. S., Sun, M., Rees, A. R, and Paul, S. (1995) *J. Mol. Biol.* 253, 658-664
16. Oleksyszyn, J., and Powers, J. C. (1994) in *Methods in Enzymology*, (Barrett, A. J., ed) Vol. 244, pp. 423-441, Academic Press, San Diego, Calif.
17. Paul, S., Tramontano, A., Gololobov, G., Zhou, Y. X., Taguchi, H., Karle, S., Nishiyama, Y., Planque, S., and George, S. (2001) *J. Biol. Chem.* 276, 28314-28320
18. Kolesnikov, A. V., Kozyr, A. V., Alexandrova, E. S., Koralewski, F., Demin, A. V., Titov, M. I., Avalle, B., Tramontano, A., Paul, S., Thomas, D., Gabibov, A. G., and Friboulet, A. (2000) *Proc. Natl. Acad. Sci. U.S.A.* 97, 13526-13531
19. Oleksyszyn, J., Boduszek, B., Kam, C. M., and Powers, J. C. (1994) *J. Med. Chem.* 37, 226-231
20. Nishiyama, Y., Taguchi, H., Luo, J. Q., Zhou, Y. X., Burr, G., Karle, S., and Paul, S. (2002) *Arch. Biochem. Biophys.* 402, 281-288
21. Wellings, D. A., and Atherton, E. (1997) in *Methods in Enzymology* (Fields, G. B., ed) Vol. 289, pp. 44-67, Academic Press, New York, N.Y.
22. Aletras, A., Barlos, K., Gatos, D., Koutsogianni, S., and Mamos, P. (1995) *Int. J. Pept. Protein Res.* 45, 488-496
23. Paul, S., Sun, M., Mody, R., Tewary, H. K., Stemmer, P., Massey, R. J., Gianferrara, T., Mehrotra, S., Dreyer, T., Meldal, M., and Tramontano, A. (1992) *J. Biol. Chem.* 267, 13142-13145
24. Paul, S., Mei, S., Mody, B., Eklund, S. H., Beach, C. M., Massey, R. J., and Hamel, F. (1991) *J. Biol. Chem.* 266, 16128-16134
25. Sun, M., Gao, Q. S., Kirnarskiy, L., Rees, A., and Paul, S. (1997) *J. Mol. Biol.* 271, 374-385
26. Oleksyszyn, J., and Powers, J. C. (1991) *Biochemistry* 30, 485-493
27. Sampson, N. S., and Bartlett, P. A. (1991) *Biochemistry* 30, 2255-2263
28. Means, G. E. and Wu, H. L. (1979) *Arch. Biochem. Biophys.* 194, 526-530
29. Schwartz, M. (1982) *Clin. Chim. Acta* 124, 213-223
30. Marangoni, A. G. (2003) *Enzyme Kinetics: A Modern Approach*, John Wiley and Sons, Hoboken, N.J.
31. Planque, S., Taguchi, H., Burr, G., Bhatia, G., Karle, S., Zhou, Y. X., Nishiyama, Y., and Paul, S. (2003) *J. Biol. Chem.* 278, 20436-20443
32. Paul, S., Planque, S., Zhou, Y. X., Taguchi, H., Bhatia, G., Karle, S., Hanson, C., and Nishiyama, Y. (2003) *J. Biol. Chem.* 278, 20429-20435
33. Sun, M., Li, L., Gao, Q. S., and Paul, S. (1994) *J. Biol. Chem.* 269, 734-738
34. Kaartinen, M., Pelkonen, J., and Makela, O. (1986) *Eur. J. Immunol.* 16, 98-105
35. Mitchell, T. J., and Reilly, T. M. (1990) *Pept. Res.* 3, 277-281

Footnotes
[1] Abbreviations used are: AAU, arbitrary area unit; Ab, antibody; AMC, 7-amino-4-methylcoumarin; CHAPS, 3-[(3-cholamidopropyl)dimethylammonio]-1-propanesulfonic acid; CAL, covalently reactive analog; DMF, N,N-dimethylformamide; DMSO, dimethyl sulfoxide; ESI-MS, electrospray ionization-mass spectrometry; Fc, fragment constant;

PyBOP, (benzotriazole-1-yl)oxytris(pyrrolidino)phosphonium hexafluorophosphate; SDS, sodium dodecylsulfate; TFA, trifluoroacetic acid; $V_{app}$, apparent reaction velocity; VIP, vasoactive intestinal peptide.

EXAMPLE III

Irreversible Inhibition of Noncatalytic Antibodies and Tolerance Induction

The CAL reaction provide, for the first time, the opportunity to irreversibly inactivate secreted Abs and Ab-producing cells based on antigenic specificity. The feasibility of this goal is supported by our observations concerning specific covalent blockade of Abs to vasoactive intestinal peptide (VIP) by a synthetic VIP-CAL containing a phosphonate diester group on the Lys20 side chain (1). In principle, this approach could lead to a platform technology for treatment of diseases involving harmful Ab effects, e.g., autoimmune diseases, allergic disease and transplant rejection. The potential ameliorative effect of the CALs is not limited to their reaction with proteolytic Abs, as non-catalytic Abs also express nucleophilic reactivity coordinated with noncovalent antigen recognition. Abs directed to the following antigens were observed in our previous studies to bind covalently to the appropriate LaCALs: VIP (1), full-length HIV gp120 (2) and a peptide gp120 fragment; epidermal growth factor receptor (extracellular domain; 3) and Factor VIII.

Covalent inactivation of secreted, pathogenic Abs is predicted to provide short-term relief, but inhibition of the cells responsible for Ab synthesis represents the more interesting therapeutic route. At limiting concentration, antigen binding to B cells stimulates clonal expansion and increased Ab synthesis. In contrast, BCR saturation at excess antigen concentration induces clonal anergy and apoptotic death (4). Tolerance induction by noncovalent allergens and autoantigens is a well-established phenomenon, but success rates are limited. Permanent BCR occupancy by CALs is anticipated to drive the B cells into the apoptotic pathway. As in the case of conventional antigen binding, a sufficient number of BCRs must be saturated to achieve this outcome (as opposed to cell division). As dissociation of CAL-BCR complexes is precluded, BCR saturation can be more readily achieved at a small CAL concentration.

1. Targeting VIP Antibodies and DNA Antibodies.

Two targets of LaCALs are discussed in the present example: antibodies to DNA and VIP. There is no assumption in this discussion that either antibody population possesses catalytic activity. As described in Example I, all antigen-specific antibodies examined thus far display specific and covalent binding to LaCALs provided the appropriate antigenic epitopes are incorporated into the LaCALs.

Anti-DNA Abs are promising candidate targets for lupus therapy. Abs to double stranded DNA (dsDNA) are a diagnostic criterion for lupus, and Abs capable of binding single stranded DNA (ssDNA) and various nucleic acid-protein complexes are found as well (5,6). Abs eluted from the kidneys of lupus patients display strong reactivity with DNA, anti-DNA Abs isolated from the blood of lupus patients bind kidney sections, and adoptive transfer of anti-DNA Abs induces kidney damage in experimental animals (7,8). A major mechanism underlying anti-DNA pathogenicity is thought to entail the following events: binding to DNA-containing nucleosomes or a cross-reactive protein antigen, penetration of the cell and nuclear membranes, and induction of apoptotic cell death (8-11). Some reports suggest that the DNase activity of certain lupus Abs confers enhanced cytotoxic activity (12,13). Another mechanism invokes the deposition of immune complexes by binding to Fc receptors, followed by damage resulting from complement activation. Immune complexes containing DNA of varying size may not be equivalently pathogenic. These mechanisms are not mutually exclusive—for example, anti-DNA Ab binding to nucleosomes may induce complement activation and Ab internalization by the cells may occur as well.

VIP is a 28 amino acid peptide synthesized by neurons and also produced endogenously by T cells. Originally known for the ability to relax the smooth muscle (14), VIP is now recognized as an important regulator of T cells. Abs to VIP can deplete the VIP available to T lymphocytes and other cell types in which the peptide exerts its biological effects. The role of Abs to VIP as pathogenic mediators is supported by these considerations: (a) Administration of exogenous VIP completely suppresses rheumatoid arthritis in a collagen-induced animal model of the disease (15); (b) VIP autoantibodies are found in patients with respiratory diseases, lupus patients and the MRL/lpr mouse strain, which develops lupus-like disease; (c) Certain recombinant Fv clones isolated from human autoimmune phage display libraries (lupus) displayed specific VIP binding, confirming that the active site is located in the V domains (16,17); (d) Polyclonal anti-VIP Abs suppress VIP-induced synthesis cAMP, the second messenger utilized by VIP (18); (d) VIP regulates the production of cytokines by T cells (19,20) and aberrant VIP receptor expression on T cells is shown to alter their responses to antigens (21); and, (e) Alterations in the tissue concentrations of VIP have been noted in murine lupus (22).

2. CALs.

Concepts derived from study of nucleophilic anti-peptide Abs are applicable to anti-DNA Abs for the following reasons: formation of protein-DNA covalent intermediates by nucleophilic centers in certain DNA cleaving enzymes is a well known phenomenon; hapten phosphonate probes identify Ab nucleophilic reactivity independent of paratope specificity; and, the Ab nucleophilic activity is germ-line encoded and there is no reason to expect that the activity will be lost as anti-DNA Abs undergo affinity maturation. DNA-CAL and VIP-CAL design is based on the split site model, in which the Ab nucleophile is spatially separated from the non-covalent antigen binding site. In the reaction scheme of FIG. 1, CALs that fully mimic reversible antigen binding to Ab will possess low $K_i$ (equilibrium dissociation constant) and large $k_3$ (strength of covalent reaction). These are desired CAL kinetic properties.

DNA-CALs (see FIG. 17 for structures). The antigenic specificity of anti-DNA Abs is of considerable importance in designing inhibitors of the Abs. Anti-dsDNA are established to be capable of causing kidney damage, and some evidence is available that anti-ssDNA Abs are also pathogenic (23,24). Abs to dsDNA usually also bind ssDNA, but anti-ssDNA Abs do not recognize dsDNA (5,23-26). The binding site of anti-dsDNA is usually a cleft, whereas anti-ssDNA Abs appear to contain a more shallow site with limited penetration of the DNA into the protein (24,27). Five-mer oligonucleotides are sufficient to bind the Abs, and there is limited specificity for recognition of individual DNA sequences (5,28). However, base preferences are evident, with several anti-dsDNA Abs displaying preference for G-C rich regions, and others, for A-T rich regions (5,23). Contacts of Ab combining site residues with negatively charged phosphate groups as well as the bases are described, and in some Abs, base stacking within the combining site allows stabilization of the AB-DNA complex.

Several types of CALs can be readily prepared, e.g., the large dsDNA-CAL 1 and a single stranded oligonucleotide- CAL 2 (oligo-CAL 2). The starting material can be calf thymus dsDNA digested with restriction enzymes to yield ~200 bp fragments. Use of heterogenous dsDNA is desirable to target the spectrum of autoantibodies to dsDNA found in lupus. [Note: smaller dsDNA-CALs can be readily prepared based on findings that lupus anti-DNA Abs display preferences for A-T rich structural cores of DNA (e.g., ref 28)]. dsDNA-CAL is prepared by the photochemical reaction 4'-aminomethyl-4,5',8-trimethylpsoralen (AMT). The primary reaction is cyclobutane ring formation between the 5,6 double bond of thymidine in DNA and the psoralen 4',5' or 3,4 double bonds. Reaction at the 4',5" double bond (arrow a) results in a monoadduct, which reacts further with a pyrimidine on the complementary strand (arrow b) forming an interstrand cross-link (A and B) (30). The pre-activated biotin-containing CAL moiety (inset) is linked to the amine of AMT (arrow c). Reaction stoichiometry is optimized to yield adducts containing 1 molecule CAL/30 bp. This is intended to enable covalent Ab binding without disrupting overall DNA structure. CAL density can altered if needed. Psoralen incorporation is determined by measuring primary amines. CAL incorporation is determined by photometric estimation of 4-nitrophenol after complete alkaline hydrolysis. In the case of the oligonucleotide, covalent reactivity is introduced by modifying backbone phosphate diester linkages to triesters or fluorophosphate diesters. If needed, phosphonates can also be introduced into the backbone. However, alkoxy groups withdraw electrons poorly, with the result that the phosphorus atom will display only weak electrophilicity in this case. Arrows in the figure indicate the leaving groups in the oligo-CAL. The precursor, an H-phosphonate DNA analog (compound i), is used as an intermediate in conventional solid-phase DNA synthesis (31). After removing protecting groups with aqueous ammonia, 1 in 5 backbone H-phosphonate functionalities are converted to 4-nitrophenyl phosphonates using the appropriate amount of 4-nitrophenol (compound ii). Unreacted H-phosphonates are then oxidized with iodine to give ordinary phosphate diester linkages interspersed with the triester. For fluorophosphate CAL synthesis, the product is treated by customary DNA synthesis methods (I oxidation/aqueous NH3) and then with KF in the presence of 18-crown-6 thionyl chloride (iii). This converts the phosphate diester to fluorophosphate diester (KF will be titrated to yield 1 fluorophosphate group/5 bases). Derivitization is estimated by photometric measurement of 4-nitrophenol after alkaline hydrolysis or fluorine quantification by elemental analysis. Oligo-CAL length can be held at 30 bases. Biotin is attached at the 5'terminus of the oligo-CAL during synthesis. Although the CAL moieties are randomly positioned, their density is sufficient to afford Ab binding (minimum epitope length, 5 nucleotides). Lupus anti-ssDNA Abs display preference for poly(dT) stretches (5,24) but their specificity for individual sequences is comparatively unrestricted. Accordingly, the central region of the oligo-CA1 can be a 16-mer blanked by 7-mer random sequences on each side [$(N)_7$-$(T)_{16}$-$(N)_7$], with degeneracies in the flanks introduced using mixtures of A/T/G/C during synthesis.

VIP-CALs (see FIG. 18 for structures). VIP-CALs are derived from a truncated form of the peptide residues 7-29; VIP-CALs 6-9) or full-length VIP (VIP-CALs 1-5). A truncated sequence is desirable to avoid receptor binding [the entire VIP sequence is needed for binding by receptors; autoantibodies recognize the C-terminal half of VIP]. The CAL variants shown included backbone CALs and side chain CALs.

The synthesis and characterization of a VIP-CAL is described in Example III. In addition to phosphonate ester VIP-CALs, carbonyl CALs are useful because of their longer half-life and superior simulation of the carbonyl reaction center in the cleavage of peptide bonds by Abs. An example of a carbonyl VIP-CAL is shown in FIG. 18. The structure of this compound is based on reports that amidinophenyl pyruvate forms covalent complexes with serine proteases (32,33) similar to those of phosphonate CALs.

Key elements of phosphonate VIP-CALs are: (a) the peptidic structure, allowing noncovalent binding to the Ab paratope; (b) one (monoester) or 2 leaving groups (diester) that determine the level of chemical activity of the phosphorus, and in the case of the monoester, allow expression of a negative charge on the unesterified oxygen; and (c) the positively charged amidino group. Biotin and amino acids for conjugation to carrier proteins are incorporated at the N terminus as needed. The rate constant $k_3$ (FIG. 1) depends on the covalent reactivity of the phosphorus atom. CALs with different $k_3$ values are useful for different purposes. Rapid and complete inhibition of Abs is achieved by highly reactive CALs with large $k_3$ values. Weakly covalent CALs (low $k_3$) react with strong Ab nucleophiles without reacting at weak nucleophiles. In the reaction scheme of FIG. 1, a VIP-CAL that fully mimics the reversible binding of VIP with the Ab will possess an equilibrium constant $K_i$ $(k_2/k_1)$ equivalent to $K_d$ of VIP. Additionally, as the negatively charged monoester CAL mimics the noncovalent reactivity of the transition state, the Ki will reflect some component of transition state binding energy.

A phosponate diester can serves as the covalent moiety, and a positively charged amidino group can optionally be placed on the N terminal side of the phosphonate, which is a K/R mimetic The N-terminal biotin allows detection of Ab binding. VIP-CALs 3 and 6 contains the amidino-phosphonate diester incorporated within the peptide backbone in place of K20. The peptide flanks are desirable to more fully capture noncovalent paratope-epitope interactions. VIP-CAL 3-5 and 7-9 contain the phosphonate located on NH2 side chains of the 3 K residues in VIP. Standard chemical synthesis techniques are applied (1-3,34). Backbone VIP-CALs are prepared by synthesizing the phosphonate diester unit in solution initially. The protected peptidyl phosphonate is coupled to the C-terminal peptide fragment prepared by solid phase synthesis using an N-terminal glycolate residue, and the product is treated with anhydrous TFA to give the desired CALs. Side chain CALs are prepared by conjugating diphenyl amino(4-amidinophenyl) methanephosphonate and VIP (or biotinylated VIP) using the homo-bifunctional linker, bis-sulfosuccinimidyl suberate, followed by separation of individual isomers labeled at different Lys residues by HPLC. CAL identity is confirmed by mass spectroscopy/NMR. The position of the acylated Lys is determined by MS/MS analysis. The main pitfall in the syntheses is of side reactions at unintended groups. This is minimized by utilizing appropriate protecting groups.

The pyruvyl VIP-CAL is structurally similar to 3. Preparation of this compound does not present difficulties as the necessary reaction between the pyruvate carboxyl and side chain amine of Lys should proceed much like the analogous reaction for VIP-CAL 4.

Study of these CALs allows examination of the flexibility enjoyed by Ab nucleophiles. The presence of peptides on both flanks of the phosphonate may be desirable to capture noncovalent paratope-epitope interactions. The region of VIP on the C terminal side of the phosphonate (residues 22-28) is suggested to furnish an important energetic contribution in Ab-VIP recognition.

Covalent Ab Binding.

The following steps are taken to validate CAL design: (a) determine the magnitude and characteristics of covalent CAL binding by lupus Abs; and (b) determine whether CAL binding induces loss of Ab binding to DNA or VIP. Polyclonal Abs are employed for most validation studies, as diverse anti-DNA/anti-VIP Abs found in vivo must be targeted. In some situations, use of monoclonal Abs is needed, e.g., to accurately determine kinetic constants. Pooled IgG from the following sources is studied: (a) lupus patients diagnosed according to the Am Rheumatol Soc criteria along with control subjects (N=20); (b) 8 wk old MRL/lpr mice and control MRL/++ mice (N=8); (c) 20 week old MRL/lpr mice and control MRL/++ mice (N=8). IgG purified on protein G-Sepharose is treated with increasing CAL concentrations. Covalent binding is determined by SDS-electrophoresis and staining of biotinylated bands in blots using streptavidin-peroxidase and a chemiluminescent substrate. In the case of DNA-CALs, mass determination of the complexes is not possible, but unambiguous separation of Ab-complexed and free DNA-CAL will occur. Controls include treatment with excess DFP (competitor for binding at the Ab nucleophile) and excess DNA or VIP (noncovalent competitor; this will show that CAL binding occurs at the active site). The reaction is quantified by densitometry using a Biorad imager (linear over 5 log orders of biotin).

Noncovalent binding at the antigenic epitopes allows superior VIP-CAL and DNA-CAL binding to their respective specific Ab populations compared to control Abs. To confirm that ambiguities related to the polyclonal nature of the IgG are not a factor, the CALs will be analyzed using at least one monoclonal Ab to DNA and VIP (e.g., clone BV04-01 for the DNA-CAL; clone c23.5 for VIP-CALs). CAL binding and inhibition of conventional enzymes will be studied similarly to confirm CAL selectivity (serine acylases, e.g., trypsin; DNA cleaving enzymes, e,g, DNase I). Kitz-Wilson plots of covalent binding as a function of time and CAL concentration (35) allows estimation of Ki (strength of noncovalent binding) and k3 (strength of nucleophilic reactivity). Irreversibility is established by protein G chromatography of Ab-CAL complexes (to remove free CALs) followed by reanalysis of DNA and VIP binding. Loss of binding activity indicates covalent Ab inhibition. Standard ELISA methods are employed for this purpose, in which the antigen (DNA, VIP) is immobilized on the solid phase and bound Abs are determined using peroxidase conjugated anti-human/mouse IgG. ELISA studies are done using streptavidin plates coated with synthetic VIP/oligonucleotide biotinylated at the N terminus and 5' end, respectively. dsDNA and ssDNA from calf thymus are immobilized directly on the plates (ssDNA prepared as in ref 36).

Use of previously employed diphenyl phosphonate diesters in the dsDNA-CAL ensures that the covalent reactivity of this compound is sufficient to probe anti-DNA nucleophilicity. The oligo-CAL contains phosphate triesters/fluorophosphate diesters in its backbone, the covalent reactivity of which should be comparable to diphenyl phosphonates and DFP.

VIP-CAL design and synthesis is modeled on our previous studies on polypeptide CALs. As diverse Abs present in lupus are targeted, any one CAL may not be sufficient to obtain complete or near-complete covalent Ab blockade. Thus, it may be necessary to use mixtures of the CALs in subsequent studies. High affinity binding due to noncovalent paratope-epitope recognition will minimize CAL reactivity with irrelevant Abs and enzymes.

3. CAL Effects on Antibody Biological Activity.

Ab DNA-CAL inhibition of Ab cytotoxicity. Lupus anti-DNA Abs can traverse membranes and induce apoptosis. Cytotoxic effects of anti-DNA Abs treated with DNA-CALs can be assessed using renal tubular cell line (LLC-PK) and an MTT assay (37). The IgG source is lupus patients, healthy human subjects, 8 wk old MRL/lpr mice, 20 week old MRL/lpr mice and control MRL/++ mice at equivalent ages. In addition, at least one monoclonal L chain is analyzed to exclude confounding effects due to Ab heterogeneity (e.g., clone KM38). IgG is incubated in diluent or various concentrations of DNA-CALs and control DNA (devoid of the CAL moiety), free ligand is removed as in Aim1, and the mixtures mixed with cells cultured in 24-well plates. Cytotoxicity is quantified after 24 h. Control wells receive no Ab. Confirmation is obtained by microscopic inspection after staining with propidium iodine (dead cells) and Hoechst 33342 (dead+live cells). Additional studies are done by treating the cells with Abs and CALs without removal of free CALs—these are needed to show that the CALs do not themselves exert a cytotoxic effect, and that a beneficial effect is obtained when the CALs and the cells compete with each other for Ab binding. Direct cytotoxic effects of lupus Abs in the kidney are generally conceived to involve Ab binding to DNA-containing antigens and/or cross-reactive protein antigens, followed by penetration of the cell/nuclear membranes by pathways that are remain to be defined fully. Covalent Ab engagement by CALs should permanently knock out the antigen binding function. Thus, unless an Fc effector function is involved, CAL-bound Abs are anticipated to be devoid of cytotoxic effects (note that there is no source of complement or ADCC-competent cells in the cultures, minimizing the likelihood of Fc involvement).

DNA-CAL inhibition of kidney antigen recognition. To the extent that antigen recognition is the mechanism for deposition of lupus Abs in the kidney, covalent blockade of the Abs by DNA-CALs should result in loss of Ab binding to kidney sections. The quantitative importance of antigen recognition versus Fc receptor binding as mechanisms for Ab deposition in the lupus kidney is not known. Kidney cryostat sections from wild type MRL/++ mice as well as MRL/lpr mice are analyzed, as increased nucleosome formation in lupus is suggested to allow increased opportunity for anti-DNA Ab binding (38). Immunofluorescence methods are employed to determine binding of control IgG and IgG treated with DNA-CALs (IgG from 8 wk old MRL/lpr mice, 20 week old MRL/lpr mice and equivalently aged control MRL/++ mice; anti-mouse IgG-FITC conjugate). To determine whether residual binding by CAL-derivitized Abs involves Fc receptors, the binding studies are repeated in the presence of excess mouse Fc fragments (prepared by papain digestion/protein-A chromatography).

Beneficial effects of DNA-CALs in vivo. The clinical course of lupus in MRL/lpr mice shares similarities with human lupus. Many hallmarks of human lupus are observed in these mice, e.g., formation of Abs to various autoantigens, kidney damage, proteinuria, multi-organ involvement and heightened T helper cell activity. Abs to DNA and VIP appear spontaneously in the serum of MRL/lpr mice. Thus, the MRL/lpr model is a suitable first approximation to determine the potential ameliorative effects of CALs. DNA-CALs can be administered to MRL/lpr mice at two ages: 8 wks and 14 wks. Serum Abs to certain autoantigens begin to appear at 8 wks and most Abs characteristic of lupus are detected by 14 wks, when kidney damage is overt. Mortality increases rapidly after age 16 wks, and 50% mortality occurs at 22-24 wks. Initially, it is appropriate to study 3 intravenous administrations of DNA-CALs, e.g., at 2 week intervals. Control mice receive diluent. Groups of 8 mice each in the 8 wk cohort are euthanized at 2 wk intervals for detailed analysis until 26 wks (8 mice/group; 10 groups, including the 8 wk baseline group). Similarly, groups of 8 mice each in the 14 wk cohort are euthanized at 2 wk intervals until 26 wks (7 groups including the 14 wk baseline). In addition, eye bleeds are drawn 1 day after each CAL administration for study of acute CAL effects on Ab binding and catalytic activities (see below). CAL doses are adjusted based on in vitro efficacy data (assuming a distribution volume of ~10 ml), which are predicted to indicate that nM CAL concentrations are sufficient in inhibit the anti-DNA Abs. A mixture of the dsDNA-CAL/oligo-CAL is studied initially to obtain inhibition of diverse Ab subtypes. Subsequent studies include analysis of multiple concentrations of the CALs administered separately as needed. Serum anti-dsDNA/ssDNA titers are measured by ELISA. Reduced anti-DNA titers are predicted (unless anti-DNA Ab replenishment occurs more rapidly than their covalent blockade). Residual DNA-CAL binding activities of serum IgG is measured as before. The DNA-CALs are not anticipated to serve as immunogens for additional anti-dsDNA Ab synthesis, as elicitation of these Abs requires coimmunization with DNA binding proteins and adjuvant (39).

Anti-DNA immune responses are theorized to initiate lupus (e.g., 40). For example, Ab responses to several other autoantigens may be explained by 'epitope spreading' phenomena, in which the presence of cells sensitized to DNA can facilitate Ab responses to proteins associated with DNA. Thus, it is useful to assess the level of the overall immune responses in DNA-CAL treated mice. This is done by measuring total levels of serum immune complexes and rheumatoid factor by standard methods. Study of glomerular damage is by histological examination by an expert pathologist using standard procedures for assessing human biopsies (WHO classification, semiquantitative index), paying attention to the level of cellular hypertrophy, glomerular sclerosis/scarring, excessive extracellular matrix, and presence of inflammatory cells. Proteinuria is read with Chemstrips. Ab and C3 deposition in kidney sections will be by staining with anti-mouse Ig/anti-mouse C3 labeled with FITC, with consideration given to the magnitude and site of staining (e.g., basement membrane, subepithelial spaces, cell surfaces, nuclei). The general health and mortality is recorded by daily inspection of the mice. Once initial data are in hand, repeat experiments can be carried out as needed with sufficient numbers of mice for the study to be statistically powered to enable detection of 20% improvement in mortality.

VIP-CAL effect on cytokine synthesis. VIP exerts important effects at several critical steps in T cell differentiation, including cytokine synthesis and expression of membrane proteins (e.g., Fas ligand expression, costimulatory protein B7.2). The beneficial effect of VIP in suppressing autoimmune responses is known (15). VIP-CALs are studied for the ability to correct changes in T cell cytokine synthesis induced by anti-VIP Abs. T cells from transgenic mice overexpressing the type 2 VIP receptor (VPACR2) are employed as in previous studies (41). T-helper responses are associated with VPACR2 upregulation, which makes this experimental system directly relevant to lupus. Readily detectable changes in cytokine synthesis accompanied by depletion of VIP are observed by treating the VPACR2 overexpressing T cells with an anti-VIP Ab. T cells isolated from the mice using anti-CD4 magnetic beads are cultured for 96 h with VIP-CALs mixed with anti-VIP Abs (monoclonal c23.5 IgG and isotype-matched nonimmune IgG: IgG from 8 wk old MRL/lpr mice, 20 week old MRL/lpr mice and equivalently aged control MRL/++ mice). Anti-VIP concentrations as small as 10 nM are sufficient to induce decreased secretion of IFN-γ and decreased secretion of IL-4. ELISA methods are used to measure IFN-γ and IL-4 secretion by the T cells. As before, removal of free CAL prior to Ab treatment of the cells allows determination of irreversible VIP-CAL effects. Anti-VIP Ab treatment depletes VIP in T cells, which is thought to disturb autocrine T cell regulation by the peptide. Thus, it is useful to measure the ability of VIP-CALs to restore VIP levels to control levels in the Ab treated cells (by radioimmunoassy of total VIP following dissociation of Ab-VIP complexes at acid pH as in previous studies, ref 18,42). Direct interaction of VIP-CALs with lymphocyte VIP receptors is precluded, as receptor binding requires the entire sequence of VIP (the CALs contain truncated VIP).

Beneficial effects of VIP-CAL in vivo. In vivo VIP-CAL studies are designed essentially as described for the DNA-CALs. Key features are: (a) Serum anti-VIP Abs binding activities are measured by ELISA and radioassay, respectively, following VIP-CAL administration; (b) Total VIP levels in serum and spleen extracts are determined by radioimmunoassay (18,42); (c) serum levels of total IgG, anti-DNA Abs, rheumatoid factor and immune complexes are measured for immunochemical correlation; (d) Flow cytometric determination of T cell subpopulations (CD4+, CD8+, activated CD4+ cells, total B cells (CD19) and NK cells (DX1.1) is done—reduced numbers of activated T helper cells will indicate the overall beneficial effects of VIP-CAL treatment; and (f) kidney histology, Ab deposition and survival data is obtained. As in the case of the DNA-CAL studies, the VIP-CALs can be analyzed for beneficial effects separately or a mixture of VIP-CALs based on the in vitro efficacy data can be analyzed.

Even if CAL half-life is on the order of hours, observation of beneficial effects can be anticipated. Provided sufficient initial CAL concentrations are obtained, the reaction with Abs should be complete quickly. Depending on the results of MRL/lpr studies, other lupus-prone mouse strains can be analyzed prior to consideration of humans studies (NZB/W F1; BXSB).

4. Tolerance Induction.

Antigen-specific covalent receptor engagement has become feasible by the development of LaCALs. Covalent BCR and TCR occupancy holds the potential of inducing antigen-specific tolerance of the B and T cells by driving these cells into apoptosis. If needed, this effect of LaCALs can be supplemented by including within these compounds a toxin, which will kill the targeted cells selectively, without causing systemic side effects. Attachment of toxins such as pseudomomas endotoxin and ricin to various proteins has been described in detail in the literature and can be accomplished by protein chemistry conjugation or genetic fusion techniques (43).

BCR covalent reaction with hapten CALs. hapten CALs such as compound I (FIG. 19) react irreversibly with nucleophilic sites in conventional serine proteases and Abs (3,35, 44-47). Methods for synthesis of this compound, preparation of B cells from mice, flow cytometric analysis of binding to the cells and electrophoretic measurement of covalent binding to Ig subunits are described in refs 3,35,48. To evaluate the nucleophilic reactivity expressed on the surface of B cells in the preimmune repertoire (viz., the repertoire developed spontaneously without purposeful immunological challenge), viable splenocytes from BALB/c mice were treated with hapten CAL I. The control compound II is identical in structure to hapten CAL I, except that the phosphonate group is not esterified, which results in loss of covalent reactivity with nucleophilic residues (3,35). Treatment with hapten CAL I resulted in staining of most of cells at levels greater than compound II, with a minority of the cells displaying intense staining (11±2, N 3 experiments; determined by counting 400 lymphocytes using a UV microscope). All of the hapten CAL I-stained cells displayed lymphocytic morphology, with no evident staining of monocytes or the occasional basophil. No loss of viability of the cells was evident following incubation with hapten CAL I or compound II, as determined by trypan blue exclusion. Flow cytometry confirmed the microscopy results. Seventy nine percent of the hapten CAL I-treated cells displayed fluorescence intensities exceeding the compound II-treated cells, including a minority subpopulation with very high fluorescence intensity (14%; subpopulation 2 in FIG. 20A). In 3 repeat experiments, the proportion of hapten CAL I-stained cells that were positive for the B cell marker CD19 was 82±4% (FIG. 20B). Deconvolution microscopy indicated that the fluorescence pattern due to hapten CAL I binding was nearly coincident with the anti-CD19 Ab fluorescence pattern (FIG. 20C-E). Most of the CAL fluorescence was restricted to the surfaces of the B cells (FIG. 20F).

Figure 21:
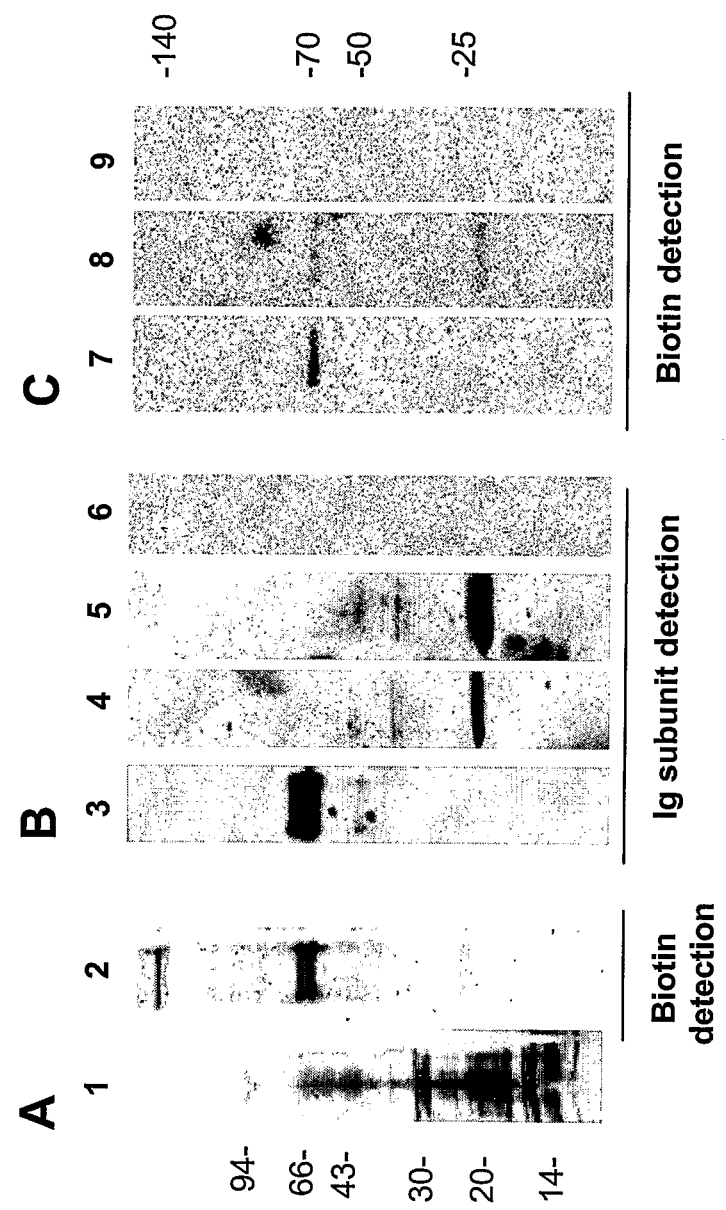

To identify the nucleophilic molecules on the cell surface, purified B cells were labeled with hapten CAL I, detergent extracts of the cells were boiled and then analyzed by SDS-electrophoresis. Only limited hapten CAL-containing proteins were evident (FIG. 21A). As expected, silver staining revealed the presence of heterogeneous species, reflecting the complex protein constitution of the cells. The mass of the predominant hapten CAL adduct band was 70 kD, and this band was stainable by anti-μ chain Ab (FIG. 21B). Smaller amounts of hapten CAL-containing bands were evident at 25 kD, 40 kD, 50 kD, 55-60 kD, 90-135 kD and 140 kD. The bands at 55-60 kD and 140 kD were stainable by the anti-μ Ab, and the bands at 25 kD and 50 kD were stainable with anti-κ/λ Ab. The anomalous μ and κ/λ bands at mass range different from the full-length monomer proteins presumably represent unreduced oligomers, breakdown products and truncated B cell Ig products, as also observed in previous studies of secreted Abs and B cell extracts (22-24). The minor bands at 40 kD and 90-135 kD that were not stainable with Abs to μ, γ, κ/γ (FIG. 21 B) and δ chains (not shown) presumably represent non-Ig proteins. No hapten CAL-containing adduct corresponding to Ig γ chains were detected. Immunoblotting of the cell extracts identified a band at 50 kD stainable with anti-γ Ab, but the band was visible only in highly overexposed gels, suggesting that only small amounts of γ chains were present in the extract.

Confirmation that the hapten CAL I adducts contain Ig subunits was by affinity chromatography on columns of immobilized Abs to μ, δ, γ and κ/λ chains followed by SDS-electrophoresis (FIG. 21C). hapten CAL-containing μ and κ/λ bands were evident in eluates from the anti-μ and anti-κ/λ columns. Recovery of hapten CAL-containing μ chains in the eluate from the anti-κ/λ column can be explained by the presence of disulfide bonded light and heavy chain complexes on the cell surface. No hapten CAL-containing bands were evident in eluates from the anti-γ and anti-δ columns (not shown), but this can not be interpreted to reflect deficient γ/δ chain nucleophilic reactivity, as these proteins are expressed only at low levels in B cells from immunologically naïve mice. To determine the proportion of overall cellular hapten CAL staining attributable to complexation with Ig subunits, the B cell extract was fractionated on a single affinity column composed of immobilized Abs to μand κ/λ chains. Eighty percent of the hapten CAL content of the cells was adsorbed by the column (not shown), determined by densitometry of the biotin-containing bands in the unbound fraction and the extract loaded on the column. Taken together, these observations indicate that most of the hapten CAL staining of intact B cells is attributable to irreversible binding to surface Ig, with the μ chain accounting for most of the covalent reactivity.

Antigen-specific BCR covalent labeling. For validation of antigen-specific covalent reactivity of LaCALs, B cells are prepared from spleens of MRL/lpr mice. These mice synthesize specific autoantibodies to VIP (16,17) and DNA (23). If needed, B cells can also be prepared from mice immunized with VIP and dsDNA (induction of Abs to DNA is possible when DNA is complexed to proteins such as histone). Purified B cells from spleens will be obtained from the MRL/lpr mice (10-12 wks age) along with the control non-autoimmune strain negative for the autoantibodies (MRL/++) using a negative selection kit (Miltenyi).

The magnitude of B cell VIP-CAL and DNA-CAL reactivity and the proportion of reactivity attributable to cell surface Ig is analyzed. The LaCALs along with hapten CAL are analyzed to determine the optimal structure affording antigen-specific BCR covalent binding. B cells are incubated with the CALs for a suitable length of time, the cells are washed and then extracted with detergent (9 mM CHAP). Ig subunits are purified by affinity chromatography using immobilized Abs to μ/δ/α/γ/ε/κ/λ/surrogate L chains (surrogate L chains are components of the pre-BCR expressed on immature B cell). Control affinity columns consist of immobilized Abs to an irrelevant protein. CAL-adducts are identified by biotin detection on reducing SDS-gels. Concentrations of individual Ig subunits are determined by conventional ELISAs using immobilized Abs to Ig subunits (with the authentic proteins as standards). Data are expressed as band intensities/Ig concentration. To confirm band identity, the blots are stained with specific peroxidase conjugated Abs to the Ig subunits. As in previous studies, crude cell extracts of cell-CAL reaction mixtures are also analyzed by SDS-PAGE (without prior affinity chromatography—this is needed to compute the proportion of labeling attributable to the BCR). Inclusion of VIP in the reaction of VIP-CAL with B cells will help determine the extent to which VIP-CAL binding depends on noncovalent peptide interactions. Inhibition of VIP-CAL binding by DFP helps show that Ig binding occurs at activated nucleophiles. Similar studies are done using DNA as inhibitor of DNA-CAL binding to demonstrate antigenic specificity.

Kinetic analyses of the adduct formation is to obtain values of $K_i$ and $k_3$ (35). These provide objective assessment of the contribution of noncovalent and nucleophilic reactivity, respectively.

Previous immunochemical analyses indicates that about ~80% of the hapten CAL adducts in B cell extracts are attributable to Ig subunits. Therefore, certain properties related to related to BCR nucleophilicity can be determined using intact cells. Phycoerythrin conjugated Abs to CD19 are used to identify B cells. Cells are maintained in viable state until incubation with CALs and streptavidin-FITC is complete. Formalin fixed cells are examined by UV microscope. Viability is determined by trypan blue exclusion before/after CAL incubation. Confocal microscopy is done using an Olympus microscope equipped with deconvolution capability. Frozen spleen sections are analyzed for CAL staining to define any distinctive morphological location occupied by the CAL-labeled B cells [follicular cells tend to be immature B cells; marginal zone cells are more mature]. Flow cytometry of cells stained with Abs to μ/δ/α/γ/ε/κ/λ and surrogate L chains identifies the preferred Ab class synthesized by the most CAL reactive cells.

Additional useful information is gained as to the B-1/B-2 nature of CAL-stainable cells as follows. B-1 cells [CD45 (B220$^{lo}$), IgM$^{hi}$, CD23$^-$, CD43$^+$, IgD$^{lo}$] tend to be responsible for autoreactive Ab production. As VIP and DNA are autoantigens, preferential production of nucleophilic Abs to these antigens is likely. The spleen does not contain large numbers of B-1 cells/early B cell progenitors. Peritoneal cells, which are richer in B-1 cells, can be analyzed further if needed.

Cellular stimulation by CALs in vitro. Cultured cells will be stimulated with the hapten CALs, VIP-CAL or DNA-CAL (increasing concentration; varying length of time). Compound 3, which is devoid of a covalently reactive group, is the control. An additional control is the treatment of cells with anti-IgM Ab. The following assays are done. Cellular DNA synthesis is measured using a BrDU incorporation kit. Controls include cells incubated with the nucleotide in the absence of CALs. To determine whether the CALs can commit the cells to Ab synthesis, the cells will be washed following in vitro treatment with the CALs, maintained in culture without the antigen, and the number of antibody forming cells will be determined by flow cytometry (staining with Abs to μ/δ/γ).

As BCR saturation with ordinary antigens is known to drive cells into apoptosis, the CALs hold the potential of inducing cell death leading to tolerance. The is tested following CAL treatment by flow cytometry by the TUNEL method (TdT-mediated dUTP Nick End Labeling; using fluorescein dUTP to label strand breaks). Instrument calibration, side and forward scatter, and compensation values are established and reconfirmed periodically. Anti-Fas Ab will be employed as the positive control. In each assay, specificity of the effects induced in vitro is indicated by responses to VIP-CAL or DNA-CAL at levels exceeding the hapten CAL. Comparisons of the effects of VIP-CAL and DNA-CAL with those of VIP and DNA devoid of the CAL moiety, respectively, will serve as an index of effects attributable to the covalent binding reaction.

In vivo tolerance induction. Covalent LaCAL binding by the B cells is expected to induce immunological tolerance. Previously, B cell anergy induced by saturating surface Ig with excess antigen has been documented (49,50). Mice treated in vivo with VIP-CALs and DNA-CALs as described above will analyzed for cellular reactivity to VIP and DNA, respectively.

Essentially, the number of VIP binding B cells and DNA binding B cells will be determined in splenocyte preparations of mice that have received the corresponding LaCAL administrations. This is done by flow cytometry using biotinylated VIP, dsDNA and single stranded oligonucleotide probes. Streptavidin-peroxidase is used to identify VIP and DNA bound to the cells. Staining for anti-CD19 conjugated to phycoerthyrin identifies the B cell subpopulation. Confirmatory studies are done using ELISASPOT methods, in which B cells are stimulated by VIP or DNA in vitro to determine downregulation of Ab synthetic responses attributable to in vivo CAL treatments.

Conventional methods to target secreted Abs and BCRs with ordinary autoantigens are limited by the fact that very high affinity analogs must be employed to out-compete excess the endogenous autoantigen. Reversible binding to the Abs will eventually result in dissociation of the autoantigen analog, regenerating active Abs. Covalent binding LaCALs, on the other hand, are intended to permanently engage the Ab active sites. Permanent (covalent) BCR engagement is analogous to saturation with excess antigen, which is well known to induce B cell clonal apoptosis and anergy.

In the examples cited above, the LaCALs are unlikely to serve as immunogens. Elicitation of anti-dsDNA is generally very difficult. Similarly, VIP administration does not stimulate anti-VIP synthesis, except when the peptide is derivitized with carrier proteins and injected in conjunction with strong adjuvants.

References

1. Nishiyama Y, Bhatia G, Bangale Y, Planque S, Mitsuda Y, Taguchi H, Karle S, Paul S. Toward selective covalent inactivation of pathogenic antibodies: a phosphate diester analog of vasoactive intestinal peptide that inactivates catalytic autoantibodies. J Biol Chem 2004 Feb. 27; 279(9): 7877-83.
2. Paul S, Planque S, Zhou Y X, Taguchi H, Bhatia G, Karle S, Hanson C, Nishiyama Y. Specific HIV gp120-cleaving Antibodies Induced by Covalently Reactive Analog of gp120. J Biol Chem 2003 May 30; 278(22):20429-20435.
3. Planque S, Taguchi H, Burr G, Bhatia G, Karle S, Zhou Y X, Nishiyama Y, Paul S. Broadly Distributed Chemical Reactivity of Natural Antibodies Expressed in Coordination with Specific Antigen Binding Activity. J Biol Chem 2003 May 30; 278(22):20436-20443.
4. Nossal G J. B lymphocyte physiology: the beginning and the end. Ciba Found Symp. 1997; 204:220-30; discussion 230-1.
5. Stollar B D. Molecular analysis of anti-DNA antibodies. FASEB J. 1994 Mar. 1; 8(3):337-42.
6. Stemmer C, Richalet-Secordel P, van Bruggen M, Kramers K, Berden J, Muller S. Dual reactivity of several monoclonal anti-nucleosome autoantibodies for double-stranded DNA and a short segment of histone H3. J Biol. Chem. 1996 Aug. 30; 271(35):21257-61.
7. Groggel, G. (1999) Kidney damage in autoimmune disease. In: S. Paul (Ed) Autoimmune Reactions. Humana Press, Totowa, p. 249-268.
8. Yanase, K. and Madaio, M. (1999) Cellular entry and nuclear localization of anti-DNA antibodies. In: S. Paul (Ed) Autoimmune Reactions. Humana Press, Totowa, p. 293-304.
9. Alarcon-Segovia D, Llorente L. Antibody penetration into living cells. IV. Different effects of anti-native DNA and anti-ribonucleoprotein IgG on the cell cycle of activated T gamma cells. Clin Exp Immunol. 1983 May; 52(2):365-71.
10. Raz E, Ben-Bassat H, Davidi T, Shlomai Z, Eilat D. Cross-reactions of anti-DNA autoantibodies with cell surface proteins. Eur J Immunol. 1993 February; 23(2):383-90.
11. Zack, D. J. and Weisbart, R. H. (1999) Cell and nuclear penetration by autoantibodies. In: S. Paul (Ed) Autoimmune Reactions. Humana Press, Totowa, p. 305-319.
12. Shuster A M, Gololobov G V, Kvashuk O A, Bogomolova A E, Smirnov I V, Gabibov A G. DNA hydrolyzing autoantibodies. Science. 1992 May 1; 256(5057):665-7.
13. Suchkov S V. Comparative study of catalytic (DNA-hydrolyzing) and cytotoxic properties of anti-dna autoantibodies. Bull Exp Biol Med. 2001 April; 131(4):353-5.
14. Matsuzaki Y, Hamasaki Y, Said S I. Vasoactive intestinal peptide: a possible transmitter of nonadrenergic relaxation of guinea pig airways. Science. 1980 Dec. 12; 210(4475): 1252-3.
15. Delgado M, Abad C, Martinez C, Leceta J, Gomariz R P. Vasoactive intestinal peptide prevents experimental arthritis by downregulating both autoimmune and inflammatory components of the disease. Nat. Med. 2001 May; 7(5):563-8.
16. Bangale Y, Cavill D, Gordon T, Planque S, Taguchi H, Bhatia G, Nishiyama Y, Arnett F, Paul S. Vasoactive intes- 17. Bangale Y, Karle S, Planque S, Zhou Y X, Taguchi H, Nishiyama Y, Li L, Kalaga R, Paul S. VIPase autoantibodies in Fas-defective mice and patients with autoimmune disease. FASEB J 2003 April; 17(6):628-35.
18. Paul S, Said S I, Thompson A B, Volle D J, Agrawal D K, Foda H, de la Rocha S. Characterization of autoantibodies to vasoactive intestinal peptide in asthma. J Neuroimmunol 1989 July; 23(2):133-42.
19. Ganea D. Regulatory effects of vasoactive intestinal peptide on cytokine production in central and peripheral lymphoid organs. Adv Neuroimmunol. 1996; 6(1):61-74.
20. Dorsam G, Voice J, Kong Y, Goetzl E J. Vasoactive intestinal peptide mediation of development and functions of T lymphocytes. Ann N Y Acad Sci. 2000; 921:79-91.
21. Goetzl E J, Voice J K, Shen S, Dorsam G, Kong Y, West K M, Morrison C F, Harmar A J. Enhanced delayed-type hypersensitivity and diminished immediate-type hypersensitivity in mice lacking the inducible VPAC(2) receptor for vasoactive intestinal peptide. Proc Natl Acad Sci USA. 2001 Nov. 20; 98(24):13854-9.
22. Bracci-Laudiero L, Aloe L, Stenfors C, Theodorsson E, Lundeberg T. Development of systemic lupus erythematosus in mice is associated with alteration of neuropeptide concentrations in inflamed kidneys and immunoregulatory organs. Neurosci Lett. 1998 May 29; 248(2):97-100.
23. Blatt N B, Glick G D. Anti-DNA autoantibodies and systemic lupus erythematosus. Pharmacol Ther. 1999 August; 83(2):125-39.
24. Lefkowith J B, Di Valerio R, Norris J, Glick G D, Alexander A L, Jackson L, Gilkeson G S. Murine glomerulotropic monoclonal antibodies are highly oligoclonal and exhibit distinctive molecular features. J. Immunol. 1996 Aug. 1; 157(3):1297-305.
25. Barbas S M, Ditzel H J, Salonen E M, Yang W P, Silverman G J, Burton D R. Human autoantibody recognition of DNA. Proc Natl Acad Sci USA. 1995 Mar. 28; 92(7):2529-33.
26. Winkler T H, Jahn S, Kalden J R. IgG human monoclonal anti-DNA autoantibodies from patients with systemic lupus erythematosus. Clin Exp Immunol. 1991 September; 85(3):379-85.
27. Ackroyd P C, Cleary J, Glick G D. Thermodynamic basis for sequence-specific recognition of ssDNA by an autoantibody. Biochemistry. 2001 Mar. 6; 40(9):2911-22.
28. Herrmann M, Winkler T H, Fehr H, Kalden J R. Preferential recognition of specific DNA motifs by anti-double-stranded DNA autoantibodies. Eur J. Immunol. 1995 July; 25(7):1897-904.
29. Deleted in revision.
30. Straub K, Kanne D, Hearst J E, Rapoport H. Isolation and characterization of pyrimidine-psoralen-pyrimidine photoadducts from DNA. J Am Chem Soc 1982; 104:6754-6764.
31. Froehler B C, Ng P G, Matteucci M D. Synthesis of DNA via deoxynucleoside H-phosphonate intermediates. Nucleic Acids Res. 1986 Jul. 11; 14(13):5399-407.
32. Walter J, Bode W. The X-ray crystal structure analysis of the refined complex formed by bovine trypsin and p-amidinophenylpyruvate at 1.4 A resolution. Hoppe Seylers Z Physiol Chem. 1983 August; 364(8):949-59.
33. Chen Z, Li Y, Mulichak A M, Lewis S D, Shafer J A. Crystal structure of human alpha-thrombin complexed with hirugen and p-amidinophenylpyruvate at 1.6 A resolution. Arch Biochem Biophys. 1995 Sep. 10; 322(1):198-203.
34. Taguchi H, Burr G, Karle S, Planque S, Zhou Y X, Paul S, Nishiyama Y. A mechanism-based probe for gp120-Hydrolyzing antibodies. Bioorg Med Chem Lett 2002 Nov. 4; 12(21):3167-70.
35. Nishiyama Y, Taguchi H, Luo J Q, Zhou Y X, Burr G, Karle S, Paul S. Covalent reactivity of phosphonate monophenyl esters with serine proteinases: an overlooked feature of presumed transition state analogs. Arch Biochem Biophys 2002 Jun. 15; 402(2):281-8.
36. Pisetsky D S, Gonzalez T C. The influence of DNA size on the binding of antibodies to DNA in the sera of normal human subjects and patients with systemic lupus erythematosus (SLE). Clin Exp Immunol. 1999 May; 116(2):354-9.
37. Tawfik D S, Chap R, Green B S, Sela M, Eshhar Z. Unexpectedly high occurrence of catalytic antibodies in MRL/lpr and SJL mice immunized with a transition-state analog: is there a linkage to autoimmunity? Proc Natl Acad Sci USA 1995 Mar. 14; 92(6):2145-9.
38. Licht R, van Bruggen M C, Oppers-Walgreen B, Rijke T P, Berden J H. Plasma levels of nucleosomes and nucleosome-autoantibody complexes in murine lupus: effects of disease progression and lipopolysacharide administration. Arthritis Rheum. 2001 June; 44(6):1320-30.
39. Desai D D, Marion T N. Induction of anti-DNA antibody with DNA-peptide complexes. Int Immunol. 2000 November; 12(11):1569-78.
40. Napirei M, Karsunky H, Zevnik B, Stephan H, Mannherz H G, Moroy T. Features of systemic lupus erythematosus in Dnase1-deficient mice. Nat. Genet. 2000 June; 25(2):177-81.
41. Voice, J., Dorsam, G., Paul, S., Harmar, A. J. and Goetzl, E. J. CD4+ T Cell-Dependent Cytokine-Mediated Deviation of Hypersensitivity by the Inducible Type II Receptor (VPAC2) for Vasoactive Intestinal Peptide (VIP). 2002 Experimental Biology Meeting, Apr. 20-24, 2002, New Orleans, La.
42. Paul S. Catalytic activity of anti-ground state antibodies, antibody subunits, and human autoantibodies. Appl Biochem Biotechnol. 1994 May-June; 47(2-3):241-53; discussion 253-5.
43. Paul, S. Protein engineering. In Molecular Biotechniques. Ed., Walker J. (Humana Press, Totowa, N.J.). Chapter 43, pp 547-566, 1998.
44. Oleksyszyn J, Powers J C. Amino acid and peptide phosphonate derivatives as specific inhibitors of serine peptidases. Methods Enzymol 1994; 244:423-41.
45. Sampson N S, Bartlett P A. Peptidic phosphonylating agents as irreversible inhibitors of serine proteases and models of the tetrahedral intermediates. Biochemistry 1991 Feb. 26; 30(8):2255-63.
46. Paul S, Tramontano A, Gololobov G, Zhou Y X, Taguchi H, Karle S, Nishiyama Y, Planque S, George S. Phosphonate ester probes for proteolytic antibodies. J Biol Chem 2001 Jul. 27; 276(30):28314-20.
47. Kolesnikov A V, Kozyr A V, Alexandrova E S, Koralewski F, Demin A V, Titov M I, Avalle B, Tramontano A, Paul S, Thomas D, Gabibov A G, Friboulet A. Enzyme mimicry by the antiidiotypic antibody approach. Proc Natl Acad Sci USA 2000 Dec. 5; 97(25):13526-31.
48. Planque S, Bangale Y, Song X T, Karle S, Taguchi H, Poindexter B, Bick R, Edmundson A, Nishiyama Y, Paul S. Ontogeny of proteolytic immunity: IgM serine proteases. J Biol Chem, in press (published online ahead of print on Jan. 15, 2004, as 10.1074/jbc.M312152200).

49. Goodnow C C. Glimpses into the balance between immunity and self-tolerance. Ciba Found Symp 1997; 204:190-202; discussion 202-207.

50. Nossal G J. Clonal anergy of B cells: a flexible, reversible, and quantitative concept. J Exp Med. 1996 May 1; 183(5): 1953-6.

51. Kohler H, Paul S. Superantibody activities: new players in innate and adaptive immune responses. Immunol Today 1998; 19:221-227.

EXAMPLE IV

Inhibition of Factor VIII Abs and Induction of Tolerance to Factor VIII

Abs to Factor VIII (FVII) are the unambiguous cause of increased bleeding in certain hemophilia patients treated with FVIIII (reviewed in ref 14). One of the important FVIII epitopes to which hemophiliacs produce Abs is composed of residues 484-508 in the A2 domain (15). FVIII is a component of the intrinsic pathway of blood coagulation, serving as a cofactor for Factor IXa catalyzed conversion of Factor X to Factor Xa. CAL derivatives of Factor VIII (FVIII-CAL) are candidate reagents for achieving selective covalent blockage of secreted anti-FVIII Abs and inducing the death of anti-FVIII producing B cells.
FVIII-CALs.

Figure 22:
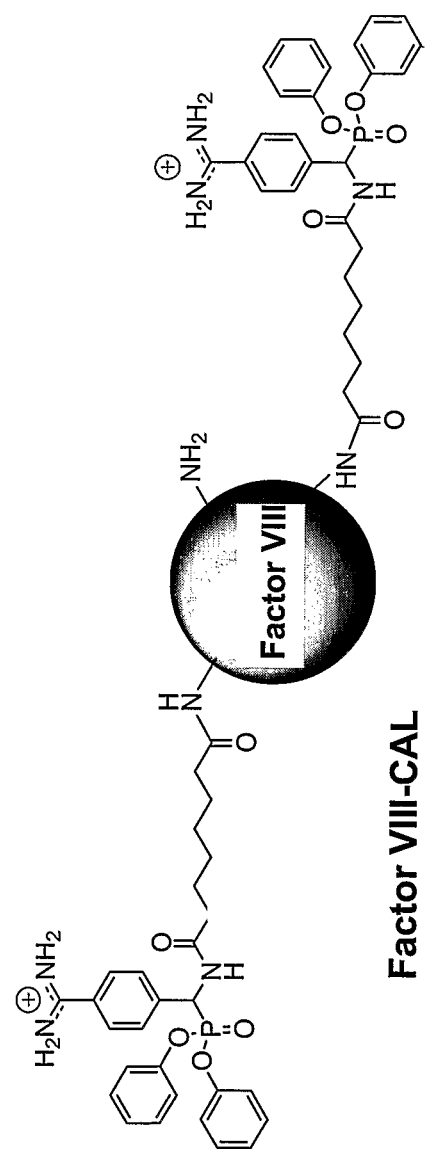

Two CALs are exemplified here: (i) the whole protein FVIII-CAL derivitized at Lys side chains with amidino phosphonate diester groups using recombinant FVIII as precursor (FIG. 22); and (ii) the peptidyl FVIII(484-508)-CAL with the amidino phosphonate diester placed at the C terminus. A flexible linker is used to attach the phosphonate group to the protein, allowing the latter group to sample a larger amount of the conformational space available in the Ab-CAL complex. This is designed to permit the reaction with Ab nucleophiles positioned with somewhat different topography relative to the noncovalent epitope recognition site. Recently, we showed that a single VIP-CAL containing the phosphonate at Lys20 binds covalently to diverse Abs (7), suggesting the feasibility of broad Ab inactivation despite subtle structural differences in the Ab combining sites. Similarly, the FVIII(484-508)-CAL, a derivative of a comparatively small peptide, is likely to enjoy some measure of flexibility, a feature favoring induced fit binding mechanisms and enhanced binding strength. The peptidyl-CAL also overcomes potential stability limitations associated with the whole protein FVIII-CAL (FVIII is a 300 kD protein, composed of two noncovalently bonded subunits prone to dissociation). Methods for CAL syntheses have been described in our previous studies (5-7), entailing phosphonate linkage using conventional linker chemistry and solid phase peptide synthesis, with use of protection groups to avoid undesired reactions. Biotin is incorporated in the CALs to permit determination of covalent complexation.

Secreted Ab Reactivity.

Well characterized polyclonal Abs to FVIII from hemophiliacs and monoclonal Abs raised by experimental immunization are used. The Abs are treated with the two FVIII-CALs, control irrelevant CALs (e.g., gp120-CAL) or control FVIII devoid of covalent reactivity, and free and reversibly bound ligand (CALs and FVIII) are removed by dilution and extensive washing of the Ab-complexes immobilized on a protein G column. Along with untreated Abs, these preparations are analyzed for:

(i) Formation of covalent Ab-CAL complexes by denaturing electrophoresis assay as previously. Kinetic parameters for the reaction will be measured ($K_d$ for the initial noncovalent complexation; $k_3$, first order rate constant for the covalent step) (16).

(ii) Functional effects, i.e., prolongation of coagulation by the aPTT test (activated partial thromblastin time); assay for Factor IX activation (FVIII is an essential cofactor for this step; Chromogenix assay), Bethesda titer of anti-FVIII Abs; and (iii) Binding of FVIII coated on ELISA plates. Irreversible Ab complexation with the CAL is predicted to restore the coagulation parameters to physiological levels. ELISA studies are done to confirm that the Abs-CAL complexes are no longer reactive with FVIII. To determine efficacy in blood, the CALs are mixed with unfractionated blood from patients with acquired hemophilia positive for the Abs, and restoration of blood clotting parameters to physiological levels is determined.

B Lymphocyte Reactivity.

Initial studies consist of treating B lymphocytes obtained from the spleens of mice immunized with FVIII with the FVIII-CALs, control FVIII and an irrelevant CAL for varying lengths of time. Binding of these reagents by the cells is determined by flow cytometry, and the covalent character of the binding, by denaturing electrophoresis of detergent extracts of the cells. The specificity of FVIII-CAL binding is confirmed by competitive inhibition using FVIII devoid of phosphonate groups. Apoptosis is measured using the TUNEL flow cytometry assay, and confirmatory evidence is obtained by examining DNA fragmentation patterns diagnostic of this phenomenon. Following exposure to the CALs, the number of specific Ab-forming cells is measured by flow cytometry using specific Abs to various Ig classes.

Induction of tolerance is indicated by the following data: demonstration of specific and covalent CAL binding to anti-FVIII producing B cells; induction of cell death; and reduction in the number of Ab producing cells.

References

1. Paul S, Volle D J, Beach C M, Johnson D R, Powell M J, Massey R J. Catalytic hydrolysis of vasoactive intestinal peptide by human autoantibody. Science 1989 Jun. 9; 244 (4909):1158-62.
2. Gao Q S, Sun M, Rees A R, Paul S. Site-directed mutagenesis of proteolytic antibody light chain. J Mol Biol 1995 Nov. 10; 253(5):658-64.
3. Lacroix-Desmazes S, Moreau A, Sooryanarayana, Bonnemain C, Stieltjes N, Pashov A, Sultan Y, Hoebeke J, Kazatchkine M D, Kaveri S V. Catalytic activity of antibodies against factor VIII in patients with hemophilia A. Nat Med 1999 September; 5(9):1044-7.
4. Oleksyszyn J, Powers J C. Amino acid and peptide phosphonate derivatives as specific inhibitors of serine peptidases. Methods Enzymol 1994; 244:423-41.
5. Planque S, Taguchi H, Burr G, Bhatia G, Karle S, Zhou Y X, Nishiyama Y, Paul S. Broadly Distributed Chemical Reactivity of Natural Antibodies Expressed in Coordination with Specific Antigen Binding Activity. J Biol Chem 2003 May 30; 278(22):20436-20443.
6. Paul S, Planque S, Zhou Y X, Taguchi H, Bhatia G, Karle S, Hanson C, Nishiyama Y. Specific HIV gp120-cleaving Antibodies Induced by Covalently Reactive Analog of gp120. J Biol Chem 2003 May 30; 278(22):20429-20435.
7. Nishiyama Y, Bhatia G, Bangale Y, Planque S, Mitsuda Y, Taguchi H, Karle S, Paul S. Towards selective covalent inactivation of pathogenic antibodies: A phosphonate diester analog of vasoactive intestinal peptide that inactivates catalytic autoantibodies. J Biol Chem in press (published online ahead of print on Dec. 15, 2003 as 10.1074/jbc.M310950200).
8. Vincent A. Unravelling the pathogenesis of myasthenia gravis. Nat Rev Immunol 2002 October; 2(10):797-804.
9. Gilles J G, Vanzieleghem B, Saint-Remy J M. Factor VIII Inhibitors. Natural autoantibodies and anti-idiotypes. Semin Thromb Hemost. 2000; 26(2): 151-5.
10. Rekvig O P, Nossent J C. Anti-double-stranded DNA antibodies, nucleosomes, and systemic lupus erythematosus: a time for new paradigms? Arthritis Rheum 2003 February; 48(2):300-12.
11. Tomer Y. Anti-thyroglobulin autoantibodies in autoimmune thyroid diseases: cross-reactive or pathogenic? Clin Immunol Immunopathol 1997 January; 82(1):3-11.
12. Nossal G J. B lymphocyte physiology: the beginning and the end. Ciba Found Symp. 1997; 204: 220-30.
13. Planque S, Bangale Y, Song X T, Karle S, Taguchi H, Poindexter B, Bick R, Edmundson A, Nishiyama Y, Paul S. Ontogeny of proteolytic immunity: IgM serine proteases. J Biol Chem in press (published online ahead of print on Jan. 15, 2004 as 10.1074/jbc.M312152200).
14. Lacroix-Desmazes S, Misra N, Bayry J, Artaud C, Drayton B, Kaveri S V, Kazatchkine M D. Pathophysiology of inhibitors to factor VIII in patients with haemophilia A. Haemophilia 2002 May; 8(3):273-9.
15. Healey J F, Lubin I M, Nakai H, Saenko E L, Hoyer L W, Scandella D, Lollar P. Residues 484-508 contain a major determinant of the inhibitory epitope in the A2 domain of human factor VIII. J Biol Chem 1995 Jun. 16; 270(24): 14505-9.
16. Nishiyama Y, Taguchi H, Luo J Q, Zhou Y X, Burr G, Karle S, Paul S. Covalent reactivity of phosphonate monophenyl esters with serine proteinases: an overlooked feature of presumed transition state analogs. Arch Biochem Biophys 2002 Jun. 15; 402(2):281-8.
17. Prasad B V, Hardy M E, Dokland T, Bella J, Rossmann M G, Estes M K. X-ray crystallographic structure of the Norwalk virus capsid. Science. 1999 Oct. 8; 286(5438): 287-90.

EXAMPLE V

Identification of NuRS Using CALs

The present example describes methods to discover NuRs suitable for targeting by hapten CALs and LaCALs.

Nine purified proteins obtained from commercial sources were screened for there nucleophilic reactivity based on their ability to bind hapten CAL I irreversibly (FIG. 23). Seven of the nine proteins displayed hapten CAL I binding resistant to dissociation by boiling and SDS-treatment. Methods employed for conducting the reaction and quantifying the adducts were essentially as in Example I. The mass of the hapten CAL I-protein adduct bands observed by SDS-gel lecetrophoresis s corresponded to the predicted mass of the adducts [gp120 ~120 kD; human serum albumin ~67 kD; soluble epidermal growth factor receptor (sEGFR; residues 1-621) ~85 kD; ovalbumin ~44 kD; soluble CD4 (2 domain, residues 1-183) ~26 kD; calmodulin ~19 kD; casein ~22 kD]. None of the 7 hapten CAL I-binding proteins shown in FIG. 23 is known to display enzymatic activity to our knowledge. All reactions were conducted at an equivalent protein/hapten CAL I molar ratio. The hapten CAL I binding activity per unit protein was variable over a four orders of magnitude. Two protein, human serum albumin and sEGFR, formed adducts with hapten CAL II, a compound devoid of the positively charged amidino group at the P1 position.

These observations indicate the broad distribution of nucleophilic reactivity in non-enzymatic proteins. Based on the variability of the reactivity on different proteins, it is concluded that protein nucleophilicity is a polymorphic property, dependent on the molecular characteristics of the individual protein.

The presence of a positive charge neighboring the electrophilic phosphorus atom in the hapten CAL I favors detection of protein nucleophilicity. In addition to the nucleophile, therefore, the proteins analyzed in FIG. 23 appear to contain recognition sites that can recognize a positive charge in the P1 position.

The hapten CAL I binding properties of gp120 were examined further. The formation of gp120-hapten CAL I adducts was time-dependent (FIG. 24A). The curve shown is the least-square-fit (r2=0.98) for the first-order rate equation [B/Bmax=1−$e^{-k_{obs} \cdot t}$; B, observed band intensity (AAU); Bmax, extrapolated maximum value of B (AAU); kobs, the pseudo-first-order rate constant; t, incubation time].

Increasing adducts were evident as the pH of the reaction solvent was increased, with a sharp inflection evident between pH 7.5 and pH 9.0 (FIG. 24B). The kobs value at each pH was obtained as described for FIG. 24A. The apparent pKa of the nucleophilically reactive site was computed as 7.31±0.08 from the least-square-fit (r2, >0.99) for the following equation: kobs=kobs(max)/(1+$10^{pKa-pH}$), where kobs (max) represents the extrapolative maximum value of kobs. The near-neutral pKa value for the nucleophilic site of gp120 is similar to the enzymatic site found in serine proteases.

Kinetic parameters were extracted by conducting the reaction at varying hapten CAL I concentrations as shown in FIG. 24C. The kobs value at each hapten CAL I concentration was extracted from least-square-fitted progress curves (r2, 0.93-0.99) as before. The dissociation constant of non-covalent 1-gp120 complex (Kd) and the first-order rate constant of covalent adduct formation from the noncovalent complex (k2) was computed from the least-square-fit of the kobs vs [1] plot ($r^2$, 0.96) to the equation, kobs=k2·[1]/(Kd+[1]). The values are: Kd, 0.71±0.50 mM; k2, 0.015±0.007 $min^{-1}$.

Figure 25:
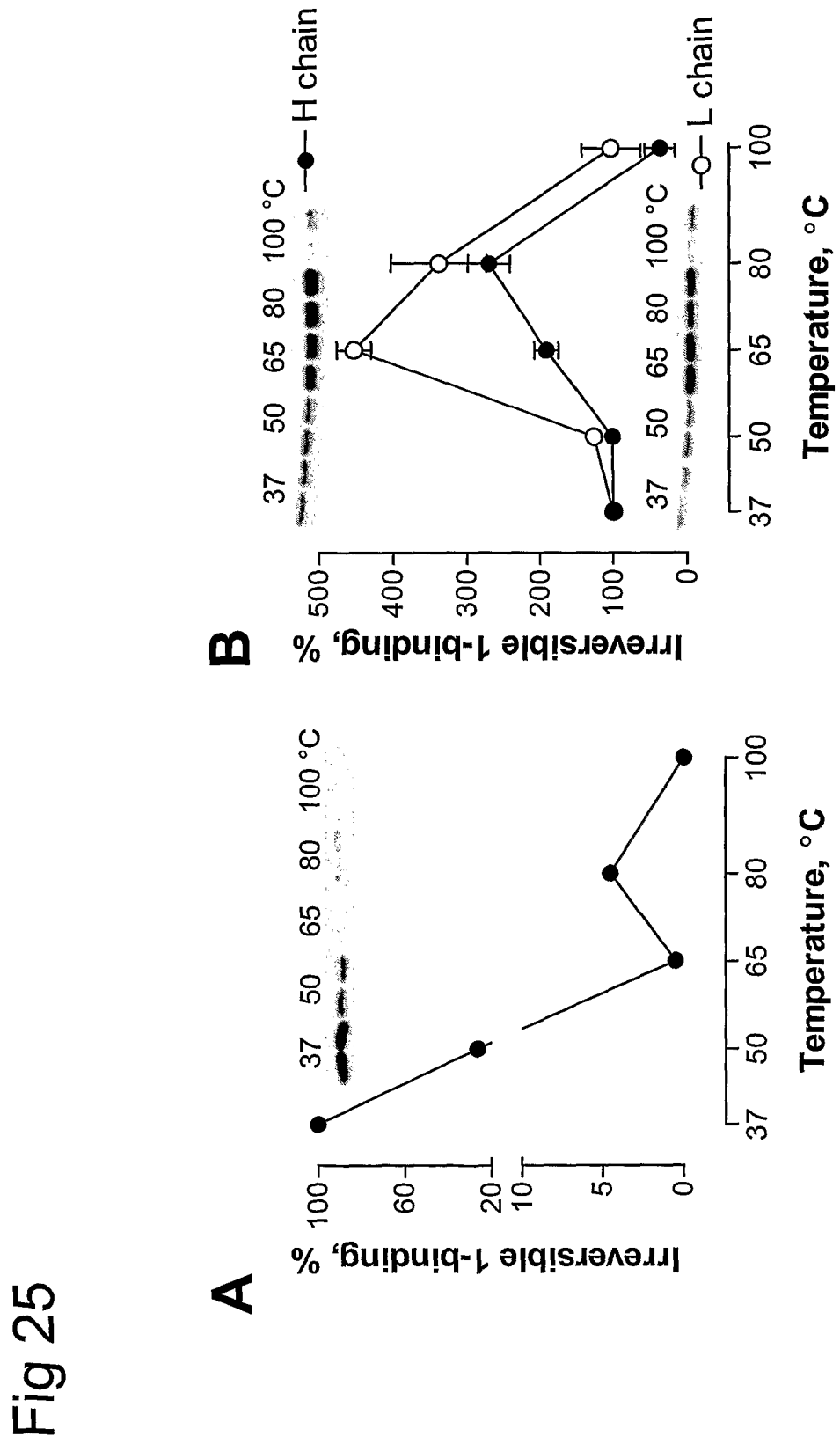

Thermal denaturation studies yielded interesting results indicating the dependence of the nucleophilic reactivity on the protein conformation. As expected, the hapten CAL I binding activity of trypsin was lost nearly completely lost by preheating this protein at 65° C. (FIG. 25). This is consistent with the reported irreversible loss of enzymatic activity of trypsin heated to 60° C. Increasing the temperature to 80° C., however, reproducibly induced an increase in hapten CAL I adduct formation. The results using monoclonal IgG c23.5 were even more dramatic. Following heating of IgG at temperatures up to 80° C., the heavy and light chains of this antibody displayed increased hapten CAL I adduct formation above the baseline value at 37° C. Increasing the temperature further to 100° C. resulted in loss of the nucleophilic reactivity. Previous studies on antigen binding and biophysical analyses have indicated that antibodies undergo irreversible changes in conformations at the temperatures shown to result in increased nucleophilic reactivity.

These observations suggest that nucleophilic sites can be formed in proteins even when they adopt non-physiological conformations. This realization supports the premise that these sites are broadly distributed in proteins and their presence does not imply the presence of proteolytic or other catalytic activities. As noted in Example I, completion of the catalytic cycle in proteolysis requires hydrolysis of covalent acyl-protein complexes. Unless the nucleophilically reactive can also support water attack on the complex, no catalysis will occur.

Next, we sought to study the facilitatory effect of noncovalent binding interactions on the nucleophilic reactivity of calmodulin with VIP-CAL. Calmodulin is known to bind VIP devoid of the CAL group by noncovalent means with high affinity (2). Preparation and characterization of the VIP-CAL is described in Example II, FIG. 13. As shown in FIG. 23, calmodulin displays only low-level nucleophilic reactivity. Nevertheless, calmodulin rapidly formed adducts with VIP-CAL (FIG. 26B). The reaction rate of calmodulin with VIP-CAL was substantially greater than with hapten CAL, even though the latter reagent was available at a 50-fold greater concentration. The second-order rate constants for the reaction of calmodulin with VIP-CAL and hapten CAL were $567\pm77\,M^{-1}\,min^{-1}$ and $0.212\pm0.017\,M^{-1}\,min^{-1}$, respectively. Inclusion of VIP devoid of the CAL group in the reaction mixture resulted in diminished formation of calmodulin adducts with the VIP-CAL, demonstrating the specificity of the reaction.

From these observations, it is evident that: (a) most proteins qualify for designation as NuRs; and (b) NuRs can be targeted for specific covalent inactivation by CAL derivatives of ligands that bind NuRs noncovalently.

References
1. Stallwood D, Brugger C H, Baggenstoss B A, Stemmer P M, Shiraga H, Landers D F, Paul S. Identity of a membrane-bound vasoactive intestinal peptide-binding protein with calmodulin. J Biol Chem 1992 Sep. 25; 267(27):19617-21.

EXAMPLE VI

Irreversible sCD4-CAL Inhibition of gp120

Despite advances in antiretroviral therapy, many patients with HIV-1 infection fail to achieve undetectable viral loads. Resistance mutations account for most treatment failures and resistance is already being seen in the latest generation of peptide-based fusion inhibitors [1]. A new approach to HIV therapy is needed, one from which escape is less likely. High affinity gp120 binding to host cell CD4 receptors initiates HIV infection. Soluble CD4 therapy previously failed to neutralize primary isolates despite promising early results with laboratory adapted strains [2, 3]. This was likely due to a failure to saturate all available gp120 sites with sCD4 [4]. In the present Example, we outline a new approach to HIV inactivation in which covalent binding of sCD4 mimetics to gp120 will compensate for stoichiometric problems seen with conventional CD4.

In view of identification of HIV gp120 as a NuR (see preceding Example), we targeted this protein with CAL derivative of CD4 (FIG. 27). The premise was that one or more nucleophile-electrophile pairing interactions are involved in stabilization of the gp120-CD4 complex. If this hypothesis is valid, the CD4 binding site of gp120 should contain a nucleophile to which the phosphonate can bind covalently.

The two domain soluble form of CD4 corresponding to residues 1-173 is suitable as the starting material for LaCAL preparation. Phosphonate diester groups were placed on Lys side chains of this molecule essentially as described for EGFR described in Example I. Biotin is incorporated at the N-terminus of the peptides or at Lys side chains to monitor the binding reaction.

Certain linear peptides derived from CD4 bind the monomer gp120 as well as the native protein on the viral surface. Among small peptide CD4 analogs, a mimetic containing certain CD4 contact residues embedded in a scyllatoxin scaffold appears to bind gp120 with highest affinity [5]. This peptide serves as an example of peptide-CAL derivatives that can be employed for targeting gp120 (FIG. 27).

The next step was the validation of the sCD4-CAL. This was done as in the preceding Example, by measuring the ability of purified gp120 to form specific and covalent adducts with sCD4-CAL (FIG. 28). Denaturing SDS-electrophoresis showed the formation of a 140 kD adduct in the reaction mixture, corresponding to the expected adducts. Albumin did not form detectable adducts with sCD4-CAL under these reaction conditions. Formation of the sCD4-Cal adducts of gp120 was inhibited by inclusion of sCD$ devoid of the phosphonate diesters in the reaction (FIG. 28B). An irrelevant protein, soybean tryspin inhibitor did not inhibit adduct formation. These data indicate the specificity of the covalent reaction of sCD4-CAL with gp120.

Further characterization of the reaction of CALs can be done as described in the preceding example. Briefly, the Kd and k3 for the reaction are measured (Kd, a measure of the strength of noncovalent binding, and k3, the strength of the nucleophilic reactivity). Specificity is determined by measuring binding of irrelevant CALs, e.g., VIP-CAL and Factor VIII-CAL.

Inactivation of gp120 is measured by determining the potency with which sCD-CALs and their control counterparts devoid of phosphonate diester groups inhibit HIV infection. For this purpose, increasing concentrations of the sCD4-CALs or controls (underivitized peptide [$_{20}$AGSF$_{23}$]ST and underivitized sCD4) are analyzed for neutralization of HIV infection [6]. The sCD4-CAL is incubated with HIV-1 in 96-well assay plates in quadruplicate. 100 TCID50/well virus is used. $3\times10^5$ PHA-stimulated human peripheral blood mononuclear cells (PBMC)/well are added and the plates incubated for 72 hours. The plates are centrifuged and the cells washing the plates three times with fresh medium. After 24 hours incubation, p24 is quantified by enzyme immunoassay using a kit from Beck-manCoulter. The data are fitted with a sigmoidal dose-response curve with variable slope (Hill-type function) using Prism software. The endpoint titer for neutralization is defined as the interpolated titer at which there is a 50% or a 90% inhibition of p24 expression relative to controls.

Several HIV-1 strains drawn from clades A, B, C, D and E are studied. Strains that utilize both R5 and X4 chemokine coreceptors are included in the studies. HIV neutralization by sCD4-Cal at levels exceeding the neutralization by the control sCD4 suggests increased potency due to the covalent reaction.

The covalent reactivity of the sCD4-CALs can be optimized further by using superior leaving groups, e.g., p-nitrophenol, and flanking residue specificity can be improved by empirical studies in which the amidino group and various amino acids are replaced by other analogs/amino acids. Additional factors important for therapy include the stability of the sCD4-CALs in vivo and their ability to penetrate lymphoid organs, which can harbor large amounts of HIV. Improved stability could potentially be obtained by using carbonyl CALs of sCD4. The tissue penetration capability of the CALs could be achieved using peptide tags or conjugation to other molecules that are transported rapidly across various blood-tissue barriers.

References

1. Greenberg M L, Melby T, Sista P, et al.: Baseline and On-treatment Susceptibility to Enfuvirtide Seen in TORO 1 and TORO 2 to 24 Weeks. Conference on Retroviruses and Opportunistic Infections., Boston, Mass., 2003.
2. Liu M A, Liu T. Effect of recombinant soluble CD4 on human peripheral blood lymphocyte responses in vitro. J Clin Invest 1988; 82; 2176-80.
3. Ward R H, Capon D J, Jeff C M, et al. Prevention of HIV-1 IIIB infection in chimpanzees by CD4 immunoadhesin. Nature 1991; 352; 434-6.
4. Daar E S, Li X L, Moudgil T, Ho D D. High concentrations of recombinant soluble CD4 are required to neutralize primary human immunodeficiency virus type 1 isolates. Proc Natl Acad Sci USA 1990; 87; 6574-8.
5. Dowd C S, Leavitt S, Babcock G, et al. Beta-turn Phe in HIV-1 Env binding site of CD4 and CD4 mimetic miniprotein enhances Env binding affinity but is not required for activation of co-receptor/17b site. Biochemistry 2002; 41; 7038-46.
6. D'Souza M P, Geyer S J, Hanson C V, Hendry R M, Milman G. Evaluation of monoclonal antibodies to HIV-1 envelope by neutralization and binding assays: an international collaboration. Aids 1994; 8; 169-81.

EXAMPLE VII

Covalent gp120 Self-Assembly and Vaccine Application

This Example illustrates the utility of preparing covalent mimetics of biological self-assemblies using the LaCAL techniques. Our premise is that weak electrophile-nucleophile pairing provides an important contribution in homo-association and hetero-association reaction involving biological molecules. In the case of a self-associating NuR, this implies that nucleophilic sites in one molecule can pair with electrophilic sites in another molecule as a contributory force in the ordered assembly of the NuR complexes. Placing artificial electrophilic probes within the NuR, therefore, hold the potential of yielding stable and correctly assembled NuR complexes mimicking the native NuR assembled structure. The reaction can anticipated to proceed as an ordered process because noncovalent interactions between gp120 monomers result in correct apposition of the nucleophiles and electrophiles necessary for formation of stable oligomers that mimic the native oligomer.

Previous studies have shown that gp120 expressed in mammalian cells in the absence of gp41 forms oligomeric species under certain experimental conditions [1]. The predominant form is the dimer. The V2 loop has been found to be important for the gp41-independent process of gp120 association [1]. However, the affinity of gp120 monomers for each other is too low to allow formation of stable, noncovalently-bonded oligomers at the concentrations generally used in experimental studies (nanomolar-low micromolar). In the presence of gp41, oligomerization of gp120 is more readily detected.

This premise is tested using the HIV protein gp120, which is expressed on the virion surface as a trimeric assembly in its native state. As shown in Examples VI and VII, gp120 fulfils the criteria for designation as a NuR.

1. gp120-CAL Preparation and Oligomerization.

Preparation of gp120-CAL and biotinylated gp120-CAL is described in our recent publication (2). Briefly, gp120-CAL was prepared from recombinant gp120 and an acylating agent I (FIG. 29), which was prepared from diphenyl amino(4-amidinophenyl)methane-phosphonate [3] and the commercially available homobifunctional cross-linking agent, bis (sulfosuccinimidyl)suberate disodium salt. Biotinylated gp120-CAL (Bt-gp120-CAL) was prepared in the same manner from biotinylated gp120, which was prepared from recombinant gp120 and a commercially available biotinylation reagent, 6-biotinamidohexanoic acid N-hydroxy-3-sulfosuccinimidyl ester. Quantification of biotin introduced and amine consumed using 2-(4'-hydroxyazobenzene)benzoic acid [4] and fluorescamine [5] revealed that biotin/gp120 and phosphonate/gp120 molar ratios were 0.6-0.8 and 5-27, respectively. Note that a variability of phosphonate content does not represent nonreproducibility of the reaction—we attempted to obtain Bt-gp120-CAL with various phosphonate contents to study their role in the oligomerization process. A protein unrelated to gp120, the extracellular domain of epidermal growth factor receptor (exEGFR), was employed as a control for the oligomerization reaction. exEGFR-CAL was prepared using the same method as for gp120-CAL.

Denaturing gel electrophoretic analysis revealed the self-oligomerization of gp120-CAL (FIG. 30A). The oligomers were stable to boiling for 10 min. exEGFR-CAL showed no oligomerized species (FIG. 30B), indicating that the covalent self-oligomerization is a specific property of gp120. Oligomerization appears dependent on the degree of phosphonate-derivatization. gp120 that had not been derivitized with electrophilic groups did not form covalent oligomers. Therefore, the likely reaction is the covalent binding between phosphonate diester moieties and an amino acid expressing an activated nucleophile. As described in Example V, gp120 reacts rapidly with a hapten CAL, consistent with the conclusion reached from the self-oligomerization studies. From these results, the structure of a gp120-CAL is postulated as shown in FIG. 31.

2. Utility of gp120-CAL Oligomers.

Inducing broadly neutralizing Abs has been an important challenge towards development of HIV-1 vaccine [7-10]. Most Abs elicited against monomeric gp120 by experimental vaccination are not capable of neutralizing HIV-1 infectivity of primary isolates [11-14]. These Abs are generally directed against the immunodominant V3 loop of gp120, which is also a region subject to high rates of mutation, allowing emergence of viral variants that can not be controlled by the Abs. Many Abs that recognize the CD4-binding site (CD4bs) of monomer gp120 also failed to neutralize HIV-1. This has been attributed to difference in the structure of the CD4bs of monomer gp120 and native trimeric gp120 expressed on the viral surface. Ab binding to oligomeric gp120 is widely believed to predict the neutralizing activity of Abs [15-17]. Thus, immunogens that are structurally similar to native gp120 are needed both for the purpose of prophylactic vaccine studies as well as passive immunotherapy studies. Substantial efforts have therefore been invested to develop analogs that mimic the native trimeric form of HIV envelope (env) glycoproteins.

We used a gp120-CAL preparations as immunogen to raise antibodies. Details are described in our recent publication (2). The gp120-CAL preparation was composed of 50% monomers, 21% dimers and 29% trimers. As a quality control measure, the immunoreactivity of the gp120-CAL with antibodies Abs raised to control monomeric gp120 devoid of phosphonate was measured. The anti-gp120 antibody preparation displayed 3-4 fold lower binding to immobilized gp120-CAL compared to immobilized gp120 (e.g., at serum dilution of 1:1000, A490 0.44±0.03 for immobilized gp120-CAL and 1.40±0.03 for immobilized gp120). gp120-CAL binding by nonimmune Abs was negligible, indicating that indiscriminate covalent binding at the hapten groups was not a problem. These results indicated the preservation of gp120 antigenic components of gp120-CAL.

Robust polyclonal antibody responses in mice immunized with gp120-CAL were observed by ELISA. Abs raised to gp120-CAL were bound at somewhat greater levels by immobilized gp120-CAL than control gp120 devoid of phosphonate diester groups (FIG. 32). Monoclonal antibodies were prepared from mice immunized with gp120-CAL using routine hybridoma methods. Supernatants from 712 hybridoma wells were screened for binding to gp120-CAL. Following binding of the antibodies to the immobilized gp120-CAL, the ELISA plates were treated with the denaturant SDS to remove reversibly bound antibodies. The SDS treatment allowed essentially complete removal of anti-gp120 antibodies bound by control gp120 devoid of phosphonate groups. In comparison, seven monoclonal anti-gp120-CAL antibodies displayed SDS-resistant gp120-CAL binding (2). Three of these antibodies catalyzed the cleavage of biotinylated gp120 determined by electrophoresis assays (2).

Three of the 7 monoclonal anti-gp120-CAL Abs neutralized the infection of phytohemagglutinin (PHA)-stimulated peripheral blood mononuclear cells (PBMCs) by HIV-1 (clones YZ-18, YZ-22 and YZ-23). The neutralization assays were conducted essentially as described in Example VII, FIG. 33 and our recent publication (18). FIG. 33 shows the results for a primary isolate of HIV-1 belonging to Clade C (strain ZA009, R5 coreceptor dependent). Additional strains neutralized by the three anti-gp120-CAL monoclonal antibodies were BR004 and SF-162. These data indicate the potential of gp120-CAL to induce neutralizing antibody responses.

When used as the basis for experimental HIV vaccines, HIV-1 gp120 monomers have repeatedly failed to elicit effective cross-protective immune responses. In general, these antibodies do not display cross-clade neutralization of HIV infection, particularly HIV strains that utilize CCR5 chemokine coreceptors. The observed neutralizing properties of the antibodies to gp120-CAL suggest that this preparation induced antibodies with epitope specificities different from ordinary gp120. The presence of gp120-CAL oligomers in the immunogens is a likely factor in inducing antibodies to an epitope that is expressed in diverse HIV strains.

3. Improved gp120-CAL Oligomers for Vaccination.

The following strategies are useful in obtaining a candidate oligomeric gp120-CAL vaccine.

- Soluble variants of gp41 are included in the gp120-CAL preparation to promote correct assembly of gp120 oligomers. Varying molar ratios of g41 variants/gp120-CAL mixtures are analyzed to optimize the reaction.
- The structure of monomer gp120-CAL is varied to promote correct self assembly. The linker connecting gp120 to the electrophile may influence the rate of oligomer formation and the level of mimicry of native gp120 oligomers. Moreover, the sites at which the electrophile is introduced into gp120 may be important. Thus linkers with different chain lengths (e.g., 4-carbon and 12-carbon linkers; current version, 8 carbon-length) and reaction chemistry (Asp/Glu attachment and Ser/Thr attachment; current version, Lys attachment) are studied. Bifunctional linkers with 4-carbon and 12-carbon lengths with functional groups allowing attachment to various amino acid side chains are commercially available. Their derivatization with the phosphonate can be done in the same manner as indicated for the acylating agent shown in FIG. 29.

Gp120 oligomers are purified as stable oligomers by gel filtration chromatography. The utility of the gp120-CAL oligomers is determined by immunization of mice as in our previous studies (2). Monomer gp120 devoid of phosphonate groups is used as the control immunogen. Polyclonal IgG samples raised in BALB/c mice are characterized by ELISA using the above immunogens as immobilized antigens and by neutralization of primary isolates of HIV-1. Monoclonal Abs are prepared and screened by ELISA and their neutralizing activity will be determined. The polyclonal IgG studies help define the proportion of the overall Ab response with the desired activities. Monoclonal Ab studies are needed to define the heterogeneity of the response and determine whether individual Abs possess broad neutralizing activity. The monoclonal Abs with promising HIV neutralizing activity in the initial screen are characterized further for binding to the native env complex (by flow cytometry using HIV infected cells) and ability to neutralize diverse, R-5 dependent primary isolates of HIV-1 drawn from various clades.

Methods for antibody production and HIV neutralization are described in detail by other groups and in our own previous publications (2,18). Flow cytometry is done as follows. PHA-stimulated human PBMCs are infected with HIV-1 as above. Since some clades replicate faster than other clades in PBMC, cells are monitored for viral antigen expression by flow cytometry using HIVIG (AIDS Research and Reference Reagent Program) in preliminary experiments. $5\times10^5$ HIV-infected and non-infected, PHA-activated PBMCs will be incubated with the monoclonal Abs for 45 min on ice followed by 2 washes in PBS. Then goat anti-mouse IgG conjugated with fluorescein isothiocyanate (FITC) is added and further incubated on ice for 45 min followed by washing twice in PBS. Stained cells are fixed with 0.1% formalin in PBS and stored at 4° C. in the dark until analysis using a flow cytometer. Controls will include irrelevant, isotype-matched antibodies.

Once the gp120-CAL immunogen is established to induce the formation of broadly neutralizing antibodies, further vaccine development is conducted according to established guidelines for HIV vaccine development suggested by the NIH and the experiences during completed and ongoing clinical trials of candidate HIV vaccines.

Many laboratories have sought to form native trimeric HIV env glycoproteins as candidate vaccines. These attempts, however, have been frustrated by the instability of the complex. Both the inter-gp120 interactions and gp120-gp41 interactions are labile [19,20]. Thus the focus has shifted to engineering of env mimetics with a greater stability, e.g., gp140 constructs in which the proteolytic site located between the gp120 and gp41 sequences has been removed or replaced with an alternative peptide sequence [21-24]. Disulfide bonds have been employed as another means to stabilize the association of gp120 and gp41. Usually, the transmembrane and cytoplasmic regions of gp41 are also truncated to permit efficient secretion as soluble proteins. Covalent gp120-CAL oligomers proposed here hold potential as possible immunogens for inducing protective anti-viral response. For vaccine application, persistent and repeated stimulation of B cells with the oligomers is desirable. Noncovalent oligomers possess limited capability of achieving this goal unless the protein is maintained at concentrations substantially in excess of the Kd of monomer self association. On the other hand, a covalently stabilized oligomer remains associated regardless of the protein concentration, which is hypothesized to allow superior anti-oligomer responses in vivo. The covalent linkage strategy derives from our recent findings that gp120 is a NuR. Unlike commonly used cross-linking agents such as the dicarboxylate disuccinimidy esters, the phosphonate diphenyl ester proposed here is a weak electrophilic reagent. This reagent forms a covalent bond specifically with a nucleophilic functional group (such as the hydroxyl group of Ser) that has been activated with the aid of a general base (such as the imidazole group of His). Thus the cross-linking by the method proposed here is regioselective, that is, it results in cross-linking only if the phosphonate group is suitably apposed with an activated nucleophile.

References

1. Center R J, Earl P L, Lebowitz J, Schuck P, Moss B. The human immunodeficiency virus type 1 gp120 V2 domain mediates gp41-independent intersubunit contacts. J Virol 2000, 74(10): 4448-4455.
2. Paul S, Planque S, Zhou Y X, Taguchi H, Bhatia G, Karle S, Hanson C, Nishiyama Y. Specific HIV gp120-cleaving Antibodies Induced by Covalently Reactive Analog of gp120. J Biol Chem 2003 May 30; 278(22):20429-20435.
3. Oleksyszyn J, Boduszek B, Kam C M, Powers J C. Novel amidine-containing peptidyl phosphonates as irreversible inhibitors for blood coagulation and related serine proteases. J Med Chem 1994, 37(2): 226-231.
4. Green N M. Biochem J 1965, 94: 23c-24c.
5. Udenfriend S, Stein S, Bohlen P, Dairman W, Leimgruber W, Weigele M. Fluorescamine: a reagent for assay of amino acids, peptides, proteins, and primary amines in the picomole range. Science 1972, 178: 871-872.
6. Planque S, Taguchi H, Burr G, Bhatia G, Karle S, Zhou Y X, Nishiyama Y, Paul S. Broadly Distributed Chemical Reactivity of Natural Antibodies Expressed in Coordination with Specific Antigen Binding Activity. J Biol Chem 2003 May 30; 278(22):20436-20443.
7. Burton D R, Moore J P. Why do we not have an HIV vaccine and how can we make one? Nat Med 1998, 4(5 Suppl): 495-498.
8. Ferrantelli F, Ruprecht R M. Neutralizing antibodies against HIV—back in the major leagues? Curr Opin Immunol 2002, 14(4): 495-502.
9. Moore J P, Burton D R. HIV-1 neutralizing antibodies: how full is the bottle? Nat Med 1999; 5(2): 142-144.
10. Letvin N L, Barouch D H, Montefiori D C. Prospects for vaccine protection against HIV-1 infection and AIDS. Annu Rev Immunol 2002, 20: 73-99.
11. Wrin T, Nunberg J H. HIV-1MN recombinant gp120 vaccine serum, which fails to neutralize primary isolates of HIV-1, does not antagonize neutralization by antibodies from infected individuals. AIDS 1994, 8(11): 1622-1623.
12. Mascola J R, Snyder S W, Weislow O S, Belay S M, Belshe R B, Schwartz D H, Clements M L, Dolin R, Graham B S, Gorse G J, Keefer M C, McElrath M J, Walker M C, Wagner K F, McNeil J G, McCutchan F E, Burke D S. Immunization with envelope subunit vaccine products elicits neutralizing antibodies against laboratory-adapted but not primary isolates of human immunodeficiency virus type 1. The National Institute of Allergy and Infectious Diseases AIDS Vaccine Evaluation Group. J Infect Dis 1996, 173(2): 340-348.
13. Connor R I, Korber B T, Graham B S, Hahn B H, Ho D D, Walker B D, Neumann A U, Vermund S H, Mestecky J, Jackson S, Fenamore E, Cao Y, Gao F, Kalams S, Kunstman K J, McDonald D, McWilliams N, Trkola A, Moore J P, Wolinsky S M. Immunological and virological analyses of persons infected by human immunodeficiency virus type 1 while participating in trials of recombinant gp120 subunit vaccines. J Virol 1998, 72(2): 1552-1576.
14. Belshe R B, Gorse G J, Mulligan M J, Evans T G, Keefer M C, Excler J L, Duliege A M, Tartaglia J, Cox W I, McNamara J, Hwang K L, Bradney A, Montefiori D, Weinhold K J. Induction of immune responses to HIV-1 by canarypox virus (ALVAC) HIV-1 and gp120 SF-2 recombinant vaccines in uninfected volunteers. NIAID AIDS Vaccine Evaluation Group. AIDS 1998, 12(18): 2407-2415.
15. Fouts T R, Binley J M, Trkola A, Robinson J E, Moore J P. Neutralization of the human immunodeficiency virus type 1 primary isolate JR-FL by human monoclonal antibodies correlates with antibody binding to the oligomeric form of the envelope glycoprotein complex. J Virol 1997, 71(4): 2779-2785.
16. Fouts T R, Trkola A, Fung M S, Moore J P. Interactions of polyclonal and monoclonal anti-glycoprotein 120 antibodies with oligomeric glycoprotein 120-glycoprotein 41 complexes of a primary HIV type 1 isolate: relationship to neutralization. AIDS Res Hum Retroviruses 1998, 14(7): 591-597.
17. Moore J P, Cao Y, Qing L, Sattentau Q J, Pyati J, Koduri R, Robinson J, Barbas C F 3rd, Burton D R, Ho D D. Primary isolates of human immunodeficiency virus type 1 are relatively resistant to neutralization by monoclonal antibodies to gp120, and their neutralization is not predicted by studies with monomeric gp120. J Virol 1995, 69(1): 101-109.
18. Karle S, Planque S, Nishiyama Y, Taguchi H, Zhou Y X, Salas M, Lake D, Thiagarajan P, Arnett F, Hanson C V, Paul S. Cross-clade HIV-1 neutralization by an antibody fragment from a lupus phage display library AIDS 2004, 18:329-347.
19. Gelderblom H R, Reupke H, Pauli G. Loss of envelope antigens of HTLV-III/LAV, a factor in AIDS pathogenesis? Lancet. 1985, 2(8462): 1016-1017.
20. McKeating J A, McKnight A, Moore J P. Differential loss of envelope glycoprotein gp120 from virions of human immunodeficiency virus type 1 isolates: effects on infectivity and neutralization. J Virol 1991, 65(2): 852-860.
21. Berman P W, Nunes W M, Haffar O K. Expression of membrane-associated and secreted variants of gp160 of human immunodeficiency virus type 1 in vitro and in continuous cell lines. J Virol 1988, 62(9): 3135-3142.
22. Earl P L, Broder C C, Long D, Lee S A, Peterson J, Chakrabarti S, Doms R W, Moss B. Native oligomeric human immunodeficiency virus type 1 envelope glycoprotein elicits diverse monoclonal antibody reactivities. J Virol 1994, 68(5): 3015-3026.
23. Earl P L, Koenig S, Moss B. Biological and immunological properties of human immunodeficiency virus type 1 envelope glycoprotein: analysis of proteins with truncations and deletions expressed by recombinant vaccinia viruses. J Virol 1991, 65(1): 31-41.
24. Binley J M, Sanders R W, Clas B, Schuelke N, Master A, Guo Y, Kajumo F, Anselma D J, Maddon P J, Olson W C, Moore J P. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 2000, 74(2): 627-643.

List of References:

1. Schultz, P. G., and Lerner, R. A. (1995) Science 269, 1835-1842
2. Stewart, J. D., and Benkovic, S. J. (1995) Nature 375, 388-391
3. Paul, S., et. al, (1989) Science 244, 1158-1162
4. Shuster, A. M., et. al. (1992) Science 256, 665-667
5. Matsuura, K., and Sinohara, H. (1996) Biol. Chem. 377, 587-589
6. Lacroix-Desmazes, S., et. al. (1999) Nat. Med. 5, 1044-1047
7. Paul, S., et. al. (1992) J. Biol. Chem. 267, 13142-13145

8. Hifumi, E., Okamoto, Y., and Uda, T. (1999) J. Biosci. Bioengin. 88, 323-327
9. Izadyar, L., et. al. (1993) Proc. Natl. Acad. Sci. USA 90, 8876-8880
10. Gao, Q.-S., Sun, M., Rees, A., and Paul, S. (1995) J. Mol. Biol. 253, 658-664
11. Paul, S., et. al (2001) J. Biol. Chem. 276, 28314-28320
12. Kolesnikov, A. V., et. al. (2000) Proc. Natl. Acad. Sci. USA 97, 13526-13531
13. Katie, S., Nishiyama, Y., et. al. (2003) Vaccine 21, 1213-1218
14. Nishiyama, Y., Taguchi, H., et. al. (2002) Arch. Biochem. Biophys. 402, 281-288
15. Brown, P. M., et. al. (1994) Eur. J. Biochem. 225, 223-233
16. Udenfriend, S., Stein, S., et. al. (1972) Science 178, 871-872
17. Green, N. M. (1965) Biochem. J. 94, 23c-24c
18. Taguchi, H., Burr, G., et. al. (2002) Bioorg. Med. Chem. Lett. 12, 3167-3170
19. Oleksyszyn, J., and Powers, J. C. (1994) in Methods in Enzymology vol. 244 (Barrett, A. J., ed.) pp. 423-441, Academic Press, New York
20. Oleksyszyn, J., Boduszek, B., et. al. (1994) J. Med. Chem. 37, 226-231
21. Zhao, Q., Kovach, I. M., et. al. (1994) Biochemistry 33, 8128-8138
22. Kalaga, R., Li, L., et. al. (1995) J. Immunol. 155, 2695-2702
23. Whitlow, M., Bell, B. A., et. al. (1993) Protein Eng. 6, 989-995
24. Fersht, A. (1985) Enzyme Structure and Mechanism, Freeman and Company, NY
25. Gololobov, G., Sun. M., and Paul, S. (1999) Mel. Immunol. 36, 1215-1222
26. Zhou, G. W., Guo, J., et. al. (1994) Science 265, 1059-1064
27. Wuilmart, C., and Urbain, J. (1976) J. Immunogenet. 3:1-14
28. Jia, Y., Kappock, T. J., et. al. (2000) Biochem. 39, 3927-3936
29. Vocadlo, D. J., Davies, G. J., et. al. (2001) Nature 412, 835-838
30. Interthal, et. al. (2001) Proc. Natl. Acad. Sci. USA 98, 12009-12014
31. Crennell, S. J., Garman, a F., et. al. (1996) J. Mol. Biol. 259, 264-280
32. Wirsching, P., Ashley, J. A., et. al. (1995) Science 270, 1775-1782
33. Takagi, M., Kohda, K., et. al. (1995) FEBS Lett. 375, 273-276
34. Nevinsky, G. A., Kit, Y. Ya., et. al. (1998) Appl. Biochem. Biotechnol. 75, 77-91
35. Jimenez, R., Salazar, G., et. al. (2003) Proc. Natl. Acad. Sci. USA 100, 92-97
36. Braden, B. C., and Pollak, R. J. (1995) FASEB J. 1, 9-16
37. Paul, S., Volle, D. J., et. al. (1990) J. Biol. Chem. 265, 11910-11913
38. Sun, M., Gao, Q. S., et. al. (1997) J. Mol. Biol. 271, 374-385
39. Rao, G., and Philipp, M. (1991) J. Protein Chem. 10, 117-122
40. Lefevre, S., Debat, H., et. al. (2001) FEBS Lett. 489, 25-28
41. Paul, S. (2000) in Chemical Immunology: Catalytic Antibodies, Vol. 77 (Paul, S., ed) pp. 1-158, S. Karger and A. G. Basel, Switzerland
42. Berisha, H. I., Bratut, M., et. al. (2002) Pulm. Pharmacol. Ther. 15, 121-127
43. Voice, J. K., Grinninger, C., et. al. (2003) J. Immunol). 170, 308-314
44. Planque S., Zhou Y.-X., et. al. (2003) FASEB J. 17, 136-143
45. Bermas, B. L.., Petri, M., et. al. (1994) AIDS Res. Hum Retroviruses 10, 1071-1077
46. Vincent, A. (2002) Nat. Rev. Immunol. 2, 797-804
47. Gilles, J. G., Vanzieleghem, B., et. al. (2000) Semin. Thromb. Hemost. 26, 151-155
48. Rekvig, O. P., and Nossent, J. C. (2003) Arthritis Rheum. 48.300-312
49. Paul, S., Voile, D. J., Beach, C. M., et. al. (1989) Science 244, 1158-1162
50. Matsuura, K., and Sinohara, H. (1996) Biol. Chem. 377, 587-589
51. Lacroix-Desmazes, S., Moreau, A., et. al. (1999) Nat. Med. 5, 1044-1047
52. Hatiuchi, K., Hifumi, E., Mitsuda, Y., and Uda, T. (2003) Immunol. Lett. 86, 249-257
53. Shuster, A. M., Gololobov, G. V.. et. al. (1992) Science 256, 665-667
54. Bangale, Y.. Karle, S., et. al. (2003) FASEB J. 17, 628-635
55. Voice, J. K., Dorsam, G., Chan, R. C., et. al. (2002) Regul. Pept. 109, 199-208
56. Maggi, C. A., Giachetti, A., et. al. (1995) Physiol. Rev. 75, 277-322
57. Voice, J. K., Grinninger, C., et. al. (2003) J. Immunol. 170, 308-314
58. Berisha, H. I., Bratut, M., et. al. (2002) Pulm. Pharmacol. Ther. 15, 121-127
59. Gao, Q. S., Sun, M., Rees, A. R, and Paul, S. (1995) J. Mol. Biol. 253, 658-664
60. Oieksyszyn, J., and Powers, J. C. (1994) in Methods in Enzymology, (Barrett, A. J., ed) Vol. 244, pp. 423-441, Academic Press, San Diego, Calif.
61. Paul, S., Tramontano, A., et. al. (2001) J. Biol. Chem. 276, 28314-28320
62. Kolcsnikov, A. V., et. al. (2000) Proc. Natl. Acad. Sci. U.S.A. 97, 13526-13531
63. Oleksyszyn, J., Boduszek, B., et. al. (1994) J. Med. Chem. 37, 226-231
64. Nishiyama, Y., Taguchi, H., et. al. (2002) Arch. Biochem. Biophys. 402, 281-288
65. Wellings, D. A., and Atherton, E. (1997) in Methods in Enzymology (Fields, G. B., ed) Vol. 289, pp. 4467, Academic Press, New York, N.Y.
66. Aletras, A:, Barlos, K., et. al. (1995) Int. J. Pept. Protein Res. 45, 488-496
67. Paul, S., Sun, M., et. al. (1992) J. Biol. Chem. 267, 13142-13145
68. Paul, S., Mei, S., et. al. (1991) J. Biol. Chem. 266, 16128-16134
69. Sun, M., Gao, Q. S., et. al. (1997) J. Mol. Biol. 271, 374-385
70. Oleksyszyn, J., and Powers, J. C. (1991) Biochemistry 30, 485-493
71. Sampson, N. S., and Bartlett, P. A. (1991) Biochemistry 30, 2255-2263
72. Means, G. E and Wu, H. L. (1979) Arch. Biochem. Biophys. 194, 526-530
73. Schwartz, M. (1982) Clin. Chim. Acta 124, 213-223
74. Marangoni, A. (2003) Enzyme Kinetics: A Modern Approach, Wiley and Sons, Hoboken, N.J.
75. Planque, S., Taguchi, H., et. al. (2003) J. Biol. Chem. 278, 20436-20443

76. Paul, S., Planque, S., et. al. (2003) J. Biol. Chem. 278, 20429-20435
77. Sun, M., Li, L., Gao, Q. S., and Paul, S. (1994) J. Biol. Chem. 269, 734-738
78. Kaartinen, M., Pelkonen, J., and Makela, O. (1986) Eur. J. Immunol. 16, 98-105
79. Mitchell, T. J., and Reilly, T. M. (1990) Pept. Res. 3, 277-281
80. Nishiyama Y, Bhatia G., et. al. J Biol Chem 2004 Feb. 27; 279(9):7877-83.
81. Paul S, Planque S., et. al. J Biol Chem 2003 May 30; 278(22):20429-20435.
82. Planque S, Taguchi H., et. al. J Biol Chem 2003 May 30; 278(22):20436-20443.
83. Nossal G J. B lymphocyte physiology: the beginning and the end. Ciba Found Symp. 1997; 204:220-31.
84. Stollar B D. FASEB J. 1994 Mar. 1; 8(3):337-42.
85. Stemmer C, et. al. J Biol. Chem. 1996 Aug. 30; 271(35):21257-61.
86. Groggel, G. (1999) Kidney damage in autoimmune disease. In: S. Paul (Ed) Autoimmune Reactions. Humana Press, Totowa, p. 249-268.
87. Yanase, et. al. (1999) Cellular entry and nuclear localization of anti-DNA antibodies. In: S. Paul (Ed) Autoimmune Reactions. Humana Press, Totowa, p. 293-304.
88. Alarcon-Segovia D, Llorente L. Clin Exp Immunol. 1983 May; 52(2):365-71.
89. Raz E, et. al. Eur J Immunol. 1993 February; 23(2):383-90.
90. Zack. et. al. (1999) Cell and nuclear penetration by autoantibodies. In: S. Paul (Ed) Autoimmune Reactions. Humana Press, Totowa, p. 305-319.
91. Shuster et. al. 1992 May 1; 256(5057):665-7.
92. Suchkov S V. Bull Exp Biol Med. 2001 April; 131(4):353-5.
93. Matsuzaki Y, Hamasaki Y, Said S I. Science. 1980 Dec. 12; 210(4475):1252-3.
94. Delgado M, Abad C., et. al. Nat. Med. 2001 May; 7(5):563-8.
95. Bangale Y, Cavill D et. al. Peptides 2002 December: 23(12):2251-7.
96. Bangale Y, Karle S., et. al. FASEB J 2003 April; 17(6):628-35.
97. Paul S, Said S T, et. al. J Neuroimmunol 1989 July; 23(2):133-42.
98. Ganea D. Adv Neuroimmunol. 1996; 6(1):61-74.
99. Dorsam G, Voice J, Kong Y, Goetzl E J. Ann N Y Acad Sci. 2000; 921:79-91.
100. Goetzl et. al. Proc Natl Acad Sci USA. 2001 Nov. 20; 98(24):13854-9.
101. Bracci-Laudiero L, Aloe L, et. al. Neurosci Left. 1998 May 29; 248(2):97-100.
102. Blatt N B. Glick G D. Pharmacol Ther. 1999 August; 83(2):125-39.
103. Lefkowith J B, Di Valerio R., et. al. J. Immunol. 1996 Aug. 1; 157(3):1297-305.
104. Barbas et. al. Proc Natl Acad Sci USA. 1995 Mar. 28; 92(7):2529-33.
105. Winkler et. al. Clin Exp Immunol. 1991 September; 85(3):379-85.
106. Ackroyd P C, Cleary J, Glick G D. Biochemistry. 2001 Mar. 6; 40(9):2911-22.
107. Herrmann et. al. Eur J. Immunol. 1995 July; 25(7):1897-904.
108. Straub et. al. Am Chem Soc 1982; 104:6754-6764.
109. Froehler et. al. Nucleic Acids Res. 1986 Jul. 11; 14(13):5399-407.
110. Walter J, Bode W. Hoppe Seylers Z Physiol Chem. 1983 August; 364(8):949-59.
111. Chen et. al. Arch Biochem Biophys. 1995 Sep. 10; 322(1):198-203.
112. Taguchi et. al. Bioorg Med Chem Lett 2002 Nov. 4; 12(21):3167-70.
113. Nishiyama et. al. Arch Biochem Biophys 2002 Jun. 15; 402(2):281-8.
114. Pisetsky D S, Gonzalez T C. Clin Exp Immunol. 1999 May; 116(2):354-9.
115. Tawfik et. al. Proc Natl Acad Sci USA 1995 Mar. 14; 92(6):2145-9.
116. Licht et. al. Arthritis Rheum. 2001 June; 44(6):1320-30.
117. Desai D D, Marion T N. Induction of anti-DNA antibody with DNA-peptide complexes. Int Immunol. 2000 November; 12(10:1569-78.
118. Napirei M, Karsunky H, et. al. Nat. Genet. 2000 June; 25(2):177-81.
119. Voice, et. al. 2002 Experimental Biology Meeting, Apr. 20, 2002, New Orleans, La.
120. Paul S. Catalytic activity of anti-ground state antibodies, antibody subunits, and human autoantibodies. Appl Biochem Biotechnol. 1994 May; 47(2-3):241-53; 253-5.
121. Paul, S. Protein engineering. In Molecular Biotechniques. Ed., Walker J. (Humana Press, Totowa, N.J.). Chapter 43, pp 547-566, 1998.
122. Oleksyszyn J, Powers J C. Methods Enzymol 1994; 244:423-41.
123. Sampson N S, Bartlett P A. Biochemistry 1991 Feb. 26; 30(8):2255-63.
124. Paul et. al. J Biol Chem 2001 Jul. 27; 276(30):28314-20.
125. Kolesnikov et. al. Proc Nati Acad Sci USA 2000 Dec. 5; 97(25);13526-31.
126. Goodnow C C. Ciba Found Symp 1997; 204:190-202; discussion 202-207.
127. Nossal G J. J Exp Med. 1996 May 1; 183(5):1953-6.
128. Kohler H, Paul S. Immunol Today 1998; 19:221-227.
129. Paul S, Voile D J, et. al. Science 1989 Jun. 9; 244(4909):1158-62.
130. Gao Q S, Sun M, Rees A R, Paul S. J Mol Biol 1995 Nov. 10; 253(5):658-64.
131. Lacroix-Desmazes S, Moreau A, et. al. Nat Med 1999 September; 5(9):1044-7.
132. Oleksyszyn J, Powers J C. Methods Enzymol 1994; 244:423-41.
133. Planque et. al. J Biol Chem 2003 May 30; 278(22):20436-20443.
134. Paul et al, Y. J Biol Chem 2003 May 30; 278(22):20429-20435.
135. Vincent A. Nat Rev Immunol 2002 October; 2(10):797-804.
136. Gilles et. al. Semin Thromb Hemost. 2000; 26(2): 151-5.
137. Rekvig O P, Nossent. J C. Arthritis Rheum 2003 February; 48(2):300-12.
138. Tomer Y. Clin Immunol Immunopathol 1997 January; 82(1):3-11.
139. Nossal G J. Ciba Found Symp. 1997; 204: 220-30.
140. Lacroix-Desmazes et. al. Haemophilia 2002 May; 8(3):273-9.
141. Healey J F, Lubin I M, et. al. J Biol Chem 1995 Jun. 16; 270(24):14505-9.
142. Nishiyama et. al. Arch Biochem Biophys 2002 Jun. 15; 402(2):281-8.
143. Prasad et. al. Science. 1999 Oct. 8; 286(5438): 287-90.
144. Stallwood et. al. J Biot Chem 1992 Sep. 25; 267(27):19617-21.
145. Liu M A, Liu T. J Clin Invest 1988; 82; 2176-80.

146. Ward R H, Capon D J, Jeff C M, et al. Nature 1991; 352; 434-6.
147. Daar E S, Li X L, Moudgil T, Ho D Ta, Proc Nati Acad Sci USA 1990; 87; 6574-8.
148. Dowd C S, Leavitt S, Babcock G, et al. Biochemistry 2002; 41; 7038-46.
149. D'Souza M P, Geyer S J, et. al. Aids 1994; 8; 169-81.
150. Center R J. Earl P L, et. al. J Vim) 2000, 74(10): 4448-4455.
151. Paul S, Planque S, et. al. J Biot Chem 2003 May 30; 278(22):20429-20435.
152. Oleksyszyn J, Boduszek B, et. at. J Med Chem 1994, 37(2); 226-231.
153. Green N M. Biochem J 1965, 94: 23c-24c.
154. Udenfriend S, Stein S, et. al. Science 1972, 178: 871-872.
155. Planque S, Taguchi H, et. al. J Biol Chem 2003 May 30; 278(22):20436-20443.
156. Burton D R, Moore J P. Curr Opin Immunol 2002, 14(4); 495-502.
157. Moore J P, Burton D R. Nat Med 1999; 5(2): 142-144.
158. Lavin N L, Barouch D H, Montefiori D C. Annu Rev Immunol 2002, 20: 73-99.
159. Wrin T, Nunberg J H. AIDS 1994, 8(11): 1622-1623.
160. Mascola J R, Snyder S W, et. al. J Infect Dis 1996, 173(2): 340-348.
161. Connor R I, Korber B T, et. al. J Virol 1998, 72(2): 1552-1576.
162. Belshe R B, Gorse G J, et. al. AIDS 1998. 12(18): 2407-2415.
163. Fouts T R, Binley J M, et. al. Virol 1997, 71(4): 2779-2785.
164. Fouts et. al. AIDS Res Hum Retroviruses 1998, 14(7): 591-597.
165. Moore et. al. J Virol 1995, 69(1): 101-109.
166. Karle S, Planque S, et. al. AIDS 2004, 18:329-347.
167. Gelderblom H R, Reupke H, Pauli G. Lancet. 1985, 2(8462): 1016-1017.
168. McKeating J A, McKnight A, Moore J P.J Virol 1991, 65(2): 852-860.
169. Berman P W, Nunes W M., Haffar O K. J Virol 1988, 62(9): 3135-3142.
170. Earl et. al. J Virol 1994, 68(5): 3015-3026.
171. Earl P L, Koenig S, Moss B. J Virol 1991, 65(1): 31-41.

TABLE 1

| Target Antigen | Disease Indications |
|---|---|
| CD4 | Rheumatoid Arthritis, Asthma, Transplantation, Autoimmune Disease |
| HER 2 | Various Tumors |
| EGFR | Various Tumors |
| CTLA-4 | Various Tumors, Microbial Disease |
| Macrophage Inhibitory Factor | Inflammatory and Autoimmune Disease |
| CD80 (B7-1) | Inflammatory and Autoimmune Disease, Atherosclerosis |
| CD86 (B7-2) | Inflammatory and Autoimmune Disease, Atherosclerosis |
| CD28 | Inflammatory and Autoimmune Disease, Atherosclerosis |
| CD70 | Inflammatory and Autoimmune Disease, Atherosclerosis |
| CD11b/CD18 | Arthritis, Inflammatory and Autoimmune Disease |
| CD23 | Arthritis, Inflammatory and Autoimmune Disease |
| ICAM-1 | Inflammatory and Autoimmune Disease, Rheumatoid Arthritis, Inflammatory Bowel Disease, Organ Transplant Rejection, Psoriasis, Atherosclerosis |

TABLE 1-continued

| Target Antigen | Disease Indications |
|---|---|
| VLA-4 Integrin Receptor | Inflammatory and Autoimmune Disease |
| TNF-alpha | Rheumatoid Arthritis, Autoimmune Disease, Neurotropic Pain, Ischemia-reperfusion Injury, Septic Shock, SIRS, ARDS, Multiple Sclerosis, AIDS |
| Complement Component C5 | Autoimmune Disease, Immunosuppression |
| IL-1 beta Receptor | Rheumatoid Arthritis, Autoimmune Disease, Neurotropic Pain, Ischemia-reperfusion Injury, Septic Shock, SIRS, ARDS |
| IL-1 beta | Rheumatoid Arthritis, Autoimmune Disease, Neurotropic Pain, Ischemia-reperfusion Injury, Septic Shock, SIRS, ARDS |
| GPIIb/IIIa Receptor | Anti-thrombotic, Use in combination with Angioplasty, Percutaneous Coronaryr Intervention, Unstable Angina, Stroke |
| Plasminogen Activator Inhibitor (PAI-1) | Anti-coagulant |
| IL-4 | Thrombolytic |
| IL-4 Receptor | Asthma |
| IL-5 | Asthma |
| IL-5 Receptor | Allergy |
| IgE | Allergy |
| Eotaxin | Allergic Asthma and Allergic Rhinitis |
| Eotaxin Receptor | Allergic Inflammatory Disease, Allergic Asthma |
| PDGF | Allergic Inflammatory Disease, Allergic Asthma |
| PDGF beta Receptor | Vascular Disease, Restinosis |
| Alpha.v.beta.3 Integrin | Vascular Disease, Restenosis, Inhibit Pathogenic Bone Resorption |
| Beta-amyloid peptide | Alzheimer's Disease |

The invention claimed is:

1. A ligand analog that binds covalently to a nucleophilic receptor (NuR), wherein said ligand analog has the formula

L–E wherein L is a ligand that binds noncovalently to a NuR, wherein L comprises a continuous or discontinuous epitope that binds noncovalently to said NuR, and E is an electrophilic group conjugated to a functional group of an amino acid side chain of L having the formula

Y–Y'–Y"– wherein
Y is an electrophilic group that reacts covalently with NuR,
Y' is a charged or neutral group, or is absent, and
Y" is a linker, covalent bond or atom.

2. The ligand analog of claim 1, wherein Y" is a linker.

3. The ligand analog of claim 1, wherein Y' is a charged or neutral group.

4. The ligand analog of claim 1, wherein the side chain functional group is selected from the group consisting of —$NH_2$, —COOH, —SH, and —OH.

5. The ligand analog of claim 1, wherein the amino acid side chain is a side chain of alanine, leucine, isoleucine, valine, methionine, cysteine, aspartic acid, glutamic acid, asparagine, glutamine, lysine, arginine, phenylalanine, tyrosine, tryptophan, histidine, serine, threonine or proline.

6. The ligand analog of claim 1, wherein Y" is a suberoyl, pimeroyl, aminohexanoyl, aminoacetyl, poly(ethylene oxide), α, ω-dicarboxyl or acetylenedicarboxyl group.

7. The ligand analog of claim 1, wherein Y' is a charged group selected from amino(4-amidinophenyl)methyl, 2,6-di-aminopentyl, 1-amino-4-guanidinobutyl, 1-amino-3-car-boxylpropyl and amino(4-carboxylphenyl)methyl.

8. The ligand analog of claim 1, wherein Y' is a neutral group selected from amino(phenyl)methyl, 1-amino-2-phenylethyl, 1-amino-2-methylbutyl, aminomethyl, 2-aminoethyl and 1-aminocyclohexyl.

9. The ligand analog of claim 1, wherein Y comprises an electrophilic atom Z attached to one or more substituents R.

10. The ligand analog of claim 9, wherein substituent R is an electron withdrawing group.

11. The ligand analog of claim 10, wherein R is selected from phenoxyl, 4-nitrophenoxyl, 4-cyanophenoxyl, pentachlorophenoxyl, 4-nitrophenyl, 4-cyanophenyl, cyanomethoxyl, trifluoromethoxyl and 4-nitrophenylmercaptyl.

12. The ligand analog of claim 9, wherein R is an electron donating group.

13. The ligand analog of claim 12, wherein R is selected from 4-methoxyphenoxyl, 4-methylphenoxyl, methoxymethoxyl, 4-methoxyphenyl, 4-methylphenyl, methoxymethyl and 4-methoxyphenylmercaptyl.

14. The ligand analog of claim 9, wherein Z is a phosphorus, carbon, boron or vanadium atom.

15. The ligand analog of claim 14, wherein Y has the formula:

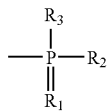

wherein $R_1$ is an oxygen or sulfur atom, and $R_2$ and $R_3$ are independently hydrogen, oxygen, fluorine, chlorine, bromine, iodine, sulfur, hydroxyl, sulfhydryl, amino, alkoxy or phenoxy.

16. The ligand analog of claim 9, wherein R is glyoxylpeptide or aminoacylpeptide.

17. The ligand analog of claim 1, wherein L comprises an epitope from a protein selected from the group consisting of vasoactive intestinal peptide (VIP), Factor VIII, β-amyloid peptide, CD4, extracellular domain of epidermal growth factor erceptor (EGFR), human immunodeficiency virus (HIV) gp120; HIV gp160, Lexl repressor, gag, pol, hepatitis B surface antigen, diptheria toxin, C. tetani toxin, C. botulinum toxin, and pertussis toxin.

18. The ligand analog of claim 1, wherein NuR is an antibody.

19. The ligand analog of claim 18, wherein the antibody is a member of the group consisting of alloantibodies to Factor VIII, red blood cell antigens, platelet antigens, kidney antigens, heart antigens and lung antigens.

20. The ligand analog of claim 1, wherein NuR is gp120.

21. The ligand analog of claim 20, wherein L-E is electrophilic gp120.

22. The ligand analog of claim 1, wherein:
the amino acid side chain is a side chain of alanine, leucine, isoleucine, valine, methionine, cysteine, aspartic acid, glutamic acid, asparagine, glutamine, lysine, arginine, phenylalanine, tyrosine, tryptophan, histidine, serine, threonine or proline;
Y" is a suberoyl, pimeroyl, aminohexanoyl, aminoacetyl, poly(ethylene oxide), α, ω-dicarboxyl or acetylenedicarboxyl group; and
Y' is a amino(4-amidinophenyl)methyl, 2,6-diaminopentyl, 1-amino-4-guanidinobutyl, 1-amino-3-carboxylpropyl, amino(4-carboxylphenyl)methyl, amino(phenyl)methyl, 1-amino-2-phenylethyl, 1-amino-2-methylbutyl, aminomethyl, 2-aminoethyl or 1-aminocyclohexyl group.

23. The ligand analog of claim 22, wherein L comprises vasoactive intestinal peptide (VIP), Factor VIII, β-amyloid peptide, CD4, extracellular domain of epidermal growth factor receptor (EGFR), human immunodeficiency virus (HIV) gp120; HIV gp160, Lexl repressor, gag, pol, hepatitis B surface antigen, diptheria toxin, C. tetani toxin, C. botulinum toxin, or pertussis toxin.

24. An isolated covalent complex comprising:
a ligand analog according to claim 1 that binds noncovalently to a nucleophilic receptor; and
the nucleophilic receptor,
wherein the ligand analog and the nucleophilic receptor are covalently bound to each other.

25. A pharmaceutical composition, comprising:
a ligand analog according to claim 1; and
a pharmaceutically acceptable carrier.

26. The ligand analog of claim 5, wherein the side chain functional group of L is a side chain functional group of lysine, aspartic acid, glutamic acid, cysteine, serine, threonine, or tyrosine.

27. The ligand analog of claim 1, wherein L comprises an epitope from a protein selected from the group consisting of vasoactive intestinal peptide (VIP), Factor VIII, β-amyloid peptide, CD4, extracellular domain of epidermal growth factor receptor (EGFR), and human immunodeficiency virus (HIV) gp120.

28. The ligand analog of claim 22, wherein L comprises an epitope from a protein selected from the group consisting of vasoactive intestinal peptide (VIP), Factor VIII, β-amyloid peptide, CD4, extracellular domain of epidermal growth factor receptor (EGFR), and human immunodeficiency virus (HIV) gp120.

* * * * *